United States Patent
Jing et al.

(10) Patent No.: US 9,540,426 B2
(45) Date of Patent: Jan. 10, 2017

(54) MAMMALIAN CELL CULTURE PROCESSES FOR PROTEIN PRODUCTION

(75) Inventors: Ying Jing, Jamesville, NY (US); Zhengjian Li, Jamesville, NY (US); Yueming Qian, Manlius, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/897,857

(22) Filed: Oct. 5, 2010

(65) Prior Publication Data

US 2011/0081679 A1 Apr. 7, 2011

Related U.S. Application Data

(60) Provisional application No. 61/278,343, filed on Oct. 6, 2009.

(51) Int. Cl.
  *C07K 14/47* (2006.01)
  *C07K 14/705* (2006.01)
  *C12N 5/00* (2006.01)

(52) U.S. Cl.
  CPC ......... *C07K 14/47* (2013.01); *C07K 14/70521* (2013.01); *C12N 5/0018* (2013.01); *C07K 2319/02* (2013.01); *C07K 2319/30* (2013.01); *C12N 2501/39* (2013.01); *C12N 2511/00* (2013.01)

(58) Field of Classification Search
  None
  See application file for complete search history.

(56) References Cited

U.S. PATENT DOCUMENTS

| | | | |
|---|---|---|---|
| 4,357,422 A | | 11/1982 | Giard et al. |
| 5,089,397 A | * | 2/1992 | Kushner et al. ............. 435/69.1 |
| 5,342,764 A | * | 8/1994 | Johnson et al. ............. 435/69.1 |
| 5,434,131 A | | 7/1995 | Linsley et al. |
| 5,637,481 A | | 6/1997 | Ledbetter et al. |
| 5,705,364 A | | 1/1998 | Etcheverry et al. |
| 5,721,121 A | | 2/1998 | Etcheverry et al. |

(Continued)

FOREIGN PATENT DOCUMENTS

| | | |
|---|---|---|
| AU | 2004/201287 A1 | 4/2004 |
| JP | 2001-269194 | 10/2001 |

(Continued)

OTHER PUBLICATIONS

Machuca et al., Dexamethasone protection from TNF-alpha-induced cell death in MCF-7 cells requires NF-kappaB and is independent from AKT., BMC Biology (2006), vol. 7:9, pp. 1-12.*

(Continued)

*Primary Examiner* — Alexander Kim
(74) *Attorney, Agent, or Firm* — Nickki L. Parlet

(57) ABSTRACT

The present invention describes methods and processes for the production of proteins, particularly glycoproteins, by animal cell or mammalian cell culture, preferably, but not limited to, fed-batch cell cultures. In one aspect, the methods comprise the addition of glucocorticoid compound during the culturing period. The addition of glucocorticoid compound sustain a high viability of the cultured cells, and can yield an increased end titer of protein product, and a high quality of protein product, as determined, e.g., by sialic acid content of the produced protein.

1 Claim, 22 Drawing Sheets

A

B

(56) References Cited

U.S. PATENT DOCUMENTS

| | | | |
|---|---|---|---|
| 5,773,253 | A | 6/1998 | Linsley et al. |
| 5,844,095 | A | 12/1998 | Linsley et al. |
| 5,851,795 | A | 12/1998 | Linsley et al. |
| 5,851,800 | A | 12/1998 | Adamson et al. |
| 5,976,833 | A | 11/1999 | Furukawa et al. |
| 6,090,914 | A | 7/2000 | Linsley et al. |
| 6,113,898 | A | 9/2000 | Anderson et al. |
| 6,472,175 | B1 | 10/2002 | Wood |
| 7,094,874 | B2* | 8/2006 | Peach et al. ............ 530/350 |
| 7,332,303 | B2 | 2/2008 | Schilling et al. |
| 7,541,164 | B2 | 6/2009 | Schilling et al. |
| 2005/0084933 | A1* | 4/2005 | Schilling et al. ......... 435/69.1 |
| 2009/0252749 | A1 | 10/2009 | Leister et al. |

FOREIGN PATENT DOCUMENTS

| | | |
|---|---|---|
| WO | WO86/05807 | 10/1986 |
| WO | WO87/04462 | 7/1987 |
| WO | WO89/01036 | 2/1989 |
| WO | WO89/10404 | 11/1989 |
| WO | WO91/06657 | 5/1991 |
| WO | WO9203535 * | 5/1992 |
| WO | WO99/61650 | 12/1999 |
| WO | WO00/36092 | 6/2000 |
| WO | WO00/65070 | 11/2000 |
| WO | WO01/05956 A2 | 1/2001 |
| WO | WO01/92337 A2 | 12/2001 |

OTHER PUBLICATIONS

Jing et al., Sialyation Enhancement of CTLA4-Ig Fusion Protein in Chinese Hamster Ovary Cells by Dexamethasone, Biotechnology and Bioengineering, (Epub Jun. 2, 2010), vol. 107, pp. 488-496.*

Roy et al., Screening of some anti-androgenic endocrine disruptors using a recombinant cell-based in vitro bioassay., The Journal of Steroid Biochemistry & Molecular Biology (2004), vol. 88, pp. 157-166.*

Coughlan et al., The biochemical consequences of alpha2,6(N) sialyltransferase induction by dexamethasone on sialoglycoprotein expression in the rat H411e hepatoma cell line., FEBS Lett. (1997), vol. 413(2), pp. 389-393.*

Bork,K. et al., "Increasing the Sialylation of Therapeutic Glycoproteins: The Potential of the Sialic Acid Biosynthetic Pathway", J. of Pharmaceutical Sciences, vol. 98 (10), pp. 3499-3508 (2009).

Coughlan, C. et al., "The biochemical consequences of α2,6(N) sialyltransferase induction by dexamethasone on sialoglycoprotein expression in the rat H411e hepatoma cell line", FEBS Letters, vol. 413, pp. 389-393 (1997).

Linsley, Peter et al., "Immunosuppression in Vivo by a Soluble Form of the CTLA-4 T Cell Activation Molecule", Science, vol. 257, pp. 792-795 (1992).

Lipscomb, Matthew et al., "Production of a Secreted Glycoprotein from an Inducible Promoter System in a Perfusion Bioreactor", Biotechnol. Prog., vol. 20, pp. 1402-1407 (2004).

Jing, Y. et al., "Sialylation Enhancement of CTLA4-Ig Fusion Protein in Chinese Hamster Ovary Cells by Dexamethasone", Biotechnology and Bioengineering, vol. 107(3), pp. 488-496 (2010).

Qian, Y. et al., "Glucocorticoid Receptor-Mediated Reduction of IgG-Fusion Protein Aggregation in Chinese Hamster Ovary Cells", Biotechnol. Prog., vol. 26(5), pp. 1417-1423 (2010).

VanDamme, V. et al., "Transcriptional induction of β-galactoside α-2, 6-sialyltransferase in rat fibroblast by dexamethasone", Eur. J. Biochem., vol. 211, pp. 135-140 (1993).

Xia, M. et al., "Dexamethasone enhances CTLA-4 expression during T cell activation", Cellular and Molecular Life Sciences, vol. 55, pp. 1649-1656 (1999).

U.S. Appl. No. 60/214,065, filed Jun. 26, 2000.
U.S. Appl. No. 60/287,576, filed May 26, 2000.
U.S. Appl. No. 09/579,927, filed May 26, 2000.

Anumula, K. et al., "Rapid characterization of asparagine-linked oligosaccharides isolated from gylcoproteins using a carbohydrate analyzer", Eur J. Biochem., vol. 195, pp. 269-280 (1991).

Barnes, D., "Serum-free Cell Culture: a Unifying Approach", Cell, vol. 22, pp. 649-655 (1980).

Bevilacqua, M. et al., "Selectins", J. Clin. invest., vol. 91, pp. 379-387 (1993).

Chakravarthi, S. et al., "Glutathione is Required to Regulate the Formation of Native Disulfide Bonds within Proteins Entering the Secretory Pathway", The J. of Biological Chemistry, vol. 279(38), pp. 39872-39879 (2004).

Chandler, V. et al., "DNA Sequences Bound Specifically by Glucocorticoid Receptor In Vitro Render a Heterologous Promoter Hormone Responsive In Vivo", Cell, vol. 33, pp. 489-499 (1983).

Chirino, A. et al., "Characterizing biological products and assessing comparability following manufacturing changes", Nature Biotechnology, vol. 22(11), pp. 1383-1391 (2004).

Colbère-Garapin, F. et al., "A New Dominant Hybrid Selective Marker for Higher Eukaryotic Cells", J. Mol. Biol., vol. 150, pp. 1-14 (1981).

Cromwell, M. et al., "Protein Aggregation and Bioprocessing", The AAPS Journal, vol. 8(3), pp. E572-E579 (2006).

Crowell, C. et al., "Amino Acid and Manganese Supplementation Modulates the Glycosylation State of Erythropoietin in a CHO Culture System", Biotechnology and Bioengineering, vol. 96(3), pp. 538-549 (2007).

Crouse, G. et al., "Expression and Amplification of Engineered Mouse Dihydrofolate Reductase Minigenes", Molecular and Cellular Biology, vol. 3(2), pp. 257-266 (1983).

Cuozzo, J. et al., "Competition between glutathione and protein thiols for disulphide-bond formation", Nature Cell Biology, vol. 1, pp. 130-135 (1999).

Fiers, W. et al., "Complete nucleotide sequence of SV40 DNA", Nature, vol. 273, pp. 113-120 (1978).

Goldspiel, B. et al., "Human gene therapy", Clinical Pharmacy, vol. 12, pp. 488-505 (1993).

Goochee, C. et al., "The Oligosaccharides of Glycoproteins: Bioprocess Factors Affecting Oligosaccharide Structure and their effect on Glycoprotein Properties", Bio/Technol., vol. 9, pp. 1347-1356 (1991).

Graham, F. et al., "Characteristics of a Human Cell Line Transformed by DNA from Human Adenovirus Type 5", J. Gen. Virol., vol. 36, pp. 59-72 (1977).

Gramer, M. et al., "Glycosidase Activities in Chinese Hamster Ovary Cell Lysate and Cell Culture Supernatant", Biotechnol. Prog., vol. 9, pp. 366-373 (1993).

Gu, X. et al., "Site- and Branch-Specific Sialylation of Recombinant Human Interferon-γ in Chinese Hamster Ovary Cell Culture", Biotechnol. Bioeng., vol. 55(2), pp. 390-398 (1997).

Hansen, J. et al., "Monoclonal Antibodies Identifying a Novel T-Cell Antigen and Ia Antigens of Human Lymphocytes", Immunogenetics, vol. 10, pp. 247-260 (1980).

Hart, Gerald, "Glycosylation", Current Opinion in Cell Biology, vol. 4, pp. 1017-1023, (1992).

Haselbeck, A. et al., "Description and Application of an Immunological Detection System for Analyzing Glycoproteins on Blots", Glycoconjugate J., vol. 7, pp. 63-74 (1990).

Imai,Y. et al., "Sulphation requirement for GlyCAM-1, an endothelial ligand for L-selectin", Nature, vol. 361, pp. 555-557 (1993).

Jones, N. et al., "Isolation of complementary DNA clones encoding the human lymphocyte glycoprotein T1/Leu-1", Nature, vol. 323, pp. 346-349 (1986).

Karin, M. et al., "Human metallothionein genes-primary structure of the metallothionein-II gene and a related processed gene", Nature, vol. 299, pp. 797-802 (1982).

Kobata, A., "Structures and functions of the sugar chains of glycoproteins", Eur, J. Biochem., vol. 209, pp. 483-501 (1992).

Kolhekar, A., "Peptidylglycine α-Hydroxylating Monooxygenase: Active Site Residues, Disulfide Linkages, and a Two-Domain Model of the Catalytic Core", Biochemistry, vol. 36, pp. 10901-10909 (1997).

(56) References Cited

OTHER PUBLICATIONS

Lawson, E. et al., "Effect of Carbohydrate on Protein Solubility", Archives of Biochemistry and Biophysics, vol. 220(2), pp. 572-575 (1983).
Linsley, P. et al., "Human B7-1 (CD80) and B7-2 (CD86) Bind with Similar Avidities but Distinct Kinetics to CD28 and CTLA-4 Receptors", Immunity, vol. 1, pp. 793-801 (1994).
Lowy, I. et al., "Isolation of Transforming DNA: Cloning the Hamster aprt Gene", Cell, vol. 22, pp. 817-823 (1980).
Malik, N. et al., "Molecular Cloning, Sequence Analysis, and Functional Expression of a Novel Growth Regulator, Oncostatin M", Molecular and Cellular Biology, vol. 9(7), pp. 2847-2853 (1989).
Martin, P. et al., "Preincubation of Donor Bone Marrow Cells with a Combination of Murine Monoclonal Anti-T-Cell Antibodies Without Complement Does Not Prevent Graft-Versus-Host Disease After Allogeneic Marrow Transplantation", J. of Clinical Immunology, vol. 4(1), pp. 18-22 (1984).
Mather, J. et al., "Culture of Testicular Cells in Hormone-Supplemented Serum-Free Medium", Annals NY Academy Sci., vol. 383, pp. 44-68 (1982).
Mather, J., "Establishment and Characterization of Two Distinct Mouse Testicular Epithelial Cell Lines", Biology of Reproduction, vol. 23, pp. 243-252 (1980).
Morgan R. et al., "Human Gene Therapy", Annu. Rev. Biochem., vol. 62, pp. 191-217 (1993).
Mulligan, R.C. et al., "Selection for animal cells that express the *Escherichia coli* gene coding for xanthine-guanine phosphoribosyltransferase", PNAS, vol. 78(4), pp. 2072-2076 (1981).
Mulligan, R.C., "The Basic Science of Gene Therapy", Science, vol. 260, pp. 926-932 (1993).
Nelson, R. et al., "Higher-Affinity Oligosaccharide Ligands for E-Selectin", J. Clin. Invest., vol. 91, pp. 1157-1166 (1993).
Norgard, K. et al., "Enhanced interaction of L-selectin with the high endothelial venule ligand via selectively oxidized sialic acids", PNAS, vol. 90, pp. 1068-1072 (1993).
Oaks, M. et al., "A Native Soluble Form of CTLA-4", Cellular Immunology, vol. 201, pp. 144-153 (2000).
Ogawa, H. et al., "Determination of N-acetylneuraminic acid and N-glycolylneuraminic acid in glycoproteins by high-performance liquid chromatography without derivatization", Journal of Chromatography, vol. 612, pp. 145-149 (1993).
O'Hare, K. et al., "Transformation of mouse fibroblasts to methotrexate resistance by a recombinant plasmid expressing a prokaryotic dihydrofolate reductase", PNAS, vol. 78(3), pp. 1527-1531 (1981).
Parekh, R., "Mammalian cell gene expression: protein glycosylation", Current Opinion in Biotechnology, vol. 2, pp. 730-734 (1991).
Paulson, J., "Glycoproteins: what are the sugar chains for?", TIBS, vol. 14, pp. 272-276 (1989).
Peach, R. et al., "Complementarity Determining Region 1 (CDR1)- and CDR3- analogous Regions in CTLA-4 and CD28 Determine the Binding to B7-1", J. Exp. Med., vol. 180, pp. 2049-2058 (1994).
Robinson, C., "Gene therapy-proceeding from laboratory to clinic", Trends in Biotechnology, TIBTECH, vol. 11, p. 155 (1993).
Rössler, B. et al., "Temperature: A simple parameter for process optimization in fed-batch cultures of recombinant Chinese hamster ovary cells", Enzyme and Microbial Technology, vol. 18, pp. 423-427 (1996).
Santerre, R. et al., "Expression of prokaryotic genes for hygromycin B and G418 resistance as dominant-selection markers in mouse L cells", Gene, vol. 30, pp. 147-156 (1984).
Stephens, P.E. et al., "The construction of a highly efficient and versatile set of mammalian expression vectors", Nucleic Acids Research, vol. 17(17), p. 7110 (1989).
Subramani, S. et al., "Expression of the Mouse Dihydrofolate Reductase Complementary Deoxyribonucleic Acid in Simian Virus 40 Vectors", Molecular and Cellular Biology, vol. 1(9), pp. 854-864 (1981).
Swift, G. et al., "Tissue-Specific Expression of the Rat Pancreatic Elastase I Gene in Transgenic Mice", Cell, vol. 38, pp. 639-646 (1984).
Szybalska, E. et al., "Genetics of Human Cell Lines, IV. DNA-Mediated Heritable Transformation of a Biochemical Trait", PNAS, vol. 48, pp. 2026-2034 (1962).
Thomas, J. et al., "Aging and oxidation of reactive protein sulfhydryls", Experimental Gerontology, vol. 36, pp. 1519-1526 (2001).
Tolstoshev, P., "Gene Therapy, Concepts, Current Trials and Future Directions", Annu. Rev. Pharmacol. Toxicol., vol. 32, pp. 573-596 (1993).
Tsuda, E. et al., "The role of carbohydrate in recombinant human erythropoietin", Eur, J. Biochem., vol. 188, pp. 405-411 (1990).
Urlaub, G. et al., "Isolation of Chinese hamster cell mutants deficient in dihydrofolate reductase activity", PNAS, vol. 77(7), pp. 4216-4220 (1980).
Urlaub, G. et al., "Effect of Gamma Rays at the Dihydrofolate Reductase Locus: Deletions and Inversions", Somatic Cell and Molecular Genetics, vol. 12(6), pp. 555-566 (1986).
Varki, A., "Biological roles of oligosaccharides: all of the theories are correct", Glycobiology, vol. 3(2), pp. 97-130 (1993).
Warren, L., "The Thiobarbituric Acid Assay of Sialic Acids", The J. of Biological Chemistry, vol. 234(8), pp. 1971-1975 (1959).
Weikert, S. et al., "Engineering Chinese hamster ovary cells to maximize sialic acid content of recombinant glycoproteins", Nature Biotechnology, vol. 17, pp. 1116-1121 (1999).
Wigler, M. et al., "Transformation of mammalian cells with an amplifiable dominant-acting gene", PNAS, vol. 77(6), pp. 3567-3570 (1980).
Wigler, M. et al., "Transfer of Purified Herpes Virus Thymidine Kinase Gene to Cultured Mouse Cells", Cell, vol. 11, pp. 223-232 (1977).
Wittwer, A. et al., "Glycosylation at Asn-184 inhibits the Conversion of Single-Chain to Two-Chain Tissue-Type Plasminogen Activator by Plasmin", Biochemistry, vol. 29, pp. 4175-4180 (1990).
Wu, G. et al., "Delivery systems for gene therapy", Biotherapy, vol. 3, pp. 87-95 (1991).
Yao, K. et al., "Direct Determination of Bound Sialic Acids in Sialoglycoproteins by Acidic Ninhydrin Reaction", Analytical Biochemistry, vol. 179, pp. 332-225 (1989).
Yokochi, T. et al., "B Lymphoblast Antigen (BB-1) Expressed on Epstein-Barr Virus-Activated B Cell Blasts, B Lymphoblastoid Cell Lines, and Burkitt's Lymphomas", The J. of Immunology, vol. 128(2), pp. 823-827 (1982).
Zhang, X. et al., "Stable expression of human α-2, 6-sialyltransferase in Chinese hamster ovary cells: functional consequences for human erythropoietin expression and bioactivity", Biochimica et Biophysica Acta, vol. 1425, pp. 441-452 (1998).
Zanghi, J. et al., "The Growth Factor Inhibitor Suramin Reduces Apoptosis and Cell Aggregation in Protein-Free CHO Cell Batch Cultures", Biotechnol. Pro. vol. 16, pp. 319-325 (2000).
Yang, et al., "Fas and Activation-induced Fas Ligand Mediate Apoptosis of T Cell Hybridomas: Inhibition of Fas Ligand Expression by Retinoic Acid and Glucocorticoids", J. Exp. Med., vol. 181, pp. 1673-1682 (1995).
Xu, Song-mei, et al., "The High Level Expression of CTLA-4/Ig Fusion Protein in CHO Cell", Journal of Sichuan University, vol. 38, No. 3, p. 370-373, (2007).
Boshell, et al., "Effects of antigen presentation on superantigen-induced apoptosis mediated by Fas/Fas ligand interactions in human T cells", Immunology, 1996, vol. 87, pp. 586-592.
Mangalampalli, et al., "Increased production of a secreted glycoprotein in engineered CHO cells through amplification of a transcription factor", Cytotechnology, 2002, vol. 38, pp. 23-35.
U.S. Appl. No. 12/086,786, filed Jan. 27, 2009, Publication No. US 2009/0252749 A1, Kirk J., Leister, et al., Assignee: Bristol-Myers Squibb Company.

\* cited by examiner

A

B

A

B

A

B

A

B

A

B

Fig. 18 A/B
A
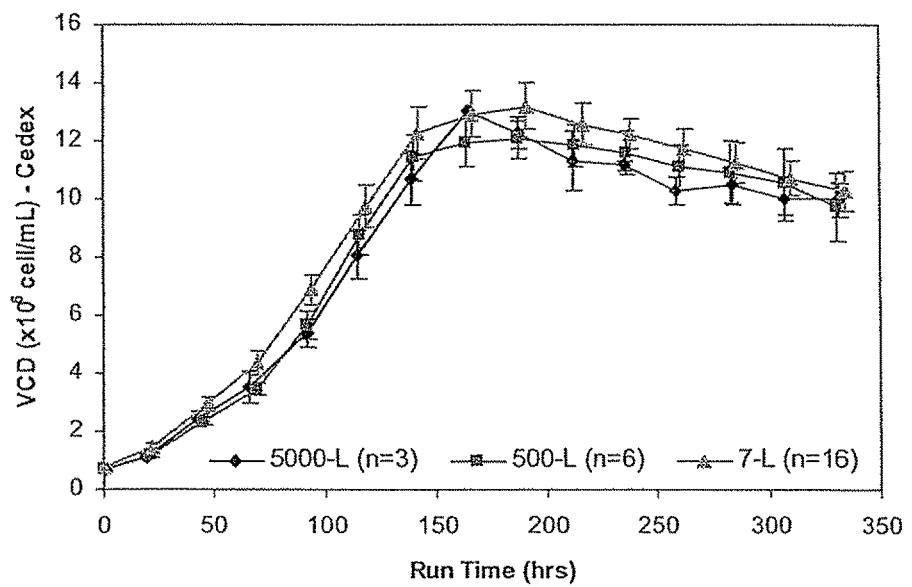
B
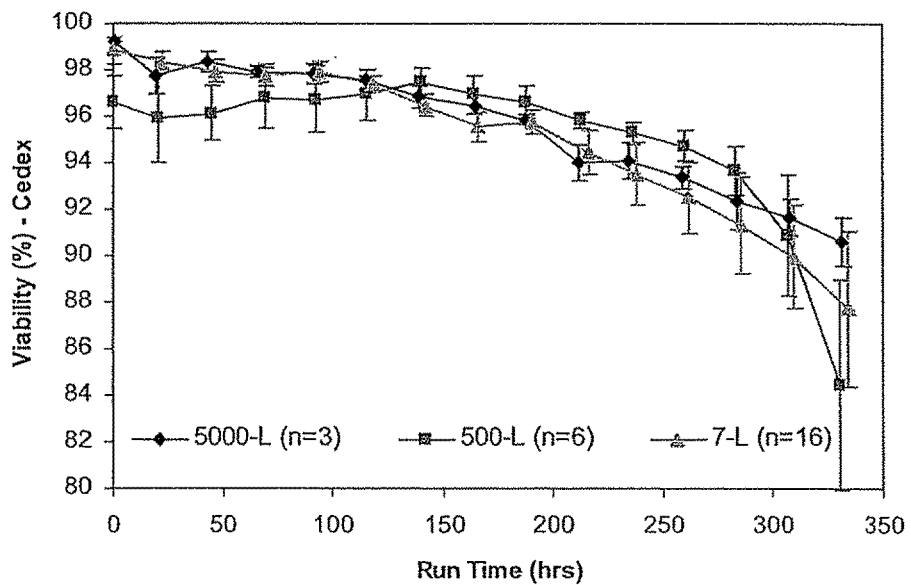

C
Fig. 18 C/D
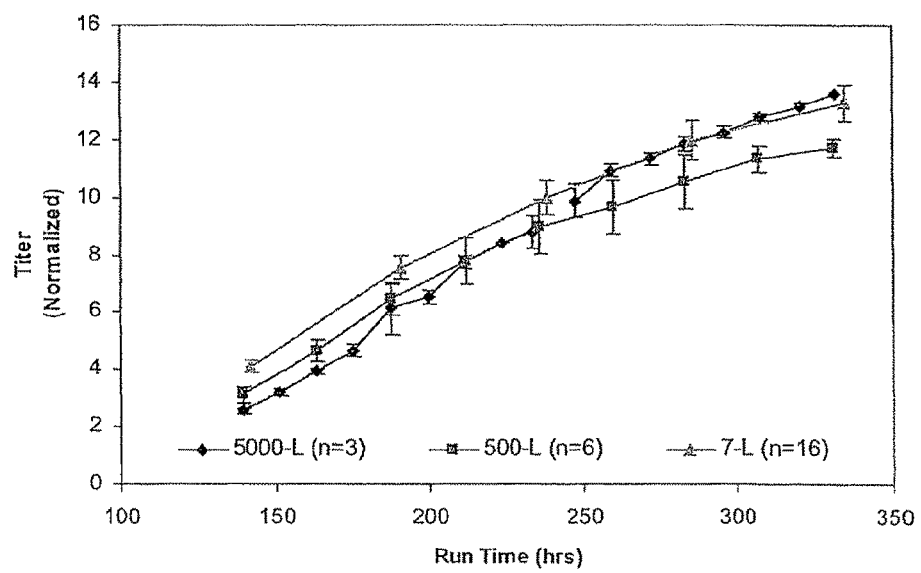
D
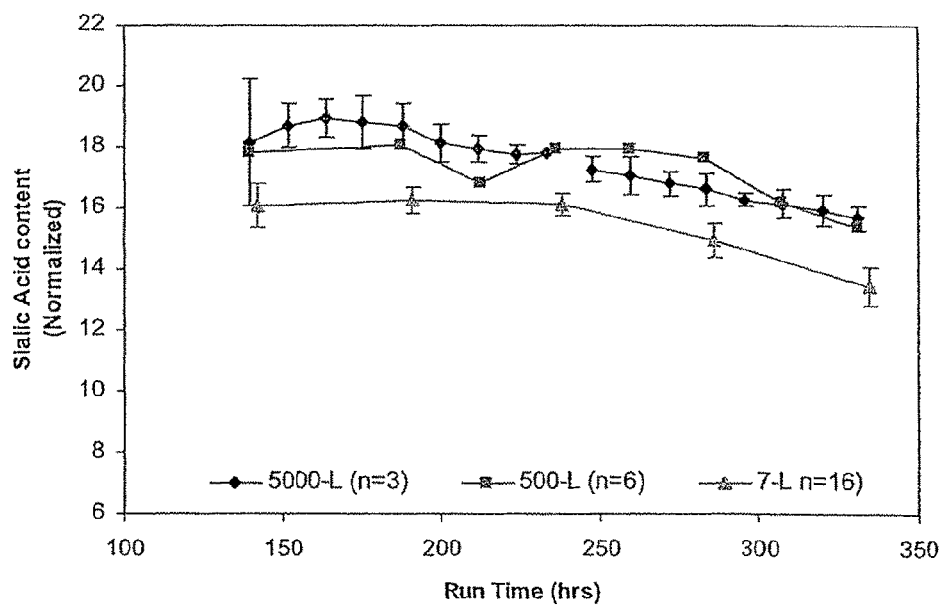

FIG. 19

```
ATGGGTGTACTGCTCACACAGAGGACGCTGCTCAGTCTGGTCCTTGCACTCCTGTTTCCA         -19
M---G---V---L---L---T---Q---R---T---L---L---S---L---V---L---A---L---L---F---P--   -7

AGCATGGCGAGCATGGCAATGCACGTGGCCCAGCCTGCTGTGGTACTGGCCAGCAGCCGA         +42
S---M---A---S---M---A---M---H---V---A---Q---P---A---V---V---L---A---S---S---R--   +14
                                                +1
GGCATCGCTAGCTTTGTGTGTGAGTATGCATCTCCAGGCAAAGCCACTGAGGTCCGGGTG         +102
G---I---A---S---F---V---C---E---Y---A---S---P---G---K---A---T---E---V---R---V--   +34

ACAGTGCTTCGGCAGGCTGACAGCCAGGTGACTGAAGTCTGTGCGGCAACCTACATGATG         +162
T---V---L---R---Q---A---D---S---Q---V---T---E---V---C---A---A---T---Y---M---M--   +54

GGGAATGAGTTGACCTTCCTAGATGATTCCATCTGCACGGGCACCTCCAGTGGAAATCAA         +222
G---N---E---L---T---F---L---D---D---S---I---C---T---G---T---S---S---G---N---Q--   +74

GTGAACCTCACTATCCAAGGACTGAGGGCCATGGACACGGGACTCTACATCTGCAAGGTG         +282
V---N---L---T---I---Q---G---L---R---A---M---D---T---G---L---Y---I---C---K---V--   +94

GAGCTCATGTACCCACCGCCATACTACCTGGGCATAGGCAACGGAACCCAGATTTATGTA         +342
E---L---M---Y---P---P---P---Y---Y---L---G---I---G---N---G---T---Q---I---Y---V--   +114

ATTGATCCAGAACCGTGCCCAGATTCTGATCAGGAGCCCAAATCTTCTGACAAAACTCAC         +402
I---D---P---E---P---C---P---D---S---D---Q---E---P---K---S---S---D---K---T---H--   +134

ACATCCCCACCGTCCCCAGCACCTGAACTCCTGGGTGGATCGTCAGTCTTCCTCTTCCCC         +462
T---S---P---P---S---P---A---P---E---L---L---G---G---S---S---V---F---L---F---P--   +154

CCAAAACCCAAGGACACCCTCATGATCTCCCGGACCCCTGAGGTCACATGCGTGGTGGTG         +522
P---K---P---K---D---T---L---M---I---S---R---T---P---E---V---T---C---V---V---V--   +174

GACGTGAGCCAGGAAGACCCTGAGGTCAAGTTCAACTGGTACGTGGACGGCGTGGAGGTG         +582
D---V---S---H---E---D---P---E---V---K---F---N---W---Y---V---D---G---V---E---V--   +194

CATAATGCCAAGACAAAGCCGCGGGAGGAGCAGTACAACAGCACGTACCGGGTGGTCAGC         +642
H---N---A---K---T---K---P---R---E---E---Q---Y---N---S---T---Y---R---V---V---S--   +214

GTCCTCACCGTCCTGCACCAGGACTGGCTGAATGGCAAGGAGTACAAGTGCAAGGTCTCC         +702
V---L---T---V---L---H---Q---D---W---L---N---G---K---E---Y---K---C---K---V---S--   +234

AACAAAGCCCTCCCAGCCCCCATCGAGAAAACCATCTCCAAAGCCAAAGGGCAGCCCCGA         +762
N---K---A---L---P---A---P---I---E---K---T---I---S---K---A---K---G---Q---P---R--   +254

GAACCACAGGTGTACACCCTGCCCCCATCCCGGGATGAGCTGACCAAGAACCAGGTCAGC         +822
E---P---Q---V---Y---T---L---P---P---S---R---D---E---L---T---K---N---Q---V---S--   +274

CTGACCTGCCTGGTCAAAGGCTTCTATCCCAGCGACATCGCCGTGGAGTGGGAGAGCAAT         +882
L---T---C---L---V---K---G---F---Y---P---S---D---I---A---V---E---W---E---S---N--   +294

GGGCAGCCGGAGAACAACTACAAGACCACGCCTCCCGTGCTGGACTCCGACGGCTCCTTC         +942
G---Q---P---E---N---N---Y---K---T---T---P---P---V---L---D---S---D---G---S---F--   +314

TTCCTCTACAGCAAGCTCACCGTGGACAAGAGCAGGTGGCAGCAGGGGAACGTCTTCTCA         +1002
F---L---Y---S---K---L---T---V---D---K---S---R---W---Q---Q---G---N---V---F---S--   +334

TGCTCCGTGATGCATGAGGCTCTGCACAACCACTACACGCAGAAGAGCCTCTCCCTGTCT         +1062
C---S---V---M---H---E---A---L---H---N---H---Y---T---Q---K---S---L---S---L---S--   +354

CCGGGTAAATGA
P---G---K---*
```

FIG. 20

```
ATGGGTGTACTGCTCACACAGAGGACGCTGCTCAGTCTGGTCCTTGCACTCCTGTTTCCA        -19
M--G--V--L--L--T--Q--R--T--L--L--S--L--V--L--A--L--L--F--P--        -7

AGCATGGCGAGCATGGCAATGCACGTGGCCCAGCCTGCTGTGGTACTGGCCAGCAGCCGA        +42
S--M--A--S--M--A--M--H--V--A--Q--P--A--V--V--L--A--S--S--R--        +14
                          +1

GGCATCGCTAGCTTTGTGTGTGAGTATGCATCTCCAGGCAAATATACTGAGGTCCGGGTG       +102
G--I--A--S--F--V--C--E--Y--A--S--P--G--K--Y--T--E--V--R--V--        +34

ACAGTGCTTCGGCAGGCTGACAGCCAGGTGACTGAAGTCTGTGCGGCAACCTACATGATG       +162
T--V--L--R--Q--A--D--S--Q--V--T--E--V--C--A--A--T--Y--M--M--        +54

GGGAATGAGTTGACCTTCCTAGATGATTCCATCTGCACGGGCACCTCCAGTGGAAATCAA       +222
G--N--E--L--T--F--L--D--D--S--I--C--T--G--T--S--S--G--N--Q--        +74

GTGAACCTCACTATCCAAGGACTGAGGGCCATGGACACGGGACTCTACATCTGCAAGGTG       +282
V--N--L--T--I--Q--G--L--R--A--M--D--T--G--L--Y--I--C--K--V--        +94

GAGCTCATGTACCCACCGCCATACTACGAGGGCATAGGCAACGGAACCCAGATTTATGTA       +342
E--L--M--Y--P--P--P--Y--Y--E--G--I--G--N--G--T--Q--I--Y--V--       +114

ATTGATCCAGAACCGTGCCCAGATTCTGATCAGGAGCCCAAATCTTCTGACAAAACTCAC       +402
I--D--P--E--P--C--P--D--S--D--Q--E--P--K--S--S--D--K--T--H--       +134

ACATCCCCACCGTCCCCAGCACCTGAACTCCTGGGGGGATCGTCAGTCTTCCTCTTCCCC       +462
T--S--P--P--S--P--A--P--E--L--L--G--G--S--S--V--F--L--F--P--       +154

CCAAAACCCAAGGACACCCTCATGATCTCCCGGACCCCTGAGGTCACATGCGTGGTGGTG       +522
P--K--P--K--D--T--L--M--I--S--R--T--P--E--V--T--C--V--V--V--       +174

GACGTGAGCCACGAAGACCCTGAGGTCAAGTTCAACTGGTACGTGGACGGCGTGGAGGTG       +582
D--V--S--H--E--D--P--E--V--K--F--N--W--Y--V--D--G--V--E--V--       +194

CATAATGCCAAGACAAAGCCGCGGGAGGAGCAGTACAACAGCACGTACCGTGTGGTCAGC       +642
H--N--A--K--T--K--P--R--E--E--Q--Y--N--S--T--Y--R--V--V--S--       +214

GTCCTCACCGTCCTGCACCAGGACTGGCTGAATGGCAAGGAGTACAAGTGCAAGGTCTCC       +702
V--L--T--V--L--H--Q--D--W--L--N--G--K--E--Y--K--C--K--V--S--       +234

AACAAAGCCCTCCCAGCCCCCATCGAGAAAACCATCTCCAAAGCCAAAGGGCAGCCCCGA       +762
N--K--A--L--P--A--P--I--E--K--T--I--S--K--A--K--G--Q--P--R--       +254

GAACCACAGGTGTACACCCTGCCCCCATCCCGGGATGAGCTGACCAAGAACCAGGTCAGC       +822
E--P--Q--V--Y--T--L--P--P--S--R--D--E--L--T--K--N--Q--V--S--       +274

CTGACCTGCCTGGTCAAAGGCTTCTATCCCAGCGACATCGCCGTGGAGTGGGAGAGCAAT       +882
L--T--C--L--V--K--G--F--Y--P--S--D--I--A--V--E--W--E--S--N--       +294

GGGCAGCCGGAGAACAACTACAAGACCACGCCTCCCGTGCTGGACTCCGACGGCTCCTTC       +942
G--Q--P--E--N--N--Y--K--T--T--P--P--V--L--D--S--D--G--S--F--       +314

TTCCTCTACAGCAAGCTCACCGTGGACAAGAGCAGGTGGCAGCAGGGGAACGTCTTCTCA      +1002
F--L--Y--S--K--L--T--V--D--K--S--R--W--Q--Q--G--N--V--F--S--       +334

TGCTCCGTGATGCATGAGGCTCTGCACAACCACTACACGCAGAAGAGCCTCTCCCTGTCT      +1062
C--S--V--M--H--E--A--L--H--N--H--Y--T--Q--K--S--L--S--L--S--       +354

CCGGGTAAATGA
P--G--K--*
```

FIG. 21

ONCOSTATIN M SIGNAL PEPTIDE

```
  M   G   V   L   L   T   Q   R   T   L   L   S   L   V   L
  ATG GGT GTA CTG CTC ACA CAG AGG ACG CTC CTC AGT CTG GTC CTT    45

-1  +1
  A   L   L   F   P   S   M   A   S   M   A   M   H   V   A
  GCA CTC CTG TTT CCA AGC ATG GCG AGC ATG GCA ATG CAC GTG GCC    90

Q   P   A   V   V   L   A   S   S   R   G   I   A   S   F
  CAG CCT GCT GTG GTA CTG GCC AGC AGC CGA GGC ATC GCC AGC TTT   135

V   C   E   Y   A   S   P   G   K   A   T   E   V   R   V
  GTG TGT GAG TAT GCA TCT CCA GGC AAA GCC ACT GAG GTC CGG GTG   180

T   V   L   R   Q   A   D   S   Q   V   T   E   V   C   A
  ACA GTG CTT CGG CAG GCT GAC AGC CAG GTG ACT GAA GTC TGT GCG   225

A   T   Y   M   M   G   N   E   L   T   F   L   D   D   S
  GCA ACC TAC ATG ATG GGG AAT GAG TTG ACC TTC CTA GAT GAT TCC   270

I   C   T   G   T   S   S   G   N   Q   V   N   L   T   I
  ATC TGC ACG GGC ACC TCC AGT GGA AAT CAA GTG AAC CTC ACT ATC   315

Q   G   L   R   A   M   D   T   G   L   Y   I   C   K   V
  CAA GGA CTG AGG GCC ATG GAC ACG GGA CTC TAC ATC TGC AAG GTG   360

GLYCOSYLATION SITE
  E   L   M   Y   P   P   P   Y   Y   L   G   I   G   N   G
  GAG CTC ATG TAC CCA CCG CCA TAC TAC CTG GGC ATA GGC AAC GGA   405

T   Q   I   Y   V   I   D   P   E   P   C   P   D   S   D
  ACC CAG ATT TAT GTA ATT GAT CCA GAA CCG TGC CCA GAT TCT GAC   450

F   L   L   W   I   L   A   A   V   S   S   G   L   F   F
  TTC CTC CTC TGG ATC CTT GCA GCA GTT AGT TCG GGG TTG TTT TTT   495

Y   S   F   L   L   T   A   V   S   L   S   K   M   L   K
  TAT AGC TTT CTC CTC AGA GCT GTT TCT TTG AGC AAA ATG CTA AAG   540

K   R   S   P   L   T   T   G   V   Y   V   K   M   P   P
  AAA AGA AGC CCT CTT ACA ACA GGG GTC TAT GTG AAA ATG CCC CCA   585

T   E   P   E   C   E   K   Q   F   Q   P   Y   F   I   P
  ACA GAG CCA GAA TGT GAA AAG CAA TTT CAG CCT TAT TTT ATT CCC   630

I   N
  ATC AAT                                                       636
```

MAMMALIAN CELL CULTURE PROCESSES FOR PROTEIN PRODUCTION

FIELD OF THE INVENTION

The present invention relates to new processes for culturing mammalian cells which produce a protein product, preferably a glycosylated protein product. Performance of the cell culturing processes result in high cell viability and can also result in high product quality and productivity, extension of the growth phase and reduction of death rate in the death phase.

BACKGROUND OF THE INVENTION

Animal cell culture, notably mammalian cell culture, is preferably used for the expression of recombinantly produced, glycosylated proteins for therapeutic and/or prophylactic applications. Glycosylation patterns of recombinant glycoproteins are important, because the oligosaccharide side chains of glycoproteins affect protein function, as well as the intramolecular interactions between different regions of a protein. Such intramolecular interactions are involved in protein conformation and tertiary structure of the glycoprotein. (See, e.g., A. Wittwer et al., 1990, *Biochemistry*, 29:4175-4180; Hart, 1992, *Curr. Op. Cell Biol.*, 4:1017-1023; Goochee et al., 1991, *Bio/Technol.*, 9:1347-1355; and R. B. Parekh, 1991, *Curr. Op. Struct. Biol.*, 1:750-754). In addition, oligosaccharides may function to target a particular polypeptide to certain structures based on specific cellular carbohydrate receptors. (M. P. Bevilacqua et al., 1993, *J. Clin. Invest.*, 91:379-387; R. M. Nelson et al., 1993, *J. Clin. Invest.*, 91:1157-1166; K. E. Norgard et al., 1993, *Proc. Natl. Acad. Sci. USA*, 90:1068-1072; and Y. Imai et al., 1993, *Nature*, 361-555-557).

The terminal sialic acid component of a glycoprotein oligosaccharide side chain is known to have an effect on numerous aspects and properties of a glycoprotein, including absorption, solubility, thermal stability, serum half life, clearance from the serum, as well as its physical and chemical structure/behavior and its immunogenicity. (A. Varki, 1993, *Glycobiology*, 3:97-100; R. B. Parekh, Id.; Goochee et al., Id., J. Paulson et al., 1989, *TIBS*, 14:272-276; and A. Kobata, 1992, *Eur. J. Biochem.*, 209:483-501; E. Q. Lawson et al., 1983, *Arch. Biochem. Biophys.*, 220:572-575; and E. Tsuda et al., 1990, *Eur. J. Biochem.*, 188:405-411).

The amount of sialic acid in glycoproteins is affected by two opposite processes: the intracellular additions of sialic acid by sialyltransferase activity and the extracellular removal of sialic acid by sialidase cleavage.

Intracellular addition of sialic acid is the last stage of the glycosylation process that takes place in the trans-Golgi. This involves the enzymatic transfer of sialic acid from the nucleotide sugar precursor, CMP-sialic acid to an available galactose on the emerging glycan structure that is attached to the newly synthesized protein. Possible limitations to the process that might cause incomplete sialylation include the availability of CMP-sialic acid, the activity of the sialyltransferase enzyme, the amount of the galactose on the emerging glycan structure and the activity of the galactosyltransferase enzyme. Significant amount of research has been focusing on maximizing sialylation through gene overexpression and enzyme activity enhancement of sialyltransferase and glycosyltransferase. Zhang et al. (Biochim Biophys Acta 1425(3):1998, 441-52) reported that expression of human α2,6-sialyltransferase in CHO cells with tissue plasminogen activator (tPA) production enhances the α2,6-sialylation of tPA. Weikert et al (Nat Biotechnol 17(11): 1999, 1116-21) reported that coexpression of α2,3-sialyltransferase and β1,4-galactosyltransferase results in greater than 90% sialylation of TNK-tPA and TNFR-IgG. Moreover, supplementation with the proper amount of manganese ($Mn^{2+}$), a cofactor for β1,4-galactosyltransferase, greatly reduced the amount of rHuEPO in the lower sialylated fraction, increased carbohydrate site occupancy and narrowed carbohydrate branching (Zhang et al. 1998) to bi-antennary structures in these lower sialylated species (Crowell et al. Biotechnol Bioeng 96(3):538-49, 2007).

The amount of sialic acid in glycoproteins is also affected by the extracellular removal of sialic acid by sialidase cleavage. Gramer and Goochee (Biotechnol Prog 9(4):366-73, 1993) have demonstrated an increase of lactate dehydrogenase (LDH), which signified an increase in the cell lysis, correlated with an increase of extracellular sialidase activity in CHO perfusion cultures. Gu et al (Biotechnol Bioeng 55(2):390-8, 1997) also illustrate a remarkable loss of terminal sialic acids of interferon-γ (IFN-γ) along with decrease in CHO cell viability and concomitant increase of dead cells throughout long-term batch cultivation.

Consequently, It is essential to delay the onset of cell death and improve cell viability to reduce or avoid this degradation effect In general, protein expression levels in mammalian cell culture-based systems are considerably lower than in microbial expression systems, for example, bacterial or yeast expression systems. However, bacterial and yeast cells are limited in their ability to optimally express high molecular weight protein products, to properly fold a protein having a complex steric structure, and/or to provide the necessary post-translational modifications to mature an expressed glycoprotein, thereby affecting the immunogenicity and clearance rate of the product.

As a consequence of the limitations of the culturing of animal or mammalian cells, particularly animal or mammalian cells which produce recombinant products, the manipulation of a variety of parameters has been investigated, including the employment of large-scale culture vessels; altering basic culture conditions, such as incubation temperature, dissolved oxygen concentration, pH, and the like; the use of different types of media and additives to the media; and increasing the density of the cultured cells. In addition, process development for mammalian cell culture would benefit from advances in the ability to extend run times to increase final product concentration while maintaining high product quality. An important product quality parameter is the degree and completeness of the glycosylation structure of a polypeptide product, with sialic acid content commonly used as a measure of glycoprotein quality.

Run times of cell culture processes, particularly non-continuous processes, are usually limited by the remaining viability of the cells, which typically declines over the course of the run. The maximum possible extension of high cell viabilities is therefore desired. Product quality concerns also offer a motivation for minimizing decreases in viable cell density and maintaining high cell viability, as cell death can release sialidases to the culture supernatant, which may reduce the sialic acid content of the protein expressed. Protein purification concerns offer yet another motivation for minimizing decreases in viable cell density and maintaining high cell viability. The presence of cell debris and the contents of dead cells in the culture can negatively impact on the ability to isolate and/or purify the protein product at the end of the culturing run. By keeping cells viable for a longer period of time in culture, there is thus a concomitant reduction in the contamination of the culture medium by cellular proteins and enzymes, e.g., cellular proteases and sialidases that can cause degradation and ultimate reduction in quality of the desired glycoprotein produced by the cells.

Various parameters have been investigated to achieve high cell viability in cell cultures. One parameter involved a single lowering of the culture temperature following initial culturing at 37° C. (for example, Roessler et al., 1996, *Enzyme and Microbial Technology*, 18:423-427; U.S. Pat. Nos. 5,705,364 and 5,721,121 to T. Etcheverry et al., 1998; U.S. Pat. No. 5,976,833 to K. Furukawa et al., 1999; U.S. Pat. No. 5,851,800 to L. Adamson et al.; WO 99/61650 and WO 00/65070 to Genentech, Inc.; WO 00/36092 to Biogen, Inc.; and U.S. Pat. No. 4,357,422 to Girard et al.).

Other parameters investigated involved the addition of components to the culture. The growth factor inhibitor suramin was shown to prevent apoptosis during exponential growth of CHO K1:CycE cells (Zhangi et al., *Biotechnol. Prog.* 2000, 16, 319-325). However, suramin did not protect against apoptosis during the death phase. As a result, suramin was capable of maintaining high viability during the growth phase, but did not allow for an extension of culture longevity. The same authors report that for the CHO 111-10 PF cell line, dextran sulfate and polyvinyl sulfate could, similarly to suramin, increase day 3 viable cell density and viability relative to the control culture. The effect of dextran sulfate or polyvinyl sulfate during the death phase was however not reported. Suramin, dextran sulfate and polyvinyl sulfate were also reported to be effective at preventing cell aggregation.

The effects of supplementing insect cell culture media with dexamethasone or N-acetylmannosamine on complex glycosylation of proteins, including the addition of terminal sialic acid residues to N-linked oligosaccharides, prepared via baculovirus expression vector system (BEVS) is disclosed in U.S. Pat. No. 6,472,175 to Boyce Thompson Institute For Plant Research, Inc. (Ithaca, N.Y.), 2002.

Protein therapeutics are inherently heterogeneous owing to their size, complexity of structure, and the nature of biological production (Chirino and Mire-Sluis, *Nat. Biotechnol.* 2004; 22:1383-1391). Even in the "pure" protein solution, there will be some percentage of low molecular weight fragments, high molecular weight species, and various degrees of chemical modifications. The formation of high molecular weight species is usually due to protein aggregation, which is a common issue encountered during manufacture of biologics. Typically, the presence of aggregates is considered to be undesirable because of the concern that the aggregates may lead to an immunogenic reaction or may cause adverse events on administration (Cromwell et al, *AAPS J.* 2006; 8:E572-579). Although some types of aggregates of biologics may function normally, it is still important to maintain consistency in product quality since product consistency is a prerequisite for regulatory approval.

Aggregates of proteins may arise from several mechanisms and occur at each stage during the manufacturing process. In cell culture, secreted proteins may be exposed to the conditions that are unfavorable for protein stability; but more often, accumulation of high amounts of protein may lead to intracellular aggregation owing to either the interactions of unfolded protein molecules or to inefficient recognition of the nascent peptide chain by molecular chaperones responsible for proper folding (Cromwell et al, *AAPS J.* 2006; 8:E572-579). In the endoplasmic reticulum (ER) of cells, disulfide bond of newly synthesized protein is formed in an oxidative environment. Under normal condition, protein sulfhydryls are reversibly oxidized to protein disulfides and sulfenic acids, but the more highly oxidized states such as the sulfinic and sulfonic acid forms of protein cysteines are irreversible (Thomas and Mallis, *Exp Gerontol.* 2001; 36:1519-1526). Hyper-oxidized proteins may contain incorrect disulfide bonds or have mixed disulfide bonds with other luminal ER proteins; in either case it leads to protein improper folding and aggregation. It is therefore crucial to maintain a properly controlled oxidative environment in the ER. In this regard, Cuozzo and Kaiser (*Nat Cell Biol.* 1999; 1:130-135) initially demonstrated that in yeasts glutathione buffered against ER hyperoxidation and later on Chakravarthi and Bulleid (*J Biol. Chem.* 2004; 279:39872-39879) confirmed that in mammalian cells glutathione was also required to regulate the formation of native disulfide bonds within proteins entering the secretory pathway.

With increasing product concentration in the culture, it can be observed in cell culture processes that the product quality decreases, as determined by the measured sialic acid content of the oligosaccharide glycostructure. Usually, a lower limit for an acceptable sialic acid content exists as determined by drug clearance studies. High abundance of a protein produced by cells in culture is optimally accompanied by high quality of the protein that is ultimately recovered for an intended use.

Recombinantly produced protein products that are properly glycosylated are increasingly becoming medically and clinically important for use as therapeutics, treatments and prophylactics. Therefore, the development of reliable cell culture processes that economically and efficiently achieve an increased final protein product concentration, in conjunction with a high level of product quality, such as is determined by sialic acid content, fulfills both a desired and needed goal in the art.

SUMMARY OF THE INVENTION

The present invention provides new processes for the production of proteins, preferably recombinant protein products, more preferably glycoprotein products, by animal or mammalian cell cultures. These new processes achieve increased viable cell density at the late phase, cell viability, productivity and sialic acid content and decreased protein aggregation.

One aspect of this invention concerns the addition of glucocorticoid to the media. In this aspect, cell culture processes of this invention can advantageously achieve an enhanced specific productivity, e.g., glycoprotein, as well as an enhanced sialic acid content of the glycoprotein produced by the cultured cells. More specifically, in accordance with this invention, addition of glucocorticoid during the cell culturing period sustains a high cell viability of the cells in the culture and can provide a high quantity and quality of produced product throughout an entire culture run. Also, according to one aspect of the invention, addition of glucocorticoid to the culturing processes can advantageously allow for an extension of the production phase of the culture. During the extended production phase, the titer of the desired product is increased; the product quality, as characterized by sialic acid content, is maintained at a high level; protein aggregation level is maintained at lower level and cell viability is also maintained at a high level. In addition, the extended production phase associated with the culturing processes of the invention allows for the production of product beyond that which is produced during a standard production phase.

In one particular aspect, the present invention provides a process (or method) in which the specific productivity is enhanced, the protein aggregation level was reduced and the sialic acid content of the produced glycoprotein is higher, by the addition of glucocorticoid. Glucocorticoid compound preferably is dexamethasone. In accordance with this particular aspect, the addition of glucocorticoid sustains a high cell viability of the culture, thereby enabling an extended production phase during which the titer of product, preferably recombinant product, is increased and the product quality, as characterized by sialic acid content, is maintained at high level. The addition of glucocorticoid can minimize the prevailing trade-off between protein titer and sialic acid content in the production of product during the cell culture process. Thus, the addition of glucocorticoid provides a positive effect on enhancing an important performance parameter of the culturing process, i.e., the mathematical product of "end (i.e., final) titer"×"end (i.e., final) sialic acid"×"monomer content"("end titer×end sialic acid"×"end monomer content).

In one aspect of this invention, glucocorticoid compound is added to a culture at the time of inoculation or at a time after inoculation that is before the beginning of the initial death phase, or is during the initial growth phase, or is during the second half of the initial growth phase, or is on or about the end of the initial growth phase. In accordance with this aspect of the invention, the growth phase is extended and/or the onset of the death phase is delayed for a period of time, such as several days.

In another preferred aspect of this invention and as further described herein, the newly developed cell culture processes involving the addition of a glucocorticoid compound, are especially suitable for the production of soluble CTLA4 molecules and soluble CTLA4 mutant molecule, such as CTLA4Ig and L104EA29YIg, by host cells genetically engineered to express and produce these proteins. Preferred embodiments of the present invention encompass the culturing of cells producing CTLA4Ig and L104EA29YIg involving the addition of a glucocorticoid compound during the culturing run to achieve large amounts of high quality CTLA4Ig and L104EA29YIg products, as determined by sialic acid measurement and/or low protein aggregation of the final products.

Further aspects, features and advantages of the present invention will be appreciated upon a reading of the detailed description of the invention and a consideration of the drawings/figures.

DESCRIPTION OF THE DRAWINGS/FIGURES

FIG. 1 shows the expressions of β1,4-galactosyltransferase (1A) and α2,3-sialyltransferase (1B) generally increase with dexamethasone (DEX) concentration in the DEX treated CHO cells as described in Example 1. DEX was added on the $2^{nd}$ day after inoculation to the cultures at concentrations from 0.1 to 10 10 µM. On the fifth day after inoculation, cell samples were collected and whole cell lysates were prepared, separated on a 4-15% gradient gel and probed with the antibody for each glycotransferase. The blot was then reprobed with the beta-actin antibody to assess equal loading.

FIG. 2 shows the cell protective effect of DEX resulting in reduced sialidase activity in the culture supernatant as described in Example 1. Cell viability (2A) and absorbance of supernatant sialidase activity assay (2B) profiles along the culture period between DEX treated and untreated cultures. DEX treatments at concentrations of 1 µM were initiated on day 2. Values reflect the mean and standard deviation of data from five experiments.

FIG. 3 shows improvements in glycoprotein sialylation in the cultures treated with glucocorticoid analogs, hydrocortisone (HYC) and prednisolone (PRD) as described in Example 1. Normalized total sialic acid content (3A) and normalized N-linked sialylated species fraction (3B) of cultures treated with DEX, HYC and PRD, respectively. Treatment was initiated on the second day after inoculation in a concentration of 0.1, 1 and 10 µM in the medium for each compound. Values of each parameter are reported as average±difference/2 (n=2)

FIG. 4 shows that the enhancement of sialylation by DEX was blocked by glucocorticoid antagonist RU-486 as described in Example 1. Normalized total sialic acid content (4A) and normalized N-linked sialylated species fraction (4B) in the presence and absence of RU-486. RU-486, at 0 or 1 µM, was introduced into cell culture suspension 48 hours after inoculation. 0.1, 1 and 10 µM of DEX was then added into the cultures 24 hours later. Values of each parameter are reported as average±difference/2 (n=2).

FIG. 5 shows that fed-batch cultures of DEX treated CHO cells in 5-L bioreactors resulted in increased sialic acid content and sialylated species fractions as described in Example 1. Normalized total sialic acid content (5A) and normalized N-linked sialylated species fraction (5B) of untreated and treated cultures throughout the cultivations. Values of each parameter are reported as average±standard deviation (n=3). The normalized value is the actual value divided by an arbitrary value.

FIG. 6 shows the capability of DEX to improve glycoprotein sialylation at 7, 10, and 20-L scale bioreactors as described in Example 1. Normalized final total sialic acid molar ratio versus normalized sialylated fraction of DEX treated and untreated cultures from different runs are summarized. The normalized value is the actual value divided by an arbitrary value.

FIG. 7 shows the reduced percentage of high molecular weight (HMW) species in the IgG-fusion proteins produced by CHO cells treated with dexamethasone (DEX) as described in Example 2. 7A, all cells were initially cultured together in the same shake flask for two days and then divided into two groups, with half of them receiving a single dose of DEX at the final concentration of 1 µM in basal medium. The supernatants were collected on Day 10 and purified before SEC-HPLC analysis to determine percentages of HMW species. Data points are means (±S.D.) of the results from five shake flasks in a single experiment. P<0.01 as compared to the control (CON). 7B, DEX at various concentrations was added to the CHO cell cultures on day 2 and supernatants were collected on day 10. Data points are means of the results obtained from duplicate flasks. 7C**, all the cultures were initiated at the same time, but 1 µM DEX was added on different day, giving different incubation time as indicated, when the cells were harvested at the same time on day 10. Data points are means of the results from duplicate flasks.

FIG. 8 shows the increased expression of glutathione reductase in the CHO cells treated with dexamethasone (DEX) as described in Example 2. DEX at various concentrations was added to the cell cultures on the inoculation day and cell samples were collected on day 5. Whole cell lysates were separated on a 4-15% gradient gel. After detection of glutathione reductase, the same blot was used to detect β-actin for sample loading comparison.

FIG. 9 shows the reduced percentage of HMW species in the IgG-fusion proteins incubated with GSH in vitro as described in Example 2. Reduced glutathione (GSH) at 0, 1 and 3 mM final concentrations was added to Tris-acetate buffered (pH 7.5) solution of purified IgG-fusion proteins, and the mixture of GSH and proteins was incubated at 37° C. for 1 h before SEC-HPLC analysis. Data points are means (±S.D.) of four determinations from two experiments. *P<0.05 as compared to the control (0 mM GSH).

FIG. 10 shows the attenuated effects of dexamethasone (DEX) in the presence of glucocorticoid receptor antagonist RU-486 as described in Example 2. 10A, whole cell lysates were prepared from untreated HepG-2 and CHO cells and separated on a 4-15% gradient gel. HepG-2 sample was used as human origin control for primary antibody validation purpose. 10B, RU-486 at 1 µM was introduced into the culture one day after the inoculation (day 1) and RU-486-pretreated CHO cells were divided on day 2, with half of them receiving a single dose of DEX at the final concentration of 0.1 µM in basal medium. Cell samples were collected on day 10; all the other procedures were the same as those in FIG. 2. 10C, RU-486 at 1 µM was introduced into the cultures on day 1 and DEX was then added to RU-486-pretreated cultures at the final concentration of either 0.1 µM or 1 µM on day 2. Supernatants were collected on day 10. Data points are means of the results from duplicate flasks.

FIG. 11 shows that cell death is inhibited by DEX in cultures of CHO cells in serum free medium as described in Example 3. Dose-response curves of the effect of DEX on viable cell density (11A) and viability (11B) with treatments initiated on day 2. Time-course curves of the effect of DEX on viable cell density (11C) and viability (11D) with 1 µM treatment concentration. Each value is the mean of data obtained from the experiments done in duplicate.

FIG. 12 shows CHO cell specific growth rate is reduced while cell specific productivity is increased by DEX as described in Example 3. The effects of DEX on CHO cell specific growth rate (12A), normalized volumetric productivity (12B) and normalized cell specific productivity (12B). DEX treatments were initiated on day 2. Values reflect the mean and standard deviation of data from five experiments. The normalized value is the actual value divided by an arbitrary value.

FIG. 13 shows the upregulation of anti-apoptotic gene GILZ in the DEX-treated CHO cells was confirmed by qRT-PCR and western blot analysis, as described in Example 3. (13A) DEX was added into the triplicate cultures on the $2^{nd}$ day after inoculation in the final concentration of 0 and 1 µM, respectively. mRNA samples was extracted on $5^{th}$ and $8^{th}$ after inoculation. Values of each parameter are reported as average±standard deviation (n=3). (13B) DEX was added into the triplicate cultures on the $2^{nd}$ day after inoculation in the final concentration of 0, and 1 µM, respectively. Cell samples were collected and whole cell lysates were prepared on $5^{th}$ and $8^{th}$ after inoculation.

FIG. 14 shows the death-suppression action of dexamethasone involves GILZ and glucocorticoid receptor, as described in Example 3 The percent increase (compared with no DEX treatment) of final viability (14A), the fold change of GILZ gene expression (14B) and GILZ protein expression induced by DEX (14C) in the presence and absence of RU-486. RU-486, at 0 or 1 µM, was introduced into cell culture suspension 48 hours after inoculation, 0, 0.1 and 1 µM of DEX was then added into the cultures 24 hours later. Cells were collected for viability, qRT-PCR and western blotting analysis. Each value reported in panel A is the mean of data obtained from the duplicate experiments. Each value reported in panel B is the mean and standard deviation of data obtained from the triplicate experiments.

FIG. 15 shows fed-batch cultures of DEX treated CHO cells in 10-L bioreactors result in an improved VCD, viability, titer and sialic acid molar ratio as described in Example 3. Viable cell density (15A), viability (15B) and normalized titer (15C) profiles of untreated culture and treated cultures with DEX treatment initiated on day 2 and day 7. The normalized value is the actual value divided by an arbitrary value.

FIG. 16 shows the effects of DEX on the cell growth of CHO cell culture with CTLA4Ig secretion. Dose-response curves of the effect of DEX on viable cell density (16A) and viability (16B) treated with DEX in the final concentration of 0, 0.001, 0.01, 0.1, 1 and 10 µM, respectively. Treatment was initiated on the second day after inoculation and each value is the mean of data obtained from the experiments done in duplicate.

FIG. 17 shows the effects of DEX on sialic acid molar ratio and HMW level of CTLA4Ig. The figure shows final total sialic acid molar ratio (17A) and HMW species (17B) of cultures treated with DEX in the final concentration of 0, 0.001, 0.01, 0.1, 1 and 10 µM, respectively. Treatment was initiated on the second day after inoculation and each value is the mean of data obtained from the experiments done in duplicate. Values reported in panel A are normalized values, which are the actual value divided by an arbitrary value.

FIG. 18 shows the feasibility of including DEX in the large scale recombinant glycoprotein production, as described in Example 5. The figure shows the viable cell density (18A), viability (18B), normalized titer (18C) and normalized sialic acid content (18D) of the recombinant glycoprotein produced at 7-L (n=16) and 500-L (n=6) and 5000-L (n=3) scales, respectively. Values reflect the mean and standard deviation of data from multiple experiments at each scale. The normalized value is the actual value divided by an arbitrary value. The same divisor was utilized for normalization in all scales.

FIG. 19 depicts a nucleotide sequence (SEQ ID NO:1) and encoded amino acid sequence (SEQ ID NO:2) of a CTLA4Ig having a signal peptide, a wild type amino acid sequence of the extracellular domain of CTLA4 starting at methionine at position +1 to aspartic acid at position +124, or starting at alanine at position −1 to aspartic acid at position +124, and an Ig region.

FIG. 20 depicts a nucleotide sequence (SEQ ID NO:3) and encoded amino acid sequence (SEQ ID NO:4) of a CTLA4 mutant molecule (L104EA29YIg) having a signal peptide, a mutated extracellular domain of CTLA4 starting at methionine at position +1 and ending at aspartic acid at position +124, or starting at alanine at position −1 and ending at aspartic acid at position +124, and an Ig region.

Figure 1:
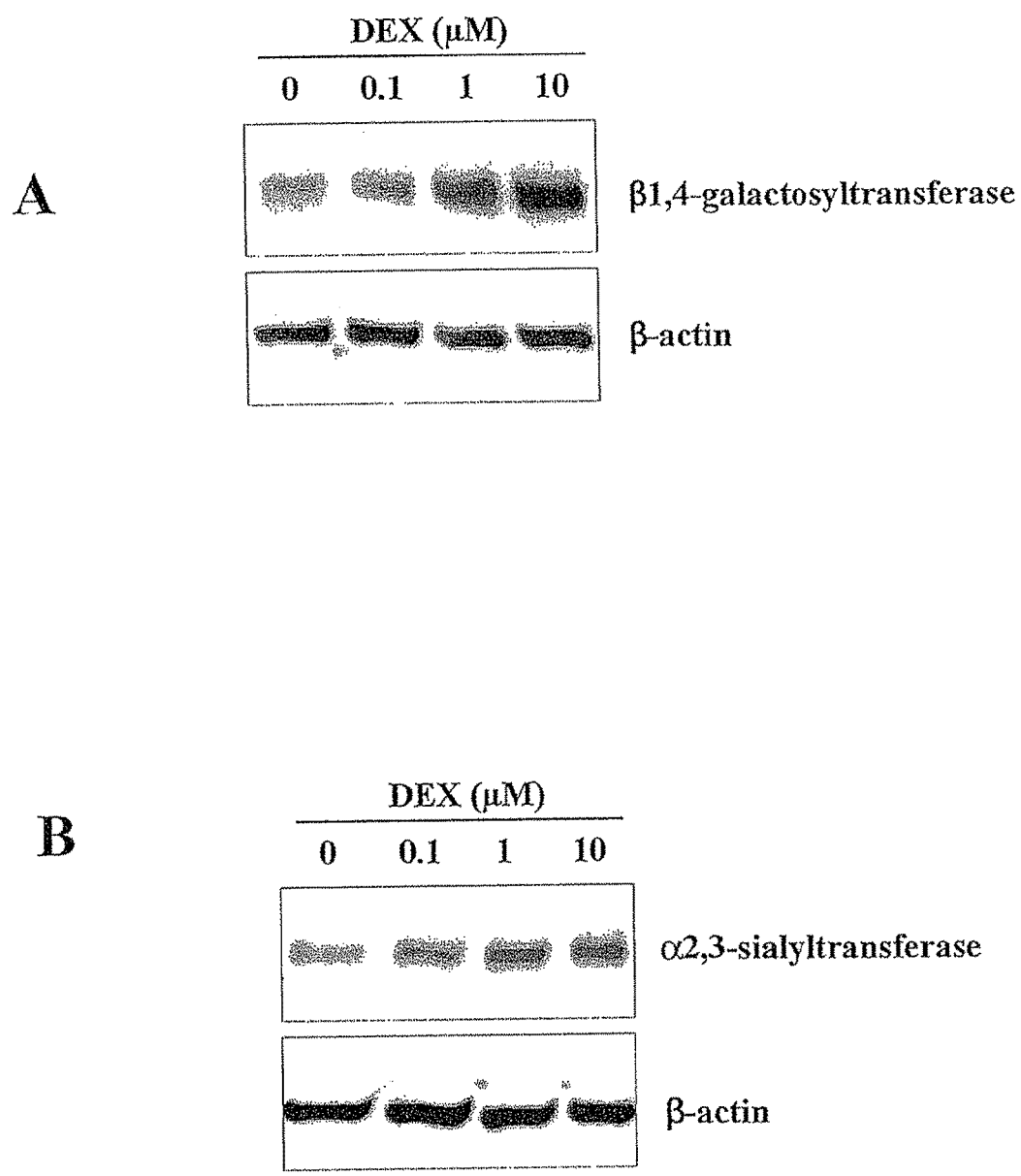

FIG. 21 depicts the nucleic acid sequence (SEQ ID NO:5) and encoded complete amino acid sequence (SEQ ID NO:6) of human CTLA4 receptor (referred to as "wild type" CTLA4 herein) fused to the oncostatin M signal peptide (position −26 to −2). (U.S. Pat. Nos. 5,434,131 and 5,844,095).

DETAILED DESCRIPTION OF THE INVENTION

The present invention describes new processes for the production of proteins, preferably recombinant protein products, more preferably glycoprotein products, in mammalian or animal cell culture. These processes achieve increased viable cell density, cell viability, productivity and sialic acid content and decreased protein aggregation.

In one embodiment, the invention is directed to a cell culturing process comprising: culturing host cells which express a protein of interest; and adding glucocorticoid compound to the cell culture.

Glucocorticoid compounds include, but are not limited to, hydrocortisone (available from Sigma-Aldrich, St. Louis, Mo.), prednisone (available from Sigma-Aldrich), prednisolone (available from Sigma-Aldrich), methylprednisolone (available from Sigma-Aldrich), dexamethasone (available from Sigma-Aldrich), betamethasone (available from Sigma-Aldrich), triamcinolone (available from Sigma-Aldrich), fludrocortisone acetate (available from Sigma-Aldrich). The compounds are readily available from the listed sources, or readily obtainable through means known to one of skill in the art.

Preferred glucocorticoid compounds include but not limited to hydrocortisone, prednisolone, betamethasone and dexamethasone. Most preferred is dexamethasone.

In one embodiment of the invention, glucocorticoid compound is added at inoculation or may be a component of the basal medium. Inoculation takes place on day 0.

In one embodiment of the invention, glucocorticoid compound is added at a time after inoculation, i.e. it is not present in the basal medium and not present at inoculation. Preferably, the glucocorticoid compound is added on day 1 of the culture or later In accordance with the invention, glucocorticoid compound may be added to the cell culture one time, two times, three times, or any number of times during the specified time period. One or more glucocorticoid compounds may be used in conjunction. That is, any given single addition of a glucocorticoid compound may include the addition of one or more other glucocorticoid compounds. Similarly, if there is more than one addition of a glucocorticoid compound, different glucocorticoid compounds may be added at the different additions. Additional compounds and substances, including glucocorticoid compounds, may be added to the culture before, with or after the addition of glucocorticoid compound—either during or not during the specified time period. In a preferred embodiment, there is a single, i.e. one time, addition of glucocorticoid compound. In a preferred embodiment, one glucocorticoid compound is added.

In accordance with the invention, glucocorticoid compound may be added to the cell culture by any means. Means of adding glucocorticoid compound include, but are not limited to, dissolved in DMSO, dissolved in organic solvent, dissolved in water, dissolved in culture medium, dissolved in feed medium, dissolved in a suitable medium, in the form in which it is obtained or any combination thereof.

Preferably, DEX is added as a solution where the DEX is dissolved in ethanol that is then diluted with water for further use (i.e. such as adding DEX to the feed medium).

In accordance with the invention, glucocorticoid compound is added to bring the concentration in the culture to an appropriate level. As non-limiting examples, glucocorticoid compound is added to a concentration of 1 nM-1 mM. Preferably glucocorticoid compound is added to a concentration of 1 nM-0.1 µM or 0.1 µM-10 µM; more preferably about 5 nM-15 nM or 0.5 µM-5 µM; more preferably about 10 nM or 1 µM target amounts.

In accordance with the invention, the culture may be run for any length of time after addition of glucocorticoid compound. The culture run time may be determined by one of skill in the art, based on relevant factors such as the quantity and quality of recoverable protein, and the level of contaminating cellular species (e.g. proteins and DNA) in the supernatant resulting from cell lysis, which will complicate recovery of the protein of interest.

In particular embodiments of the cell culturing process and method of increasing cell viability of the invention, glucocorticoid compound is added at a time after inoculation that is before the beginning of the initial death phase. Preferably, glucocorticoid compound is added at a time after inoculation that is during the initial growth phase. More preferably, glucocorticoid compound is added during the second half the initial growth phase. More preferably, glucocorticoid compound is added on or about the end of the initial growth phase.

The initial growth phase refers to the growth phase that is observed in the absence of the specified addition of glucocorticoid compound. The initial death phase refers to the death phase that is observed in the absence of the specified addition of glucocorticoid compound.

The initial growth phase may end when the initial death phase begins, or there may be a stationary phase of any length between the initial growth phase and the initial death phase.

For example, in a cell culture in which the initial growth phase is from day 0 to day 6 and the initial death phase begins on day 7, in a particular embodiment glucocorticoid compound is added at a time after inoculation and before day 7. In a specific embodiment, glucocorticoid compound is added after inoculation and by day 6. In a specific embodiment, glucocorticoid compound is added between days 1 and 6. In another specific embodiment, glucocorticoid compound is added with the feed medium on days 3-6. In other specific embodiments, glucocorticoid compound is added on about day 2, or on day 2.

It has been found (see Example 3) that when carrying the present invention the viability of the cell culture is prolonged. A condition, such as addition of glucocorticoid compound, causes prolonged cell viability if cell viability in the culture is higher for a period of time in the presence of the condition than in the absence of the condition.

Thus, in other embodiments, the invention is directed to (1) a cell culturing process, and (2) a method of prolonging cell viability in a culture comprising: culturing host cells which express a protein of interest; and adding glucocorticoid compound to the cell culture; wherein the cell viability of the cell culture is prolonged.

It has been found (see Example 3), that when glucocorticoid compound is added at a time after inoculation and before the beginning of the initial death phase, the death rate of the death phase may be reduced, less than that of the death phase observed in the absence of the addition of glucocorticoid compound.

Thus, in other embodiments, the invention is directed to (1) a cell culturing process, and (2) a process for reducing the death rate of the death phase of a cell culture comprising: culturing host cells which express a protein of interest; and adding glucocorticoid compound to the cell culture at a time after inoculation that is before the beginning of the initial death phase; wherein the death rate of the death phase is reduced. In more particular embodiments, the invention is directed to (1) a cell culturing process, and (2) a process for reducing the death rate of the death phase of a cell culture comprising: culturing host cells which express a protein of interest; and adding glucocorticoid compound to the cell culture at a time after inoculation that is during the initial growth phase; wherein the death rate of the death phase is delayed. In more particular embodiments the invention is directed to (1) a cell culturing process, and (2) a process for reducing the death rate of the death phase of a cell culture comprising: culturing host cells which express a protein of interest; and adding glucocorticoid compound to the cell culture during the second half of the initial growth phase; wherein the death rate of the death phase is reduced. In other particular embodiments the invention is directed to a process for reducing the death rate of the death phase of a cell culture comprising: culturing host cells which express a protein of interest; and adding glucocorticoid compound to the cell culture on or about the end of the initial growth phase; wherein the death rate of the death phase is delayed.

Example 3 also demonstrates that hydrocortisone (HYC), prednisolone (PRD) and dexamethasone (DEX) all show a dose-dependent cell protective effect in treated cell cultures when compared with untreated cell cultures. However, higher concentrations of HYC and PRD was required to achieve the same level of cell protective effect, which is consistent with their potency differences (i.e. HYC and PRD are only 5% and 20% as potent as DEX)

Run times of cell culture processes, particularly non-continuous processes, are usually limited by the remaining viable cell density, which decreases during the death phase. Longer run times may allow higher product titers to be achieved. Product quality concerns also offer a motivation for reducing death rate, as cell death can release sialidases to the culture supernatant, which may reduce the sialic acid content of the protein expressed. Protein purification concerns offer yet another motivation for delaying or arresting the death phase. The presence of cell debris and the contents of dead cells in the culture can negatively impact on the ability to isolate and/or purify the protein product at the end of the culturing run.

It has been found (see Example 2), that addition of glucocorticoid compound to the cell culture reduces the aggregation of the proteins of interest.

Thus, in other embodiments, the invention is directed to (1) a cell culturing process, and (2) a process for reducing the percentage of protein aggregation comprising: culturing host cells which express a protein of interest; and adding glucocorticoid compound to the cell culture; wherein the percentage of high molecular weight species is decreased.

It has been found (see Example 1), that addition of glucocorticoid compound to the cell culture improves sialylation of the proteins of interest by enhancing total sialic acid content and increasing percentage of sialylated species.

Example 1 also demonstrates that hydrocortisone (HYC), prednisolone (PRD) and dexamethasone (DEX) all show a dose-dependent sialylation improvement in treated cell cultures when compared with untreated cell cultures. However, a higher concentration of HYC and PRD was required to achieve the same level of improvement, which is consistent with their potency differences.

Thus, in other embodiments, the invention is directed to (1) a cell culturing process, and (2) a process for increasing the percentage of sialylated species comprising: culturing host cells which express a protein of interest; and adding glucocorticoid compound to the cell culture; wherein the percentage of sialylated species is increased.

Thus, in other embodiments, the invention is directed to (1) a cell culturing process, and (2) a process for increasing total sialic acid content comprising: culturing host cells which express a glycoprotein of interest; and adding glucocorticoid compound to the cell culture; wherein the total sialic acid content is increased.

Thus, in other embodiments, the invention is directed to (1) a cell culturing process, and (2) a process for reducing de-sialylation rate of glycoproteins in cell culture comprising: culturing host cells which express a glycoprotein of interest; and adding glucocorticoid compound to the cell culture; wherein the de-sialylation rate is decreased.

Techniques and Procedures Relating to Glycoprotein Purification and Analysis

In the culturing methods encompassed by the present invention, the protein produced by the cells is typically collected, recovered, isolated, and/or purified, or substantially purified, as desired, at the end of the total cell culture period using isolation and purification methods as known and practiced in the art. Preferably, protein that is secreted from the cultured cells is isolated from the culture medium or supernatant; however, protein can also be recovered from the host cells, e.g., cell lysates, using methods that are known and practiced in the art, and as further described below.

The complex carbohydrate comprising the glycoprotein produced by the processes of this invention can be routinely analyzed, if desired, by conventional techniques of carbohydrate analysis. For example, techniques such as lectin blotting, well-known in the art, reveal proportions of terminal mannose, or other sugars such as galactose. Termination of mono-, bi-, tri-, or tetra-antennary oligosaccharide by sialic acids can be confirmed by release of sugars from the protein using anhydrous hydrazine or enzymatic methods and fractionation of oligosaccharides by ion-exchange chromatography, size exclusion chromatography, or other methods that are well-known in the art.

The pI of the glycoprotein can also be measured, before and after treatment with neuraminidase, to remove sialic acids. An increase in pI following neuraminidase treatment indicates the presence of sialic acids on the glycoprotein. Carbohydrate structures typically occur on the expressed protein as N-linked or O-linked carbohydrates. The N-linked and O-linked carbohydrates differ primarily in their core structures. N-linked glycosylation refers to the attachment of the carbohydrate moiety via GlcNAc to an asparagine residue in the peptide chain. The N-linked carbohydrates all contain a common Man1-6(Man1-3)Manβ1-4GlcNAcβ1-4GlcNAcβ-R core structure, where R in this core structure represents an asparagine residue. The peptide sequence of the protein produced will contain an asparagine-X-serine, asparagine-X-threonine, and asparagine-X-cysteine, wherein X is any amino acid except proline.

In contrast, O-linked carbohydrates are characterized by a common core structure, which is GalNAc attached to the hydroxyl group of a threonine or serine. Of the N-linked and O-linked carbohydrates, the most important are the complex N- and O-linked carbohydrates. Such complex carbohydrates contain several antennary structures. The mono-, bi-, tri-, and tetra-, outer structures are important for the addition of terminal sialic acids. Such outer chain structures provide for additional sites for the specific sugars and linkages that comprise the carbohydrates of the protein products.

The resulting carbohydrates can be analyzed by any method known in the art. Several methods are known in the art for glycosylation analysis and are useful in the context of the present invention. These methods provide information regarding the identity and the composition of the oligosaccharide attached to the produced peptide. Methods for carbohydrate analysis useful in connection with the present invention include, but are not limited to, lectin chromatography; HPAEC-PAD, which uses high pH anion exchange chromatography to separate oligosaccharides based on charge; NMR; Mass spectrometry; HPLC; GPC; monosaccharide compositional analysis; and sequential enzymatic digestion.

In addition, methods for releasing oligosaccharides are known and practiced in the art. These methods include 1) enzymatic methods, which are commonly performed using peptide-N-glycosidase F/endo-β-galactosidase; 2) β elimination methods, using a harsh alkaline environment to release mainly O-linked structures; and 3) chemical methods using anhydrous hydrazine to release both N- and O-linked oligosaccharides. Analysis can be performed using the following steps: 1. Dialysis of the sample against deionized water to remove all buffer salts, followed by lyophilization. 2. Release of intact oligosaccharide chains with anhydrous hydrazine. 3. Treatment of the intact oligosaccharide chains with anhydrous methanolic HCl to liberate individual monosaccharides as O-methyl derivatives. 4. N-acetylation of any primary amino groups. 5. Derivatization to yield per-O-trimethylsilyl methyl glycosides. 6. Separation of these derivatives by capillary gas-liquid chromatography (GLC) on a CP-SIL8 column. 7. Identification of individual glycoside derivatives by retention time from the GLC and mass spectroscopy, compared to known standards. 8. Quantification of individual derivatives by FID with an internal standard (13-O-methyl-D-glucose).

Neutral and amino sugars can be determined by high performance anion-exchange chromatography combined with pulsed amperometric detection (HPAE-PAD Carbohydrate System; Dionex Corp.). For instance, sugars can be released by hydrolysis in 20% (v/v) trifluoroacetic acid at 100° C. for 6 hours. Hydrolysates are then dried by lyophilization or with a Speed-Vac (Savant Instruments). Residues are then dissolved in 1% sodium acetate trihydrate solution and analyzed on an HPLC-AS6 column (as described by Anumula et al., 1991, *Anal. Biochem.,* 195: 269-280).

Alternatively, immunoblot carbohydrate analysis can be performed. In this procedure protein-bound carbohydrates are detected using a commercial glycan detection system (Boehringer), which is based on the oxidative immunoblot procedure described by Haselbeck et al. (1993, *Glycoconjugate J.,* 7:63). The staining protocol recommended by the manufacturer is followed except that the protein is transferred to a polyvinylidene difluoride membrane instead of a nitrocellulose membrane and the blocking buffers contain 5% bovine serum albumin in 10 mM Tris buffer, pH 7.4, with 0.9% sodium chloride. Detection is carried out with anti-digoxigenin antibodies linked with an alkaline phosphate conjugate (Boehringer), 1:1000 dilution in Tris buffered saline using the phosphatase substrates, 4-nitroblue tetrazolium chloride, 0.03% (w/v) and 5-bromo-4 chloro-3-indoyl-phosphate 0.03% (w/v) in 100 mM Tris buffer, pH 9.5, containing 100 mM sodium chloride and 50 mM magnesium chloride. The protein bands containing carbohydrate are usually visualized in about 10 to 15 minutes.

Carbohydrate associated with protein can also be analyzed by digestion with peptide-N-glycosidase F. According to this procedure the residue is suspended in 14 μL of a buffer containing 0.18% SDS, 18 mM beta-mercaptoethanol, 90 mM phosphate, 3.6 mM EDTA, at pH 8.6, and heated at 100° C. for 3 minutes. After cooling to room temperature, the sample is divided into two equal parts. One part, which is not treated further, serves as a control. The other part is adjusted to about 1% NP-40 detergent followed by the addition of 0.2 units of peptide-N-glycosidase F (Boehringer). Both samples are warmed at 37° C. for 2 hours and then analyzed by SDS-polyacrylamide gel electrophoresis.

In addition, the sialic acid content of the glycoprotein product is assessed by conventional methods. For example, sialic acid can be separately determined by a direct colorimetric method (Yao et al., 1989, *Anal. Biochem.,* 179:332-335), preferably using triplicate samples. Another method of sialic acid determination involves the use of thiobarbaturic acid (TBA), as described by Warren et al.(1959, *J. Biol. Chem.,* 234:1971-1975). Yet another method involves high performance chromatography, such as described by H. K. Ogawa et al. (1993, *J. Chromatography,* 612:145-149).

Illustratively, for glycoprotein recovery, isolation and/or purification, the cell culture medium or cell lysate is centrifuged to remove particulate cells and cell debris. The desired polypeptide product is isolated or purified away from contaminating soluble proteins and polypeptides by suitable purification techniques. The following procedures provide exemplary, yet nonlimiting purification methods for proteins: separation or fractionation on immunoaffinity or ion-exchange columns; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. It will be understood by the skilled practitioner that purification methods for a given polypeptide of interest may require modifications which allow for changes in the polypeptide expressed recombinantly in cell culture. Those purification procedures that can select for carbohydrates and enrich for sialic acid are particularly preferred, e.g., ion-exchange soft gel chromatography, or HPLC using cation- or anion-exchange resins, in which the more acidic fraction(s) is/are collected.

Cells, Proteins and Cell Cultures

In the cell culture processes or methods of this invention, the cells can be maintained in a variety of cell culture media. i.e., basal culture media, as conventionally known in the art. For example, the methods are applicable for use with large volumes of cells maintained in cell culture medium, which can be supplemented with nutrients and the like. Typically, "cell culturing medium" (also called "culture medium") is a term that is understood by the practitioner in the art and is known to refer to a nutrient solution in which cells, preferably animal or mammalian cells, are grown and which generally provides at least one or more components from the following: an energy source (usually in the form of a carbohydrate such as glucose); all essential amino acids, and generally the twenty basic amino acids, plus cysteine; vitamins and/or other organic compounds typically required at low concentrations; lipids or free fatty acids, e.g., linoleic acid; and trace elements, e.g., inorganic compounds or naturally occurring elements that are typically required at very low concentrations, usually in the micromolar range. Cell culture medium can also be supplemented to contain a variety of optional components, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal protein (peptone or peptone mixtures, which can be obtained from animal byproducts, purified gelatin or plant material); antibiotics, e.g., gentamycin; and cell protective agents, e.g., a Pluronic polyol (Pluronic F68). Preferred is a cell nutrition medium that is serum-free and free of products or ingredients of animal origin.

As is appreciated by the practitioner, animal or mammalian cells are cultured in a medium suitable for the particular cells being cultured and which can be determined by the person of skill in the art without undue experimentation. Commercially available media can be utilized and include, for example, Minimal Essential Medium (MEM, Sigma, St. Louis, Mo.); Ham's F10 Medium (Sigma); Dulbecco's Modified Eagles Medium (DMEM, Sigma); RPM I-1640 Medium (Sigma); HyClone cell culture medium (HyClone, Logan, Utah); and chemically-defined (CD) media, which are formulated for particular cell types, e.g., CD-CHO Medium (Invitrogen, Carlsbad, Calif.). To the foregoing exemplary media can be added the above-described supplementary components or ingredients, including optional components, in appropriate concentrations or amounts, as necessary or desired, and as would be known and practiced by those having in the art using routine skill.

In addition, cell culture conditions suitable for the methods of the present invention are those that are typically employed and known for batch, fed-batch, or continuous culturing of cells, with attention paid to pH, e.g., about 6.5 to about 7.5; dissolved oxygen ($O_2$), e.g., between about 5-90% of air saturation and carbon dioxide ($CO_2$), agitation and humidity, in addition to temperature. As an illustrative, yet nonlimiting, example, a suitable cell culturing medium for the fed-batch processes of the present invention comprises a modified CD-CHO Medium (Invitrogen, Carlsbad, Calif.). A feeding medium can also be employed, such as modified eRDF medium (Invitrogen, Carlsbad, Calif.). Preferred is a feeding medium also containing glucocorticoid, e.g. dexamethasone.

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or growth factors. Growth factors and nutrients that are necessary for the growth and maintenance of particular cell cultures are able to be readily determined empirically by those having skill in the pertinent art, such as is described, for example, by Barnes and Sato, (1980, *Cell*, 22:649); in *Mammalian Cell Culture*, Ed. J.P. Mather, Plenum Press, NY, 1984; and in U.S. Pat. No. 5,721,121.

Numerous types of cells can be cultured according to the methods of the present invention. The cells are typically animal or mammalian cells that can express and secrete, or that can be molecularly engineered to express and secrete, large quantities of a particular protein, more particularly, a glycoprotein of interest, into the culture medium. It will be understood that the glycoprotein produced by a host cell can be endogenous or homologous to the host cell. Alternatively, and preferably, the glycoprotein is heterologous, i.e., foreign, to the host cell, for example, a human glycoprotein produced and secreted by a Chinese hamster ovary (CHO) host cell. Also preferably, mammalian glycoproteins, i.e., those originally obtained or derived from a mammalian organism, are attained by the methods the present invention and are preferably secreted by the cells into the culture medium.

Examples of mammalian glycoproteins that can be advantageously produced by the methods of this invention include, without limitation, cytokines, cytokine receptors, growth factors (e.g., EGF, HER-2, FGF-α, FGF-β, TGF-α, TGF-β, PDGF, IGF-1, IGF-2, NGF, NGF-β); growth factor receptors, including fusion or chimeric proteins. Other nonlimiting examples include growth hormones (e.g., human growth hormone, bovine growth hormone); insulin (e.g., insulin A chain and insulin B chain), proinsulin; erythropoietin (EPO); colony stimulating factors (e.g., G-CSF, GM-CSF, M-CSF); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; follicle stimulating hormone (FSH); luteinizing hormone (LH); calcitonin; CD proteins (e.g., CD3, CD4, CD8, CD28, CD19, etc.); CTLA proteins (e.g., CTLA4); T-cell and B-cell receptor proteins; bone morphogenic proteins (BNPs, e.g., BMP-1, BMP-2, BMP-3, etc.); neurotrophic factors, e.g., bone derived neurotrophic factor (BDNF); neurotrophins, e.g., 3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art. Fusion proteins and polypeptides, chimeric proteins and polypeptides, as well as fragments or portions, or mutants, variants, or analogues of any of the aforementioned proteins and polypeptides are also included among the suitable proteins, polypeptides and peptides that can be produced by the methods of the present invention.

Nonlimiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, *Som. Cell Molec. Genet.*, 12:555-556; and Kolkekar et al., 1997, *Biochemistry*, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, *Proc. Natl. Acad. Sci. USA*, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TR1 cells (Mather, 1982, *Annals NY Acad. Sci.*, 383:44-68); MCR 5 cells; FS4 cells. Preferred are CHO cells, particularly, CHO/-DHFR cells.

The cells suitable for culturing in the methods and processes of the present invention can contain introduced, e.g., via transformation, transfection, infection, or injection, expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

Control elements, or regulatory sequences, are those non-translated regions of the vector, e.g., enhancers, promoters, 5' and 3' untranslated regions, that interact with host cellular proteins to carry out transcription and translation. Such elements can vary in their strength and specificity. Depending on the vector system and host cell utilized, any number of suitable transcription and translation elements, including constitutive and inducible promoters, can be used. In mammalian cell systems, promoters from mammalian genes or from mammalian viruses are preferred. The constructs for use in protein expression systems are designed to contain at least one promoter, an enhancer sequence (optional, for mammalian expression systems), and other sequences as necessary or required for proper transcription and regulation of gene expression (e.g., transcriptional initiation and termination sequences, origin of replication sites, polyadenylation sequences, e.g., the Bovine Growth Hormone (BGH) poly A sequence).

As will be appreciated by those skilled in the art, the selection of the appropriate vector, e.g., plasmid, components for proper transcription, expression, and isolation of proteins produced in eukaryotic (e.g., mammalian) expression systems is known and routinely determined and practiced by those having skill in the art. The expression of proteins by the cells cultured in accordance with the methods of this invention can placed under the control of promoters such as viral promoters, e.g., cytomegalovirus (CMV), Rous sarcoma virus (RSV), phosphoglycerol kinase (PGK), thymidine kinase (TK), or the α-actin promoter. Further, regulated promoters confer inducibility by particular compounds or molecules, e.g., the glucocorticoid response element (GRE) of mouse mammary tumor virus (M MTV) is induced by glucocorticoids (V. Chandler et al., 1983, *Cell*, 33:489-499). Also, tissue-specific promoters or regulatory elements can be used (G. Swift et al., 1984, *Cell*, 38:639-646), if necessary or desired.

Expression constructs can be introduced into cells by a variety of gene transfer methods known to those skilled in the art, for example, conventional gene transfection methods, such as calcium phosphate co-precipitation, liposomal transfection, microinjection, electroporation, and infection or viral transduction. The choice of the method is within the competence of the skilled practitioner in the art. It will be apparent to those skilled in the art that one or more constructs carrying DNA sequences for expression in cells can be transfected into the cells such that expression products are subsequently produced in and/or obtained from the cells.

In a particular aspect, mammalian expression systems containing appropriate control and regulatory sequences are preferred for use in protein expressing mammalian cells of the present invention. Commonly used eukaryotic control sequences for use in mammalian expression vectors include promoters and control sequences compatible with mammalian cells such as, for example, the cytomegalovirus (CMV) promoter (CDM8 vector) and avian sarcoma virus (ASV), (mLN). Other commonly used promoters include the early and late promoters from Simian Virus 40 (SV40) (Fiers et al., 1973, *Nature*, 273:113), or other viral promoters such as those derived from polyoma, Adenovirus 2, and bovine papilloma virus. An inducible promoter, such as hMTII (Karin et al., 1982, *Nature*, 299:797-802) can also be used.

Examples of expression vectors suitable for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene), retroviral vectors (e.g., pFB vectors (Stratagene)), pcDNA-3 (Invitrogen), adenoviral vectors; Adeno-associated virus vectors, baculovirus vectors, yeast vectors (e.g., pESC vectors (Stratagene)), or modified forms of any of the foregoing. Vectors can also contain enhancer sequences upstream or downstream of promoter region sequences for optimizing gene expression.

A selectable marker can also be used in a recombinant vector (e.g., a plasmid) to confer resistance to the cells harboring (preferably, having stably integrated) the vector to allow their selection in appropriate selection medium. A number of selection systems can be used, including but not limited to, the Herpes Simplex Virus thymidine kinase (HSV TK), (Wigler et al., 1977, *Cell*, 11:223), hypoxanthine-guanine phosphoribosyltransferase (HGPRT), (Szybalska and Szybalski, 1992, *Proc. Natl. Acad. Sci. USA*, 48:202), and adenine phosphoribosyltransferase (Lowy et al., 1980, *Cell*, 22:817) genes, which can be employed in tk-, hgprt-, or aprt-cells (APRT), respectively.

Anti-metabolite resistance can also be used as the basis of selection for the following nonlimiting examples of marker genes: dhfr, which confers resistance to methotrexate (Wigler et al., 1980, *Proc. Natl. Acad. Sci. USA*, 77:357; and O'Hare et al., 1981, *Proc. Natl. Acad. Sci. USA*, 78:1527); gpt, which confers resistance to mycophenolic acid (Mulligan and Berg, 1981, *Proc. Natl. Acad. Sci. USA*, 78:2072); neo, which confers resistance to the aminoglycoside G418 (*Clinical Pharmacy*, 12:488-505; Wu and Wu, 1991, *Biotherapy*, 3:87-95; Tolstoshev, 1993, *Ann. Rev. Pharmacol. Toxicol.*, 32:573-596; Mulligan, 1993, *Science*, 260:926-932; Anderson, 1993, *Ann. Rev. Biochem.*, 62:191-21; May, 1993, *TIB TECH*, 11(5):155-215; and hygro, which confers resistance to hygromycin (Santerre et al., 1984, *Gene*, 30:147). Methods commonly known in the art of recombinant DNA technology can be routinely applied to select the desired recombinant cell clones, and such methods are described, for example, in Ausubel et al. (eds.), *Current Protocols in Molecular Biology*, John Wiley & Sons, NY (1993); Kriegler, 1990, *Gene Transfer and Expression, A Laboratory Manual*, Stockton Press, NY; in Chapters 12 and 13, Dracopoli et al. (eds), *Current Protocols in Human Genetics*, John Wiley & Sons, NY (1994); Colberre-Garapin et al., 1981. *J. Mol. Biol.*, 150:1, which are incorporated by reference herein in their entireties.

In addition, the expression levels of an expressed protein molecule can be increased by vector amplification (for a review, see Bebbington and Hentschel, "The use of vectors based on gene amplification for the expression of cloned genes in mammalian cells in DNA cloning", Vol. 3, Academic Press, New York, 1987). When a marker in the vector system expressing a protein is amplifiable, an increase in the level of inhibitor present in the host cell culture will increase the number of copies of the marker gene. Since the amplified region is associated with the protein-encoding gene, production of the protein will concomitantly increase (Crouse et al., 1983, *Mol. Cell. Biol.,* 3:257).

Vectors which harbor glutamine synthase (GS) or dihydrofolate reductase (DHFR) encoding nucleic acid as the selectable markers can be amplified in the presence of the drugs methionine sulphoximine or methotrexate, respectively. An advantage of glutamine synthase based vectors is the availability of cell lines (e.g., the murine myeloma cell line, NSO) which are glutamine synthase negative. Glutamine synthase expression systems can also function in glutamine synthase expressing cells (e.g., CHO cells) by providing additional inhibitor to prevent the functioning of the endogenous gene.

Vectors that express DHFR as the selectable marker include, but are not limited to, the pSV2-dhfr plasmid (Subramani et al., *Mol. Cell. Biol.* 1:854 (1981). Vectors that express glutamine synthase as the selectable marker include, but are not limited to, the pEE6 expression vector described in Stephens and Cockett, 1989, *Nucl. Acids. Res.,* 17:7110. A glutamine synthase expression system and components thereof are detailed in PCT publications: WO87/04462; WO86/05807; WO89/01036; WO89/10404; and WO91/06657 which are incorporated by reference herein in their entireties. In addition, glutamine synthase expression vectors that can be used in accordance with the present invention are commercially available from suppliers, including, for example, Lonza Biologics, Inc. (Portsmouth, N.H.).

In a particular embodiment, a nucleic acid sequence encoding a soluble CTLA4 molecule or a soluble CTLA4 mutant molecule can be inserted into a vector designed for expressing foreign sequences in a eukaryotic host. The regulatory elements of the vector can vary according to the particular eukaryotic host. Vectors which express the soluble CTLA4 or soluble CTLA4 mutant in eukaryotic host cells can include enhancer sequences for optimizing protein expression.

Types of Cell Cultures

For the purposes of understanding, yet without limitation, it will be appreciated by the skilled practitioner that cell cultures and culturing runs for protein production can include three general types; namely, continuous culture, batch culture and fed-batch culture. In a continuous culture, for example, fresh culture medium supplement (i.e., feeding medium) is provided to the cells during the culturing period, while old culture medium is removed daily and the product is harvested, for example, daily or continuously. In continuous culture, feeding medium can be added daily and can be added continuously, i.e., as a drip or infusion. For continuous culturing, the cells can remain in culture as long as is desired, so long as the cells remain alive and the environmental and culturing conditions are maintained.

In batch culture, cells are initially cultured in medium and this medium is neither removed, replaced, nor supplemented, i.e., the cells are not "fed" with new medium, during or before the end of the culturing run. The desired product is harvested at the end of the culturing run.

For fed-batch cultures, the culturing run time is increased by supplementing the culture medium one or more times daily (or continuously) with fresh medium during the run, i.e., the cells are "fed" with new medium ("feeding medium") during the culturing period. Fed-batch cultures can include various feeding regimens and times, for example, daily, every other day, every two days, etc., more than once per day, or less than once per day, and so on. Further, fed-batch cultures can be fed continuously with feeding medium.

The desired product is then harvested at the end of the culturing/production run. The present invention preferably embraces fed-batch cell cultures in which a glucocorticoid compound is added at a time after inoculation.

According to the present invention, cell culture can be carried out, and glycoproteins can be produced by cells, under conditions for the large or small scale production of proteins, using culture vessels and/or culture apparatuses that are conventionally employed for animal or mammalian cell culture. As is appreciated by those having skill in the art, tissue culture dishes, T-flasks and spinner flasks are typically used on a laboratory scale. For culturing on a larger scale, (e.g., 500 L, 5000 L, and the like, for example, as described in commonly-assigned U.S. Pat. Nos. 7,541,164, 7,332,303, and U.S. application Ser. No. 12/086,786, filed Dec. 19, 2006, the contents of which are incorporated by reference herein in their entirety) procedures including, but not limited to, a fluidized bed bioreactor, a hollow fiber bioreactor, roller bottle culture, or stirred tank bioreactor systems can be used. Microcarriers may or may not be used with the roller bottle or stirred tank bioreactor systems. The systems can be operated in a batch, continuous, or fed-batch mode. In addition, the culture apparatus or system may or may not be equipped with a cell separator using filters, gravity, centrifugal force, and the like.

Phases of Cell Culture and Associated Parameters

The term "inoculation" refers to the addition of cells to starting medium to begin the culture.

The "growth phase" of a culture is the phase during which the viable cell density at any time point is higher than at any previous time point.

The "stationary phase" of a culture is the phase during which the viable cell density is approximately constant (i.e. within measuring error) over a time period of any length.

The "death phase" of a culture is the phase that comes after the growth phase or after the growth phase and the stationary phase, and during which the viable cell density at any time point is lower than at any previous time point during that phase.

In a "growth-associated" culture process, such as cases where a glucocorticoid compound causes an extended growth phase, the production phase may start during the extended growth phase.

In a "non-growth" associated culture process, the production phase of cell culture may be the stationary phase.

Preferably, the culture medium is supplemented ("fed") during the production phase to support continued protein production, particularly in an extended production phase, and to attain ample quantities of high quality glycoprotein product (as exemplified and/or determined by a high level of end sialic acid content upon protein recovery). Feeding can occur on a daily basis, or according to other schedules to support cell viability and protein production.

The culturing process according to the present invention may result in more viable cell survival until the end of the culturing period. Accordingly, in some embodiments, the more cells that survive, the more cells that are producing the desired product. This, in turn, results in a greater accumulated amount of the product at the end of the culturing process, with the rate of protein production by individual cells, i.e., cell specific productivity, remaining the same. Cell specific productivity or cell specific rate, as known in the art, typically refers to the specific expression rate of product produced per cell, or per measure of cell mass or volume.

Cell specific productivity is measured in grams of protein produced per cell per day, for example, and can be measured according to an integral method involving the following formulae:

$$dP/dt = q_p X, \text{ or}$$

$$P = q_p \int_0^t X dt$$

where $q_p$ is the cell specific productivity constant; X is the number of cells or cell volume, or cell mass equivalents; and dP/dt is the rate of protein production. Thus, $q_p$ can be obtained from a plot of product concentration versus time integral of viable cells ($\int_0^t X dt$ "viable cell days"). According to this formula, when the amount of glycoprotein product produced is plotted against the viable cell days, the slope is equivalent to the cell specific rate. Viable cells can be determined by several measures, for example, biomass, $O_2$ uptake rate, lactase dehydrogenase (LDH), packed cell volume or turbidity. (e.g., U.S. Pat. No. 5,705,364 to T. Etcheverry et al.)

Production of Soluble CTLA4 Molecules and Soluble CTLA4 Mutant Molecules by the Culturing Methods of the Present Invention In other embodiments encompassed by the present invention, the cell culture methods of the invention are utilized to produce a soluble CTLA4 molecule or a soluble CTLA4 mutant molecule, as described below. A soluble CTLA4 molecule is preferably a CTLA4 fusion protein, preferably a CTLA4Ig. More preferred is CTLA4Ig that comprises amino acids −1 to 357 or +1 to 357 as shown in FIG. 19. A soluble CTLA4 mutant molecule is preferably L104EA29YIg that comprises amino acids −1 to 357 or +1 to 357 as shown in FIG. 20. The cell culture methods involving extended production phases for protein product are especially suitable for generating high quality and large amounts of soluble CTLA4 molecules and soluble CTLA4 mutant molecules, by their host cells in culture.

In a preferred embodiment, CTLA4Ig is produced by recombinantly engineered host cells. The CTLA4Ig fusion protein can be recombinantly produced by CHO cells transfected with a vector containing the DNA sequence encoding CTLA4Ig. (See, U.S. Pat. No. 5,844,095 to P. S. Linsley et al). The CTLA4Ig fusion protein is produced in high quantity and is appropriately sialylated when cultured in accordance with the processes of this invention. The invention affords the production of high levels of recoverable protein product, e.g., sialylated CTLA4Ig protein product. In another preferred embodiment, the soluble CTLA4 mutant molecule L104EA29YIg that comprises amino acids −1 to 357 or +1 to 357 as shown in FIG. 20 is produced by the cell culture methods of the present invention.

A ligand for CTLA4 is a B7 molecule. As used herein, "ligand" refers to a molecule that specifically recognizes and binds another molecule. The interaction of a molecule and its ligand can be regulated by the products of the culturing processes of this invention. For example, CTLA4 interaction with its ligand B7 can be blocked by the administration of CTLA4Ig molecules. As other examples, the interaction of Tumor Necrosis Factor (TNF) with its ligand, TNF receptor (TNFR), can be blocked by administration of etanercept or other TNF/TNFR blocking molecules.

Wild type CTLA4 or "non-mutated CTLA4" has the amino acid sequence of naturally occurring, full length CTLA4 as shown in FIG. 20 (and also as described in U.S. Pat. Nos. 5,434,131, 5,844,095, and 5,851,795, incorporated herein by reference in their entirety), or any portion thereof that recognizes and binds a B7 molecule, or interferes with a B7 molecule, so that binding to CD28 and/or CTLA4 (e.g., endogenous CD28 and/or CTLA4) is blocked. Wild type CTLA4 comprises particular portions, including, for example, the extracellular domain of wild type CTLA4 beginning with methionine at position +1 and ending at aspartic acid at position +124, or the extracellular domain of wild type CTLA4 beginning with alanine at position −1 and ending at aspartic acid at position +124 as shown in FIG. 21.

The naturally occurring wild type CTLA4 is a cell surface protein having an N-terminal extracellular domain, a transmembrane domain, and a C-terminal cytoplasmic domain. The extracellular domain binds to a target molecule, such as a B7 molecule. In a cell, the naturally occurring, wild type CTLA4 protein is translated as an immature polypeptide, which includes a signal peptide at the amino, or N-terminal, end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. The mature CTLA4 protein may start at methionine at position +1 or alanine at position −1. The mature form of the CTLA4 molecule includes the extracellular domain or any portion thereof, which binds to B7.

A CTLA4 mutant molecule, as used herein, refers to a molecule comprising wild type CTLA4 as shown in FIG. 21, or any portion or derivative thereof that has a mutation, or multiple mutations, in the wild type CTLA4 sequence, preferably in the extracellular domain of wild type CTLA4, and binds B7. A CTLA4 mutant molecule has a sequence that it is similar, but not identical, to the sequence of wild type CTLA4 molecule, but still binds B7. The mutations can include one or more amino acid residues substituted with an amino acid having conservative (e.g., a leucine substituted for an isoleucine) or non-conservative (e.g., a glycine substituted with a tryptophan) structure or chemical properties, amino acid deletions, additions, frameshifts, or truncations.

CTLA4 mutant molecules can include a non-CTLA4 molecule therein or attached thereto, i.e., CTLA4 mutant fusion proteins. The mutant molecules can be soluble (i.e., circulating) or they can be bound to a cell surface (membrane-bound). CTLA4 mutant molecules include L104EA29YIg and those described in U.S. Application Ser. Nos. 60/214,065 and 60/287,576; in WO 01/92337 A2; in U.S. Pat. Nos. 6,090,914, 5,844,095, 7,094,874 and 5,773,253; and as described in R. J. Peach et al., 1994, *J Exp Med*, 180:2049-2058.) CTLA4 mutant molecules can be synthetically or recombinantly produced.

CTLA4Ig is a soluble fusion protein comprising an extracellular domain of wild type CTLA4, or a portion thereof that binds B7, joined to an immunoglobulin (Ig) molecule, or a portion thereof. The extracellular domain of CTLA4 or portion thereof is joined to an Ig moiety comprising all or a portion of an immunoglobulin molecule, preferably all or a portion of an immunoglobulin constant region such as all or a portion of IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCδ (IgCdelta) or IgCε (IgCepsilon), rendering the fusion molecule soluble. The Ig moiety can include the hinge, CH2 and CH3 domains, or the CH1, hinge, CH2 and CH3 domains, of the aforementioned constant regions or other constant regions. Preferably, the Ig moiety is human or monkey and comprises the hinge, $CH_2$ and CH3 domains. Most preferably the Ig moiety comprises the hinge, $CH_2$ and CH3 domains of human IgCγ1, or consists of the hinge, $CH_2$ and CH3 domains of human IgCγ1. In an Ig moiety of CTLA4Ig, the Ig constant region or portion thereof can be mutated, thus resulting in a reduction of its effector functions (see, e.g., U.S. Pat. Nos. 5,637,481, 5,844,095 and 5,434,131). As used herein, the terms Ig moiety, Ig constant region, Ig C (constant) domain, IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCδ (IgCdelta) or IgCε (IgCepsilon), include both native sequences and sequences that have been mutated, such as, for example, sequences having mutations in the constant region that reduce effector function.

A particular embodiment related to CTLA4 comprises the extracellular domain of wild type CTLA4 starting at methionine at position +1 and ending at aspartic acid at position +124, or starting at alanine at position −1 to aspartic acid at position +124; a junction amino acid residue glutamine at position +125; and an immunoglobulin portion encompassing glutamic acid at position +126 through lysine at position +357, as shown in FIG. 19. DNA encoding this CTLA4Ig was deposited on May 31, 1991, in the American Type Culture Collection (ATCC), 10801 University Blvd., Manassas, Va. 20110-2209, under the provisions of the Budapest Treaty, and has been accorded ATCC accession number ATCC 68629; P. Linsley et al., 1994, *Immunity* 1:793-80. A CHO cell line expressing CTLA4Ig was deposited on May 31, 1991 in ATCC under identification number CRL-10762. The soluble CTLA4Ig molecules produced according to the methods described herein may or may not include a signal (leader) peptide sequence. FIGS. 19 and 20 include an illustration of a signal (leader) peptide sequence. Typically, the molecules do not include a signal peptide sequence.

L104EA29YIg is a fusion protein that is a soluble CTLA4 mutant molecule comprising an extracellular domain of wild type CTLA4 with amino acid changes A29Y (a tyrosine amino acid residue substituting for an alanine at position 29) and L104E (a glutamic acid amino acid residue substituting for a leucine at position +104) joined to an Ig tail. FIG. 20 illustrates L104EA29YIg. The amino acid sequence of L104EA29YIg comprises alanine at amino acid position −1 to lysine at amino acid position +357 as shown in FIG. 20. Alternatively, the amino acid sequence of L104EA29YIg comprises methionine at amino acid position +1 to lysine at amino acid position +357 as shown in FIG. 20. L104EA29YIg comprises a junction amino acid residue glutamine at position +125 and an Ig portion encompassing glutamic acid at position +126 through lysine at position +357. DNA encoding L104EA29YIg was deposited on Jun. 20, 2000, in the American Type Culture Collection (ATCC) under the provisions of the Budapest Treaty, and has been accorded ATCC accession number PTA-2104. 104EA29Y-Ig is described in co-pending U.S. patent application Ser. Nos. 09/579,927, 60/287,576 and 60/214,065, and in WO/01/923337 A2, which are incorporated by reference herein in their entireties. The soluble L104EA29YIg molecules produced by the culturing methods of this invention may or may not include a signal (leader) peptide sequence. Typically, the molecules produced according to the invention do not include a signal peptide sequence.

As used herein, the term "soluble" refers to any molecule, or fragment thereof, not bound or attached to a cell, i.e., circulating. For example, CTLA4 can be made soluble by attaching an Ig moiety to the extracellular domain of CTLA4. Alternatively, a molecule such as CTLA4 can be rendered soluble by removing its transmembrane domain. Typically, the soluble molecules produced according to the invention do not include a signal (or leader) sequence.

A soluble CTLA4 molecule refers to a non-cell-surface-bound (i.e., circulating) molecule comprising wild type CTLA4, or any portion or derivative that binds B7, including, but not limited to, soluble CTLA4 fusion proteins; soluble CTLA4 fusion proteins such as CTLA4Ig fusion proteins (e.g., ATCC 68629), wherein the extracellular domain of CTLA4 is fused to an Ig moiety that is all or a portion of an Ig molecule, preferably all or a portion of an Ig constant region, such as all or a portion of IgCγ1 (IgCgamma1), IgCγ2 (IgCgamma2), IgCγ3 (IgCgamma3), IgCγ4 IgCgamma4), IgCμ (IgCmu), IgCα1 (IgCalpha1), IgCα2 (IgCalpha2), IgCδ (IgCdelta) or IgCε (IgCepsilon), rendering the fusion molecule soluble; soluble CTLA4 fusion proteins in which the extracellular domain is fused or joined with a portion of a biologically active or chemically active protein such as the papillomavirus E7 gene product (CTLA4-E7), melanoma-associated antigen p97 (CTLA4-p97) or HIV env protein (CTLA4-env gp120), as described in U.S. Pat. No. 5,844,095, herein incorporated by reference in its entirety; hybrid (chimeric) fusion proteins such as CD28/CTLA4Ig as described in U.S. Pat. No. 5,434,131, herein incorporated by reference in its entirety; CTLA4 molecules with the transmembrane domain removed to render the protein soluble (See, e.g., M. K. Oaks et al., 2000, *Cellular Immunology,* 201:144-153, herein incorporated by reference in its entirety); the soluble CTLA4 mutant molecule L104EA29YIg.

A soluble CTLA4 molecule can also be a soluble CTLA4 mutant molecule. The soluble CTLA4 molecules produced according to this invention may or may not include a signal (leader) peptide sequence. The signal peptide can be any sequence that will permit secretion of the molecule, including the signal peptide from oncostatin M (Malik et al., 1989, *Molec. Cell. Biol.,* 9:2847-2853), or CD5 (N. H. Jones et al., 1986, *Nature,* 323:346-349), or the signal peptide from any extracellular protein. The soluble CTLA4 molecule produced by the culturing processes of the invention can include the oncostatin M signal peptide linked at the N-terminal end of the extracellular domain of CTLA4. Typically, in the invention the molecules do not include a signal peptide sequence.

"CTLA4 fusion protein" as used herein refers to a molecule comprising the extracellular domain of wild type CTLA4, or portion thereof that binds to B7, fused to a non-CTLA4 moiety that renders the CTLA4 molecule soluble, such as an Ig moiety. For example, a CTLA4 fusion protein can include the extracellular domain of CTLA4 fused to all or a portion of an Ig constant region. Examples of Ig constant domains (or portions thereof) that may be fused to CTLA4 include all, but are not limited to those listed hereinabove. A CTLA4 fusion protein can also be a CTLA4 mutant molecule.

As used herein, "non-CTLA4 moiety" refers to a molecule or portion thereof that does not bind CD80 and/or CD86 and does not interfere with the binding of CTLA4 to its ligand. Examples include, but are not limited to, an Ig moiety that is all or a portion of an Ig molecule, a portion of a biologically active or chemically active protein such as the papillomavirus E7 gene product (CTLA4-E7), melanoma-associated antigen p97 (CTLA4-p97) or HIV env protein (CTLA4-env gp120) (as described in U.S. Serial No. 5,844, 095, herein incorporated by reference in its entirety). Examples of Ig moieties include all or a portion of an immunoglobulin constant domain, such as IgCγ1 (IgCgamma1), IgCγ2 (IgCgamma2), IgCγ3 (IgCgamma3), IgCγ4 IgCgamma4), IgCμ (IgCmu), IgCα1 (IgCalpha1), IgCα2 (IgCalpha2), IgCδ (IgCdelta) or IgCε (IgCepsilon). The Ig moiety can include the hinge, CH2 and CH3 domains, or the CH1, hinge, CH2 and CH3 domains of the aforementioned constant regions or other constant regions. Preferably, the Ig moiety is human or monkey and includes the hinge, CH2 and CH3 domains. Most preferably the Ig moiety includes the hinge, CH2 and CH3 domains of human IgCγ1, or is the hinge, CH2 and CH3 domains of human IgCγ1. In an Ig moiety, the Ig constant region or portion thereof can be mutated so as to reduce its effector functions (see, e.g., U.S. Pat. Nos. 5,637,481, 5,844,095 and 5,434,131).

The extracellular domain of CTLA4 refers to any portion of wild type CTLA4 that recognizes and binds B7. For example, an extracellular domain of CTLA4 comprises methionine at position +1 to aspartic acid at position +124 (FIG. 21). For example, an extracellular domain of CTLA4 comprises alanine at position −1 to aspartic acid at position +124 (FIG. 21).

As used herein, the term "mutation" refers to a change in the nucleotide or amino acid sequence of a wild type molecule, for example, a change in the DNA and/or amino acid sequences of the wild type CTLA4 extracellular domain. A mutation in the DNA may change a codon leading to a change in the encoded amino acid sequence. A DNA change may include substitutions, deletions, insertions, alternative splicing, or truncations. An amino acid change may include substitutions, deletions, insertions, additions, truncations, or processing or cleavage errors of the protein. Alternatively, mutations in a nucleotide sequence may result in a silent mutation in the amino acid sequence, as is well understood in the art. As is also understood, certain nucleotide codons encode the same amino acid. Examples include nucleotide codons CGU, CGG, CGC, and CGA which encode the amino acid, arginine (R); or codons GAU, and GAC which encode the amino acid, aspartic acid (D).

Thus, a protein can be encoded by one or more nucleic acid molecules that differ in their specific nucleotide sequence, but still encode protein molecules having identical sequences. The mutant molecule may have one, or more than one, mutation. For guidance, the amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

As used herein, a "fragment or portion" is any part or segment of a molecule. For CTLA4 or CD28, a fragment or portion is preferably the extracellular domain of CTLA4 or CD28, or a part or segment thereof, that recognizes and binds B7 or interferes with a B7 so that it blocks binding to CD28 and/or CTLA4. Also, as used herein, "corresponding" means sharing sequence identity.

As used herein, a "derivative" is a molecule that shares sequence similarity and activity of its parent molecule. For example, a derivative of CTLA4 includes a soluble CTLA4 molecule having an amino acid sequence at least 70% similar to the extracellular domain of wildtype CTLA4, and which recognizes and binds B7 e.g. CTLA4Ig or soluble CTLA4 mutant molecule L104EA29YIg. A derivative means any change to the amino acid sequence and/or chemical quality of the amino acid e.g., amino acid analogs.

As used herein, to "regulate an immune response" is to activate, stimulate, up-regulate, inhibit, block, reduce, attenuate, down-regulate or modify the immune response. A variety of diseases, e.g., autoimmune diseases, may be treated by regulating an immune response, e.g., by regulating functional CTLA4- and/or CD28-positive cell interactions with B7-positive cells. For example, a method of regulating an immune response comprises contacting B7-positive cells with a soluble CTLA4 molecule, such as those produced according to this invention, to form soluble CTLA4/B7 complexes, wherein the soluble CTLA4 molecule interferes with the reaction of an endogenous CTLA4 and/or CD28 molecule with the B7 molecule. To "block" or "inhibit" a receptor, signal or molecule, as referred to herein, means to interfere with the activation of the receptor, signal or molecule, as detected by an art-recognized test. Blockage or inhibition can be partial or total.

As used herein, "blocking B7 interaction" refers to interfering with the binding of B7 to its ligands, such as CD28 and/or CTLA4, thereby obstructing T-cell and B7-positive cell interactions. Examples of agents that block B7 interactions include, but are not limited to, molecules such as an antibody (or portion thereof) that recognizes and binds to the any of CTLA4, CD28 or B7 molecules (e.g., B7-1, B7-2); a soluble form (or portion thereof) of the molecules such as soluble CTLA4; a peptide fragment or other small molecule designed to interfere with the cell signal through a CTLA4/CD28/B7-mediated interaction. In a preferred embodiment, the blocking agent is a soluble CTLA4 molecule, such as CTLA4Ig (ATCC 68629) or L104EA29YIg (ATCC PTA-2104); a soluble CD28 molecule, such as CD28Ig (ATCC 68628); a soluble B7 molecule, such as B7-Ig (ATCC 68627); an anti-B7 monoclonal antibody (e.g., ATCC HB-253, ATCC CRL-2223, ATCC CRL-2226, ATCC HB-301, ATCC HB-11341 and monoclonal antibodies as described in U.S. Pat. No. 6,113,898 or in Yokochi et al., 1982, *J. Immunol.*, 128(2):823-827); an anti-CTLA4 monoclonal antibody (e.g., ATCC HB-304, and monoclonal antibodies as described in references 82-83); and/or an anti-CD28 monoclonal antibody (e.g. ATCC HB 11944 and MAb 9.3, as described in Hansen et al., 1980, *Immunogenetics*, 10: 247-260, or Martin et al., 1984, *J. Clin. Immunol.*, 4(1):18-22). Blocking B7 interactions can be detected by art-recognized tests such as determining reduction of immune disease (e.g., rheumatic disease) associated symptoms, by determining a reduction in T-cell/B7-cell interactions, or by determining a reduction in the interaction of B7 with CTLA4/CD28. Blockage can be partial or total.

As used herein, an effective amount of a molecule refers to an amount that blocks the interaction of the molecule with its ligand. For example, an effective amount of a molecule that blocks the interaction of B7 with CTLA4 and/or CD28 is the amount of the molecule that, when bound to B7 molecules on B7-positive cells, inhibits B7 molecules from binding endogenous ligands such as CTLA4 and CD28. Alternatively, an effective amount of a molecule that blocks the interaction of B7 with CTLA4 and/or CD28 is the amount of the molecule that, when bound to CTLA4 and/or CD28 molecules on T cells, inhibits B7 molecules from binding endogenous ligands such as CTLA4 and CD28. The inhibition or blockage can be partial or complete.

For clinical protocols, it is preferred that the Ig moiety of a fusion protein, such as CTLA4Ig or mutant CTLA4Ig, does not elicit a detrimental immune response in a subject. The preferred moiety is all or a portion of the Ig constant region, including human or non-human primate Ig constant regions. Examples of suitable Ig regions include IgCγ1 (IgCgamma1), IgCγ2 (IgCgamma2), IgCγ3 (IgCgamma3), IgCγ4 IgCgamma4), IgCμ (IgCmu), IgCα1 (IgCalpha1), IgCα2 (IgCalpha2), IgCδ (IgCdelta) or IgCε (IgCepsilon), including the hinge, CH2 and CH3 domains, or the CH1, hinge, CH2 and CH3 domains, which are involved in effector functions such as binding to Fc receptors, complement-dependent cytotoxicity (CDC), or antibody-dependent cell-mediated cytotoxicity (ADCC). The Ig moiety can have one or more mutations therein, (e.g., in the CH2 domain to reduce effector functions such as CDC or ADCC) where the mutation modulates the capability of the Ig to bind its ligand by increasing or decreasing the capability of the Ig to bind to Fc receptors. For example, mutations in the Ig moiety can include changes in any or all of its cysteine residues within the hinge domain. For example, the cysteines at positions+ 130, +136, and +139 are substituted with serine. The Ig moiety can also include the proline at position +148 substituted with a serine. Further, mutations in the Ig moiety can include having the leucine at position +144 substituted with phenylalanine; leucine at position +145 substituted with glutamic acid; or glycine at position +147 substituted with alanine.

EXAMPLES

The following Examples set forth specific aspects of the invention to illustrate the invention and provide a description of the present methods for those of skill in the art. The Examples should not be construed as limiting the invention, as the Examples merely provide specific methodology and exemplification that are useful in the understanding and practice of the invention and its various aspects.

Examples 1-5 as set forth below describe experiments relating to cell culture processes involving addition of glucocorticoids during the culture run.

Example 1

In this study, the intracellular effects of dexamethasone (DEX) on the CHO cell glycosylation process, and the extracellular effects due to sialidase activity were studied. Here it is demonstrated for the first time that DEX was capable of improving the sialylation of a recombinant fusion glycoprotein produced by CHO. The net effects of DEX in promoting increased sialylation tested in shake flask cultures were then successfully confirmed in controlled bioreactors, and resulted in enhanced sialic acid content as well as reduced de-sialylation rates in the fed-batch cultures.

Cell Line and Medium

The CHO cell line used in this study was originally subcloned from DG44 parental cells and cultured in a proprietary protein-free growth medium.

Shake Flask Experiments

The experiments were carried out in 250-mL shake flasks (VWR international) with starting volumes of 100 mL and initial cell densities of $6 \times 10^5$ cells/mL. The cultures were placed on a shaker platform (VWR international) at 150 rpm and maintained at 37° C. and 6% $CO_2$ for ten days. The cultures were sampled daily and the pH was adjusted as needed using 1M sodium carbonate and fed with glucose and glutamine every two days in order to maintain them at adequate levels. Cell density and viability were measured offline using a Cedex automated cell counter (Innovatis AG, Bielefeld, Germany). Culture pH and concentrations for glucose and glutamine were measured off-line using a Bioprofile Analyzer 400 (Nova Biomedical Corporation, Waltham, Mass.).

Bioreactor Operation

Bioreactor experiments were performed in 5-L bioreactors (Sartorius AG, Goettingen, Germany) with initial working volumes of 1.5 L. Agitation, pH, and dissolved oxygen were controlled at 150 rpm, 7.05, and 50% air saturation, respectively. Temperature was initially controlled at 37° C., but was shifted to a lower temperature during the culture to extend culture viability. The bioreactors were operated in fed-batch mode and were fed daily starting on day 3 with the proprietary feed medium to maintain adequate concentrations for glucose and other nutrients. Samples were taken during the cell culture process and analyzed for cell density, cell viability, substrates and metabolites.

Western blot analysis of α2,3-sialytransferase (α2,3-ST) and β1,4-galactosyltransferase (β1,4-GT)

Approximately $10^7$ CHO cells were washed with 1× Phosphate Buffered Saline (PBS), lysed with 1 mL of Laemmli sample buffer (Bio-Rad Laboratories, Hercules, Calif.), then denatured at 90° C. for 5 minutes. The whole cell lysates were separated on a 4-15% SDS-polyacrylamide gel, blotted to 0.45 μm nitrocellulose membranes (Bio-Rad Laboratories, Hercules, Calif.), and probed with primary and secondary antibodies. The primary antibodies were anti-human α2,3-ST rabbit polyclonal antibodies and anti-human β1,4-GT rabbit polyclonal antibodies (Santa Cruz Biotechnology, Santa Cruz, Calif.). The secondary antibody was horseradish peroxidase (HRP)-conjugated anti-rabbit antibody (Santa Cruz Biotechnology, Santa Cruz, Calif.). The membranes were stripped and re-probed with β-actin antibody (Santa Cruz Biotechnology, Santa Cruz, Calif.) and an HRP-conjugated anti-mouse secondary antibody. Immunodetection was performed using an enhanced chemiluminescence Western blotting detection system (GE Healthcare) and visualized with a VersaDoc Imaging System (Bio-Rad Laboratories, Hercules, Calif.).

Measurement of Sialidase Activity in Supernatant

Sialidase activity was analyzed using the Amplex Red Neuraminidase (Sialidase) Assay Kit (Invitrogen, Carlsbad, Calif.). Briefly, neuraminidase in the sample is used to desialylate fetuin. This assay utilizes Amplex Red to detect $H_2O_2$ generated by oxidation of the desialylated galactose residues on the fetuin by galactose oxidase. The $H_2O_2$, in the presence of HRP, reacts stoichiometrically with Amplex Red reagent to generate the red-fluorescent oxidation product, resorufin 5, which is then analyzed either fluorometrically or spectrophotometrically. In each assay, 50 μL of working solution (100 μM Amplex Red, 0.2 U/mL HRP, 4 U/mL galactose oxidase and 500 μg/mL fetuin) was added into each microplate well containing 50 μL of diluted cell culture supernatant. After 30 minutes incubation at 37° C., samples were analyzed for absorbance at 560 nm using a microplate reader.

Sialic Acid Assay

The sialic acid to recombinant protein molar ratio was calculated by determining the sialic acid and recombinant protein concentrations. Sialic acid (SA), including N-Acetylneuraminic (Neu5Ac) and N-glycolylneuraminic acid (Neu5Gc), was released by partial acid hydrolysis. The derivatives were then separated by reversed-phase HPLC to determine sialic acid content. The protein concentrations were determined by UV absorbance at 280 nm. Sialic acid content is reported as molar ratios, which is the total moles of Neu5Ac and Neu5Gc per mole of recombinant glycoprotein. Sialic acid contents are reported as normalized values, which are the actual values divided by an arbitrary value. The same divisor was used to normalize all sialic acid content data in the studies reported here.

N-Linked Oligosaccharides Measurement

High-pH anion-exchange chromatography with pulsed amperometric detection (HPAEC-PAD) was used for the profiling of N-linked oligosaccharides (Basa and Spellman 1990; Townsend and Hardy 1991) to provide information on site-specific N-linked glycosylation. N-linked oligosaccharides were cleaved from protein and separated on HPAEC-PAD into four domains based on the amount of sialic acid present. Domain I represents the asialo species. Domains II, III, and IV are sialylated species and represent monosialylated, disialylated, and tri- and tetrasialylated species, respectively. N-linked sialylated species fraction is reported as the percentage of N-linked sialylated species within the total N-linked oligosaccharides species, which includes both asialo and sialylated species. N-linked sialylated species fractions are reported as normalized values, which are the actual values divided by an arbitrary value. The same divisor was used to normalize all N-linked sialylated species fraction data in the studies reported here.

O-linked Oligosaccharides Measurement

O-linked glycosylation was characterized by intact mass analysis of a reference standard and Protein-A purified samples of the fusion protein (Reference). Samples were diluted in 100 mM Tris, 25 mM NaCl, pH 7.6 and incubated with PNGase F overnight to enzymatically remove all N-linked oligosaccharides. Samples were then injected for intact mass analysis after mixing with an internal standard of insulin. O-linked sialic acid content is reported as molar ratios, which is the moles of O-linked sialic acid per mole of recombinant glycoprotein.

Results

Dexamethasone Enhances Sialic Acid Content and Percentage of Sialylated Species in N-linked Oligosaccharides The CHO DG44 cell line expressing the fusion glycoprotein was treated with various levels of DEX to assess whether DEX affected sialic acid content and the percentages of the different sialylated species. This study was performed in duplicate 250-mL shake flasks using the culture conditions as described above. On the second day after inoculation, DEX was added to CHO cell cultures at final concentrations ranging from 0.01 to 10 μM DEX. Cultures were harvested on day 10, and the fusion protein was purified using a protein A column and analyzed for total sialic acid content, O-linked sialic acid content and the N-linked profile. Sialylation increased in the DEX-treated cultures in a concentration-dependent manner (Table 1).

TABLE 1

| DEX treatment (μM) | Percent increase of SA (%) | Percent increase of N-link asialo- (%) | Percent increase of N-link-Mono- (%) | Percent increase of N-link-Di- (%) | Percent increase of N-link-Tri and tetra- (%) | Percent increase of O-link SA (%) |
|---|---|---|---|---|---|---|
| 0.01 | 9.3 | −8.6 | 6.6 | 13.9 | 4.5 | 0.0 |
| 0.1 | 13.0 | −9.6 | 7.3 | 13.9 | 13.6 | 0.5 |
| 1.0 | 13.0 | −10.0 | 4.3 | 19.4 | 15.9 | 0.9 |
| 10 | 20.4 | −15.6 | 7.3 | 24.3 | 20.5 | 0.0 |

DEX concentrations from 0.01 μM to 10 μM resulted in 9.3% to 20.4% increase in the sialic acid content, with a maximal effect at 10 μM. Compared with the control, the N-linked oligosaccharide chromatographs for cultures with DEX treatment showed enhanced monosialylated, disialylated and the tri-plus tetra sialylated fractions of 4.3% to 7.3%, 13.9% to 24.3% and 4.5% to 20.5%, respectively. Conversely, there was a 8.5% to 15.6% reduction compared to the control in asialo fractions in the oligosaccharide distributions for the DEX-supplemented cultures. The N-linked chromatograms also showed the maximum effect at 10 μM DEX. These results indicate improved sialylation in the DEX treated cultures. However, no significant changes were observed in the O-linked sialic acid molar ratios from the DEX treated samples.

DEX Promotes β1,4-galactosyltransferase (β1,4-GT) and α2,3-sialyltransferase (α2,3-ST) Expression Western blotting was employed to elucidate potential mechanisms of DEX on sialylation by studying the expression of two enzymes, β1,4-GT and α2,3-ST, which are involved in the sialic acid addition pathways. In this experiment, DEX was added on the second day after inoculation to cultures at concentrations from 0.1 μM to 10 μM and the cells were harvested for Western blot analysis after three days. The housekeeper protein β-actin was used to compare sample loading. As shown in FIGS. 1A and 1B, the expression of β1,4-GT and α2,3-ST levels increased substantially in the DEX treated cultures compared to cultures without DEX treatment. Expression intensity for both enzymes generally increased with the DEX concentration. These results demonstrated that DEX was capable of stimulating expression of the sialyltransferases β1,4-GT and α2,3-ST in CHO cells.

Figure 2:
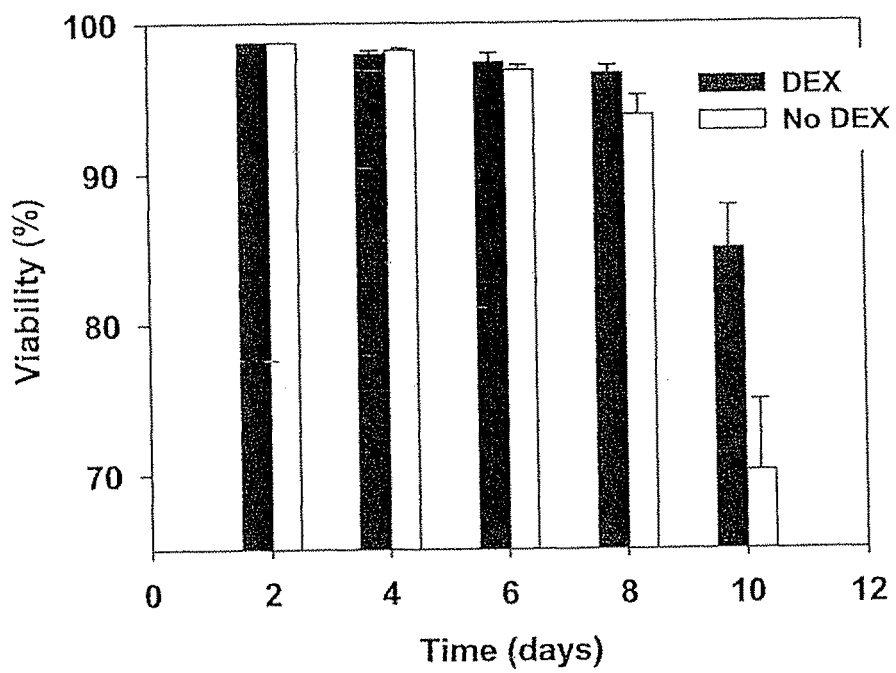
Figure 2:
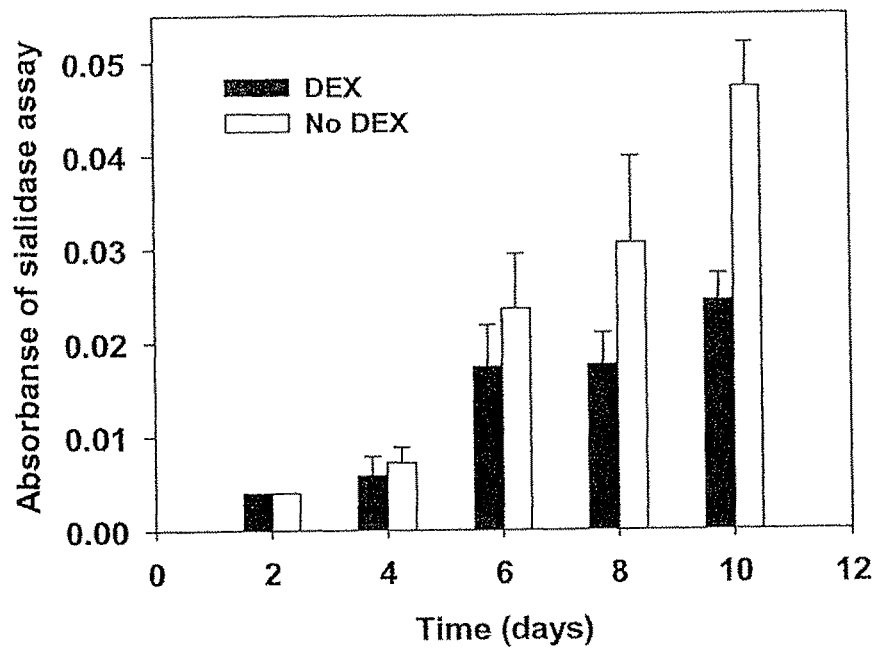

Cell Protective Effect of DEX Results in Reduced Sialidase Activity in the Culture Supernatant In Example 3, DEX treatment was shown to increase expression of the anti-apoptotic protein GILZ resulting in enhanced viability of the CHO cell cultures. To determine whether the improvement in cell viability due to DEX could lessen the degradative effect of sialidases on the recombinant fusion protein, a shake flask study was initiated to compare cell viability and supernatant sialidase activity profiles from cultures with and without 1 μM DEX. As shown in FIG. 2A and FIG. 2B, increased sialidase activity was associated with the decreased cell viabilities in both the DEX-treated and untreated cultures. Cell viability decreased from 98.0±0.1% on day 4 to 85.0±2.7% on day 10 in the DEX treated cultures compared to a day 10 viability of 70.2±4.6% for the control. The absorbance measurement of sialidase activity increased from 0.006±0.002 on day 4 to 0.024±0.003 on day 10 in the DEX treated cultures compared to a day 10 value of 0.047±0.004 in the control. Thus, the rate at which the cultures both declined in cell viability as well as increased in sialidase activity were significantly slower in the DEX-treated cultures. These results suggest that DEX was capable of inhibiting sialidase release through its cell protective effect.

Figure 3:
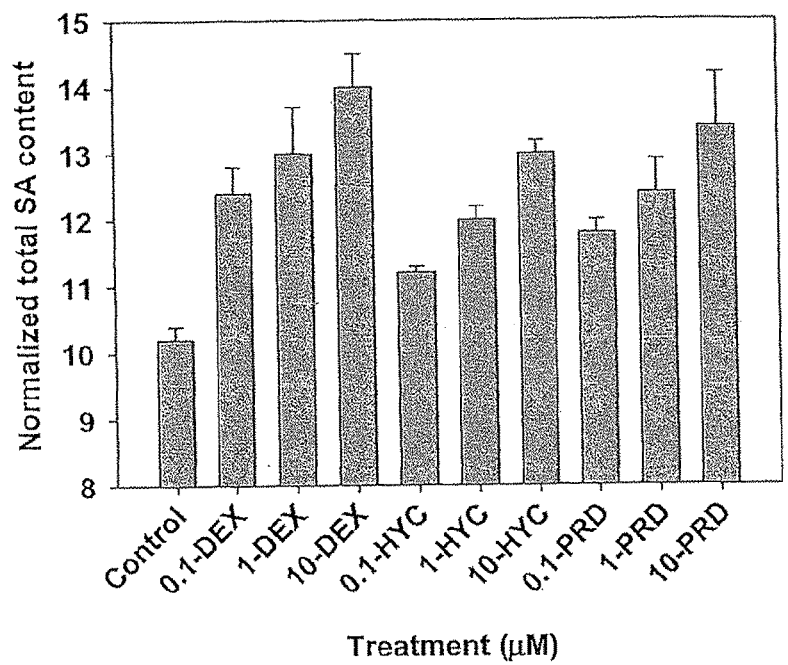
Figure 3:
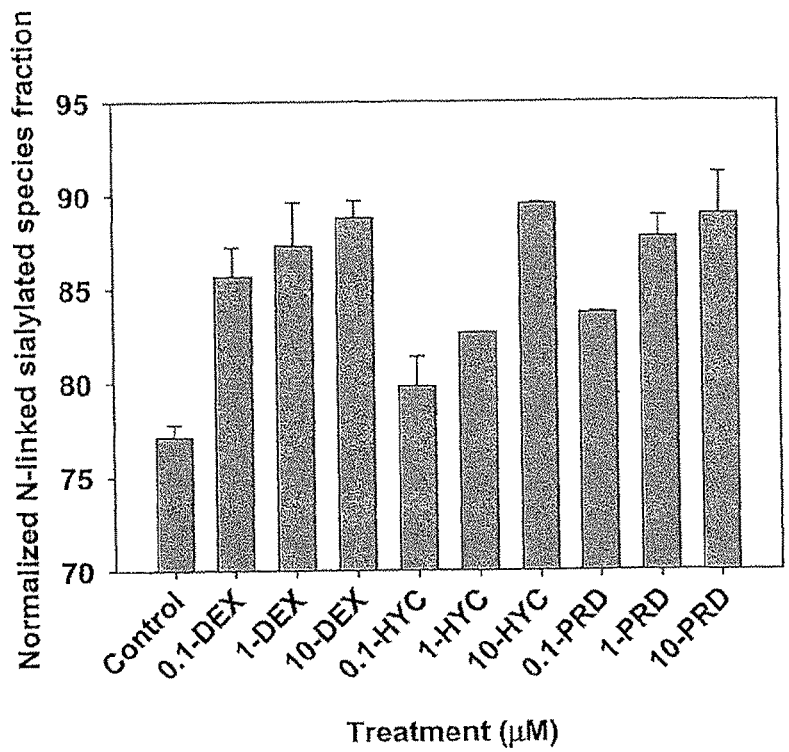

Comparison of Dexamethasone with Other Two Glucocorticoids, Hydrocortisone and Prednisolone Additional glucocorticoid compounds, hydrocortisone (HYC) and prednisolone (PRD) were also evaluated to determine whether the effect of DEX on increasing sialylation in CHO cells could be extended to other glucocorticoid compounds. DEX, HYC and PRD were added into cell culture medium on the second day after inoculation at the final concentrations of 0, 0.1, 1 and 10 μM. FIG. 3A and FIG. 3B show the normalized total sialic acid content and normalized N-linked sialylated species fraction after the 10-day culture for the different glucocorticoid conditions. The total sialic acid content at glucocorticoid concentrations between 0.1 to 10 M were 12.4±0.4 to 14.0±0.5 for DEX, 11.2±0.1 to 13.0±0.2 for HYC, and 11.8±0.2 to 13.4±0.8 for PRD, compared to 10.2±0.2 for the control. The N-linked sialylated species fraction at glucocorticoid concentrations between 0.1 to 10 M were 85.6±1.6 to 88.8±0.9 for DEX, 79.8±1.6 to 89.6±0.1 for HYC, and 83.7±0.1 to 89.0±0.2 for PRD compared to 77.1±0.7 for the control. Thus, similar to DEX, both HYC and PRD also showed increases in sialylation and the maximum effect was observed at 10 μM for all three glucocorticoid compounds within the studied concentration range. However, higher concentrations of HYC and PRD were required to achieve the same level of sialylation enhancement as DEX.

Mechanism for Sialylation Enhancement by Dexamethasone Involves the Glucocorticoid Receptor.

Figure 4:
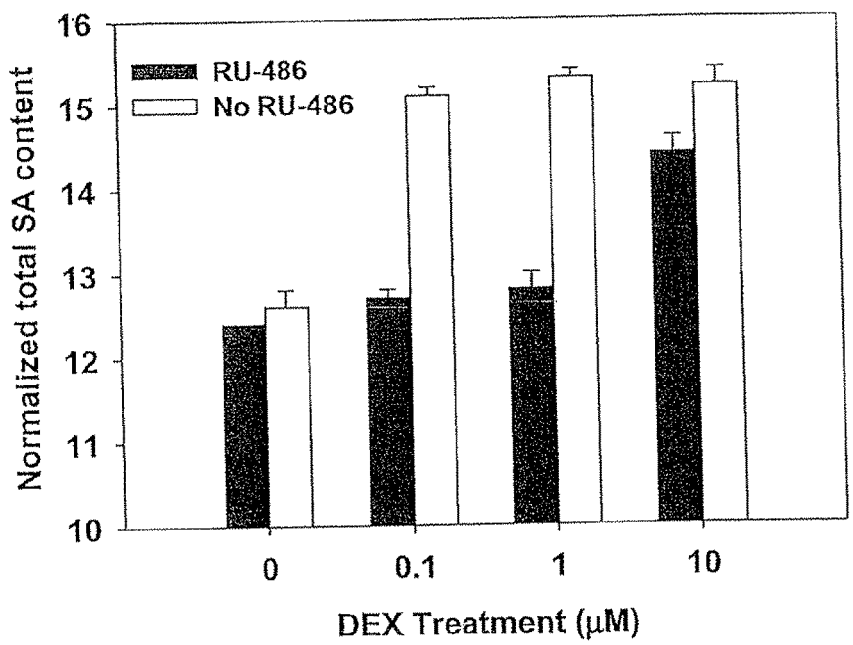
Figure 4:
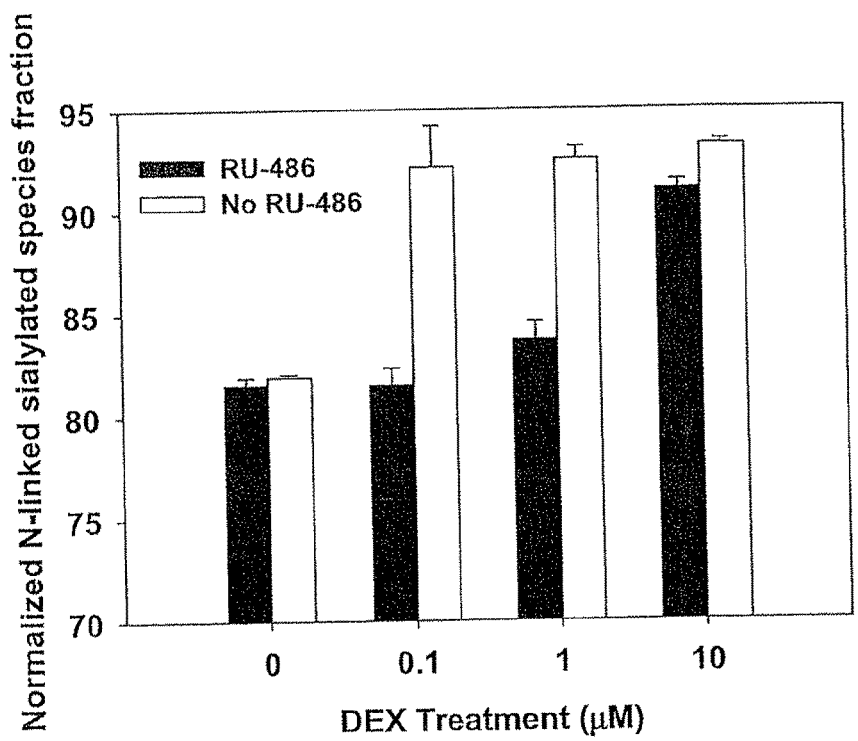

In order to determine whether the sialylation improvement from DEX addition was mediated through the glucocorticoid receptor (GR), the GR antagonist mifepristone (RU-486) was added to cell culture medium before DEX treatment. Specifically, 1 μM of RU-486 was added 48 hours after inoculation and DEX, at concentrations of 0.1, 1 and 10 μM, was then added 24 hours later. DEX was also added to cultures without RU-486 as controls. For conditions with and without RU-486, the normalized total sialic acid content and normalized N-linked sialylated species fraction induced by DEX are shown in FIG. 4A and FIG. 4B, respectively. The ability of DEX to enhance product sialylation was substantially reduced in the presence of 1 μM of RU-486 and was most evident for the 0.1 μM DEX condition. The total sialic acid content and N-linked sialylated species fraction for the 0.1 μM DEX conditions decreased from 15.1±0.1 and 92.2±2.0 (without RU-486) to 12.7±0.1 and 81.5±0.8 (with 1 μM RU-486), respectively. These results indicate that the mechanism through which DEX increased sialylation was GR-dependent, since RU-486 competes with DEX for the ligand-binding domain of the GR (Raux-Demay et al. 1990).

Application of DEX in Fed Batch Bioreactor Culture

Figure 5:
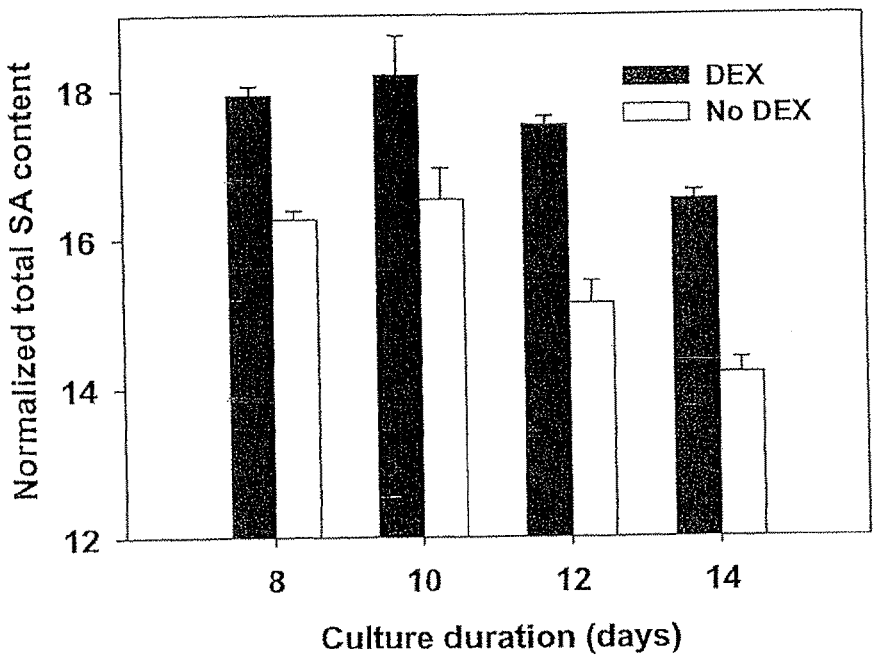
Figure 5:
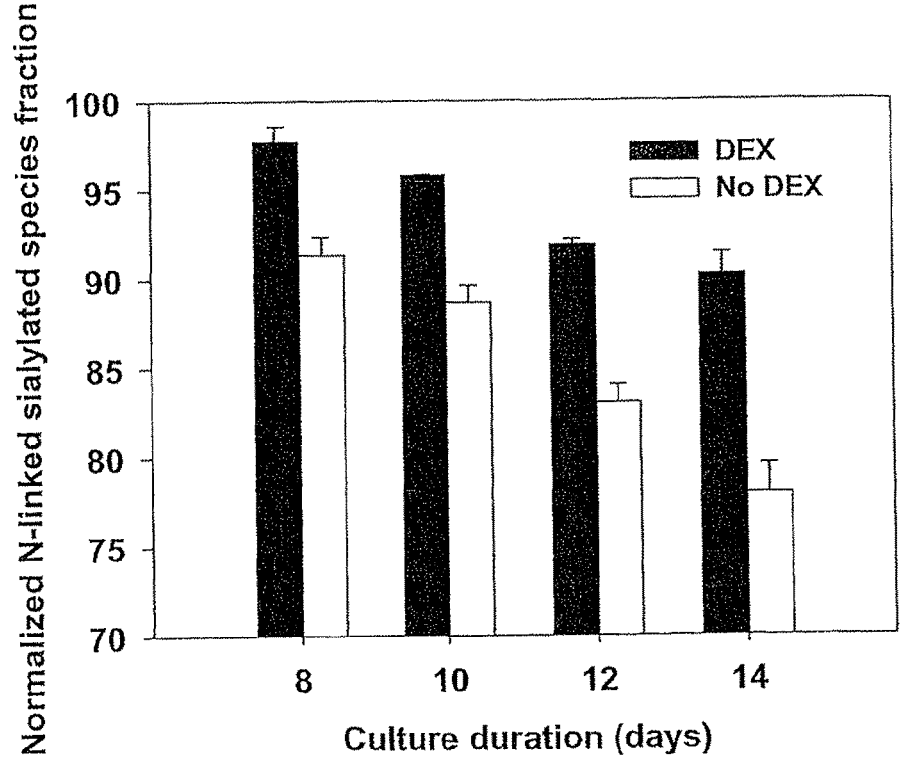

The effect of DEX to increase sialylation of fusion protein found in shake flasks was then tested in fed-batch cultures using controlled 5-L bioreactors. The bioreactors were operated as described in the methods section. Higher total sialic acid content (FIG. 5A) and N-linked sialylated species fraction (FIG. 5B) were observed in the cultures with 1 μM DEX bolus addition. The total sialic acid content with DEX was 16.5±0.1 compared to 14.2±0.1 for the control (16.2% increase). Similarly, the N-linked sialylated species fraction with DEX was 90.2±1.3 compared to 77.9±1.6 for the control (15.8% increase). In agreement with the observation in shake flask sialidase activity studies (FIGS. 3A and 3B), the total sialic contents decreased between days 8 to 14 from 17.9±0.1 to 16.5±0.1 (−7.8%) with DEX compared 16.3±0.1 to 14.2±0.1 (−12.9%) for the control. Similarly, the percentage of the sialylated fraction between days 8 to 14 decreased from 97.7±0.9 to 90.2±1.3 (−7.7%) with DEX compared to 91.3±0.9 to 77.9±1.6 (−14.7%) for the control.

Figure 6:
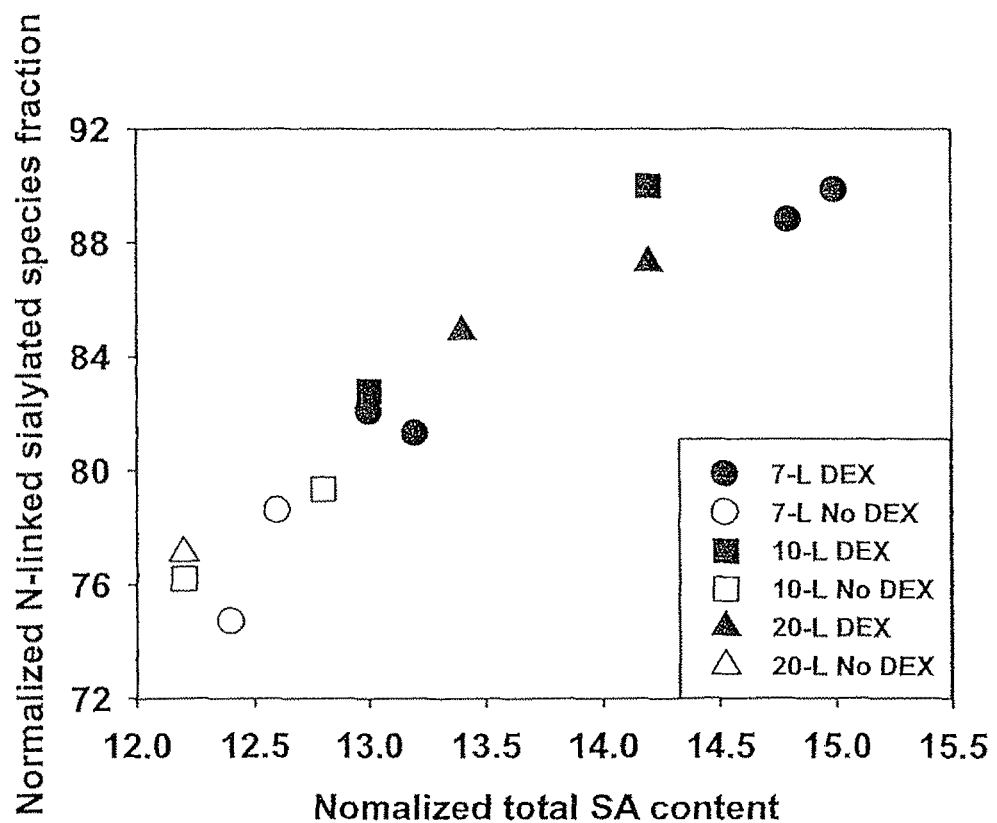

The increase in glycoprotein sialylation by DEX was further confirmed at various bioreactor scales. The normalized final sialic acid content, and normalized percentage of sialylated fractions from different runs are summarized in FIG. 6. Within these runs, the DEX condition included runs with DEX added as a bolus or included in the feed medium. As indicated in FIG. 6, DEX showed significant sialyaltion improvement with enhanced final sialic acid content (p value<0.001 by t-test) and final sialylated species fraction (p value<0.001 by t-test).

Conclusion

The addition of dexamethasone to a CHO culture producing a recombinant fusion glycoprotein resulted in improved sialylation. This study was the first to demonstrate that dexamethasone was capable of increasing expression of the glycosyltransferases α2,3-ST and β1,4-GT and that the effect of dexamethasone was mediated through the glucocorticoid receptors. Overall the effect of dexamethasone in improving sialylation involved both intracellular effects through the glycosylatransferases as well as extracellular effects through extending culture viability which decreased the presence of sialidases released into the culture supernatant through cell lysis. Dexamethasone was found to be a convenient method for improvement of sialylation.

Example 2

Cell Line and Medium

The CHO cell line used in this study was originally subcloned from DG44 parental cells and cultured in a protein-free proprietary growth medium. The host cells were genetically engineered to secrete an IgG-fusion protein under the control of CMV promoter.

Shake Flask Experiments

The experiments were carried out in 250-mL shake flasks (VWR international) with starting volumes of 100 mL and initial cell densities of $6\times10^5$ cells/mL. Shake flasks were placed on a shaker platform (VWR international) at 150 rpm rotating speed. Cells were cultured under standard humidified condition at 37° C. and 6% CO2, for a ten-day duration with daily pH adjustment using 1M sodium carbonate, and fed with glucose and glutamine every two days in order to maintain them at certain level. Cell density, cell viability and substrates/metabolites were offline-analyzed by an automated cell counting system Cedex (Innovatis AG, Bielefeld, Germany) and a Bioprofile Analyzer 400 (Nova Biomedical Corporation, Waltham, Mass.). Supernatant from each culture harvest was collected for SEC analysis.

Size-Exclusion Chromatography (SEC)

SEC analysis was performed according to the previously published method (Perico et al., 2008) with some modifications. Briefly, the Protein-A purified samples were run on an Agilent 1100 HPLC system (Agilent Technologies, Inc., Palo Alto, Calif.) on Tosoh Bioscience TSK-Gel G3000 SWxl column (7.8 ID×30 cm, 5 µm particles). The mobile phase contained 1× Phosphate Buffered Saline (PBS) at pH 7.4. The flow rate was 0.5 mL/min, and column temperature was controlled at 25° C. The signal was monitored by absorbance at wavelength of 280 nm.

Western Blot Analysis of Glutathione Reductase and Glucocorticoid Receptor

After being washed with 1×PBS, approximately $10^7$ CHO cells were lysed with 1 mL of Laemmli sample buffer (Bio-Rad Laboratories) and denatured at 90° C. for 5 minutes. The whole cell lysates were separated on a 4-15% SDS-polyacrylamide gel, blotted to 0.45 µm nitrocellulose membranes (Bio-Rad Laboratories), and probed with primary antibodies and secondary antibody. The primary antibody for detection of glutathione reductase was the monoclonal antibody raised against amino acids 391-510 mapping near the C-terminus of glutathione reductase of human origin (Santa Cruz Biotechnology, Santa Cruz, Calif.). Although Chinese hamster origin was not listed by the manufacturer for detection of glutathione reductase using this antibody, a preliminary experiment showed that there was only one band detected in the lysates from both CHO cells and human origin HL60 cells with an identical apparent molecular size on the blot. The primary antibody used for detection of glucocorticoid receptor was anti-human monoclonal antibody (Santa Cruz Biotechnology, Santa Cruz, Calif.). The secondary antibody was horseradish peroxidase (HRP)-conjugated anti-mouse antibody (Santa Cruz Biotechnology, Santa Cruz, Calif.). Membranes were stripped and re-probed with β-actin antibody (Santa Cruz Biotechnology) and HRP-conjugated secondary antibody. Immunodetection was performed with the enhanced chemiluminescence Western blotting detection system (GE Healthcare) and visualized with VersaDoc Imaging System (Bio-Rad Laboratories).

Results

Figure 7:
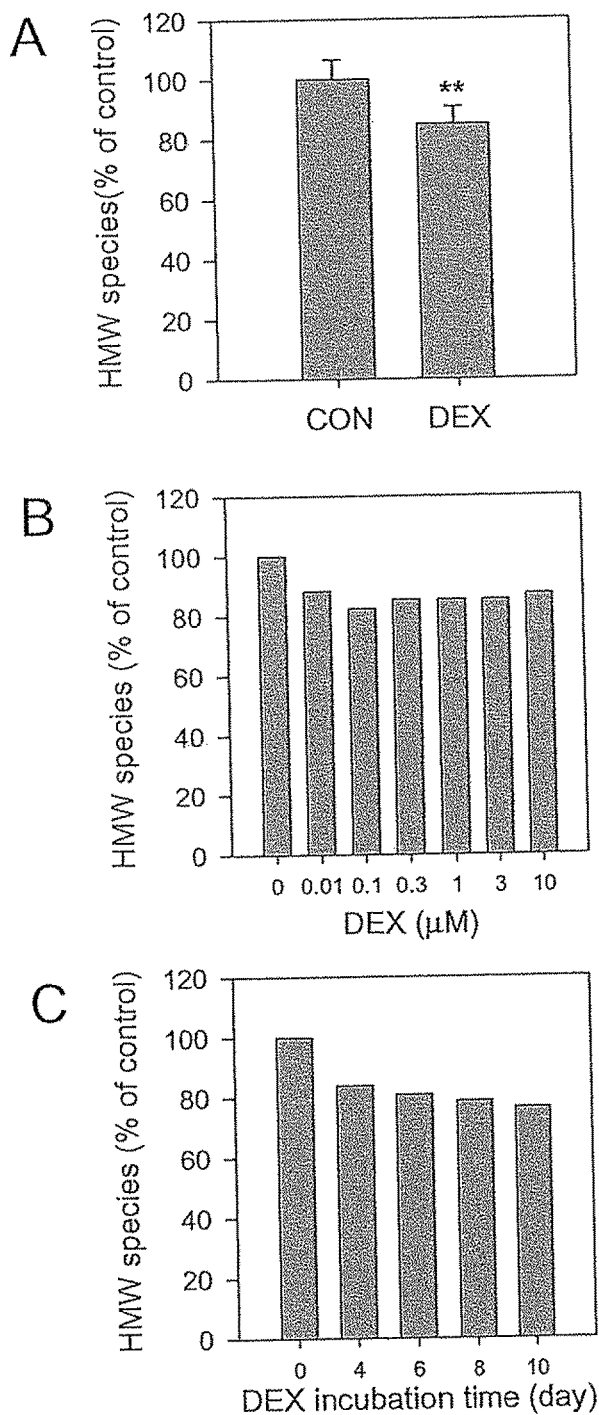
Figure 8:
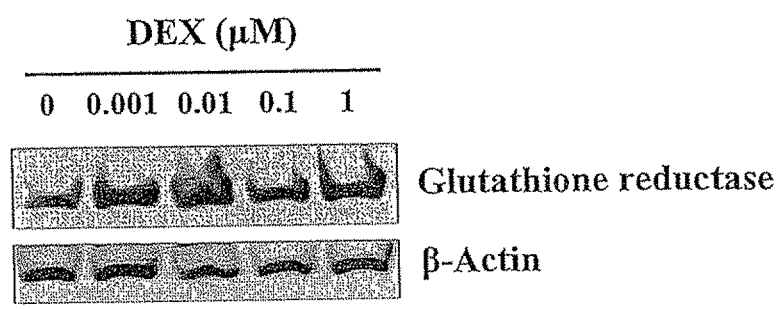
Figure 11:
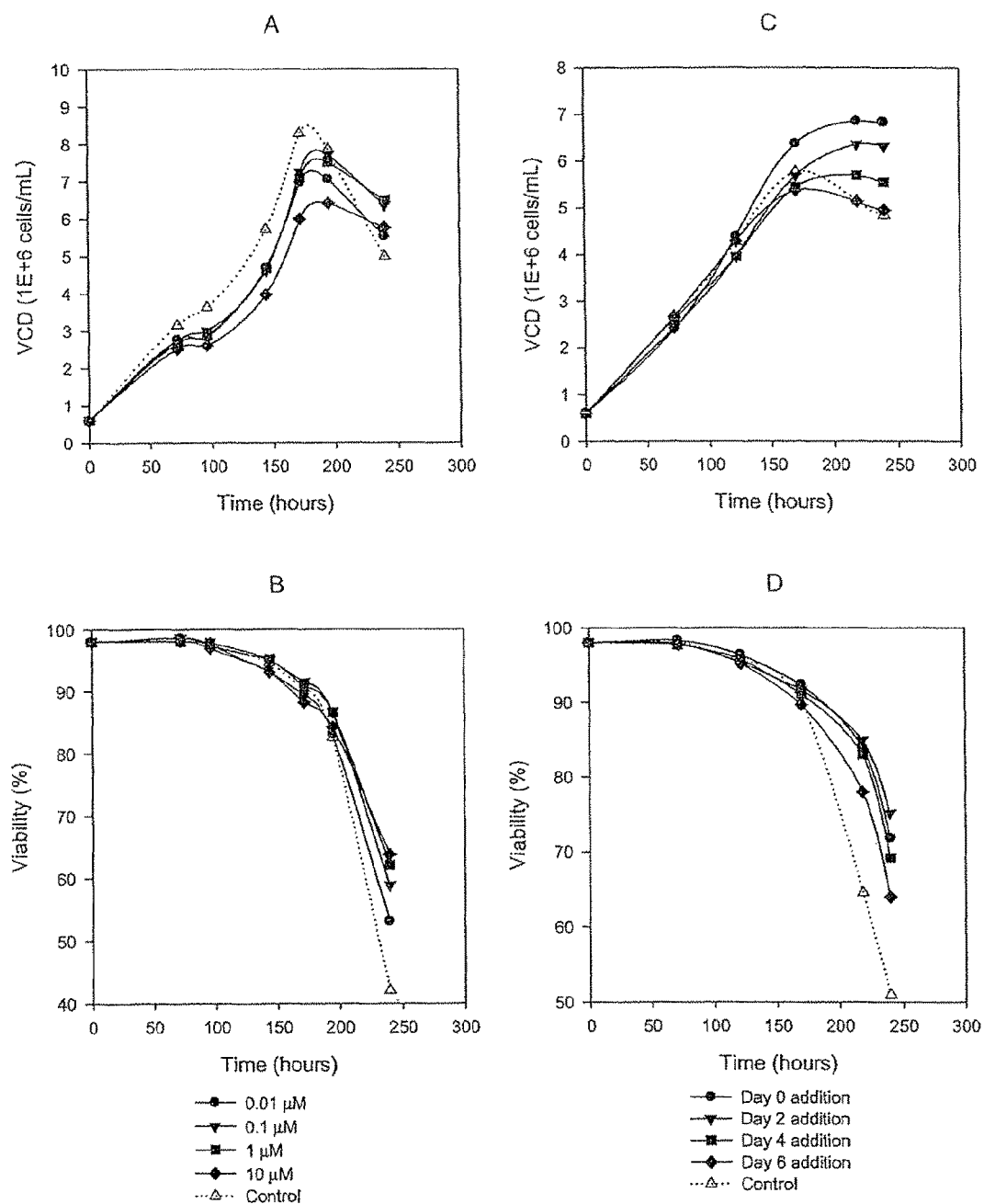

Dexamethasone (DEX) Reduces Aggregation of Cho-Produced IgG-Fusion Proteins at Broad Range of Concentrations FIG. 7A shows the significantly reduced percentage of high molecular weight (HMW) species in IgG-fusion protein after the CHO cells were treated with DEX at 1 µM final concentration in culture medium. The main components of HMW species were dimers and trimers formed covalently or non-covalently and categorically considered to be protein aggregates. Considering that a 15% reduction of protein aggregation was obtained under the culture conditions that had been already optimized, the improvement was practically significant in manufacture process. To establish the dose-response curve and time-course for the effects of DEX on protein aggregation, we cultured the cells either at different concentration of DEX or at the same concentration (1 µM) but with different incubation time. As shown in FIG. 7C, DEX time-dependently reduced the rate of protein aggregation, which was consistent with previously observed time-dependency of DEX on the improvement of cell viability and protein glycosylation profiles (Table 1 and FIG. 11). However, the concentration-dependency of DEX on reduction of protein aggregation level was not obvious (FIG. 7B), which suggests that the anti-aggregation effect was not simply due to the improved cell viability because our previous results demonstrated the viability of CHO cells was increased with the concentration of DEX from 0.01 µM to 10 µM in the culture medium Dexamethasone Up-Regulates Glutathione Reductase Expression in CHO Cells A Western Blot was performed to detect glutathione reductase expression in the whole cell lysates prepared from the CHO cells treated with various concentrations of DEX. As shown in FIG. 8, DEX increased the expression of glutathione reductase, which could be seen even when the drug was at 1 nM. Detection of β-actin was used for sample loading comparison to eliminate the possibility that the glutathione reductase band enhancement was due to the coincidentally increased sample loading.

GSH Reduces Purified IgG-fusion Protein Aggregation In Vitro

Figure 9:
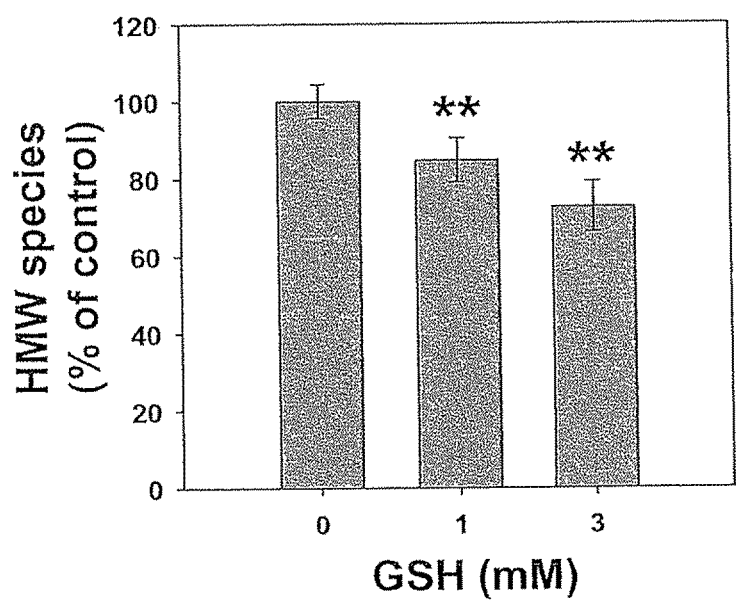

To determine if GSH itself could affect protein aggregation by directly interacting with the proteins, we did in vitro study by adding GSH to Protein-A purified IgG-fusion proteins that were reconstituted in Tris-acetate buffer, and analyzed SEC profiles. As shown in FIG. 9, the percentage of high molecular weight species was significantly decreased, with the reduction rate being 15.3% and 27.3% in the presence of 1 and 3 mM GSH respectively. The data clearly demonstrated that GSH could directly inhibit IgG-fusion protein aggregation.

Dexamethasone Effects are Mediated Via Glucocorticoid Receptors

DEX is a potent glucocorticoid with broad pharmacological actions. To determine if the inhibitory effect of DEX on IgG-fusion protein aggregation was specifically mediated through activation of glucocorticoid receptors, it was first confirmed that there is endogenous expression of glucocorticoid receptors (GR) in the cell line utilized, which is presented in FIG. 10A. Since the antibody used in the Western Blotting was raised against the conserved region of human GR, a whole-cell lysate sample of HepG-2 cells was also loaded as human origin sample for antibody validation purpose. Although the antibody could detect both GRα and GRβ, the present analysis only showed a single band. This could be because the molecular weights of these two isoforms (95 kDa vs 90 kDa) were too close to be separated on the 5-15% gradient gel or more likely because there was only one isoform presented in the samples.

Figure 10:
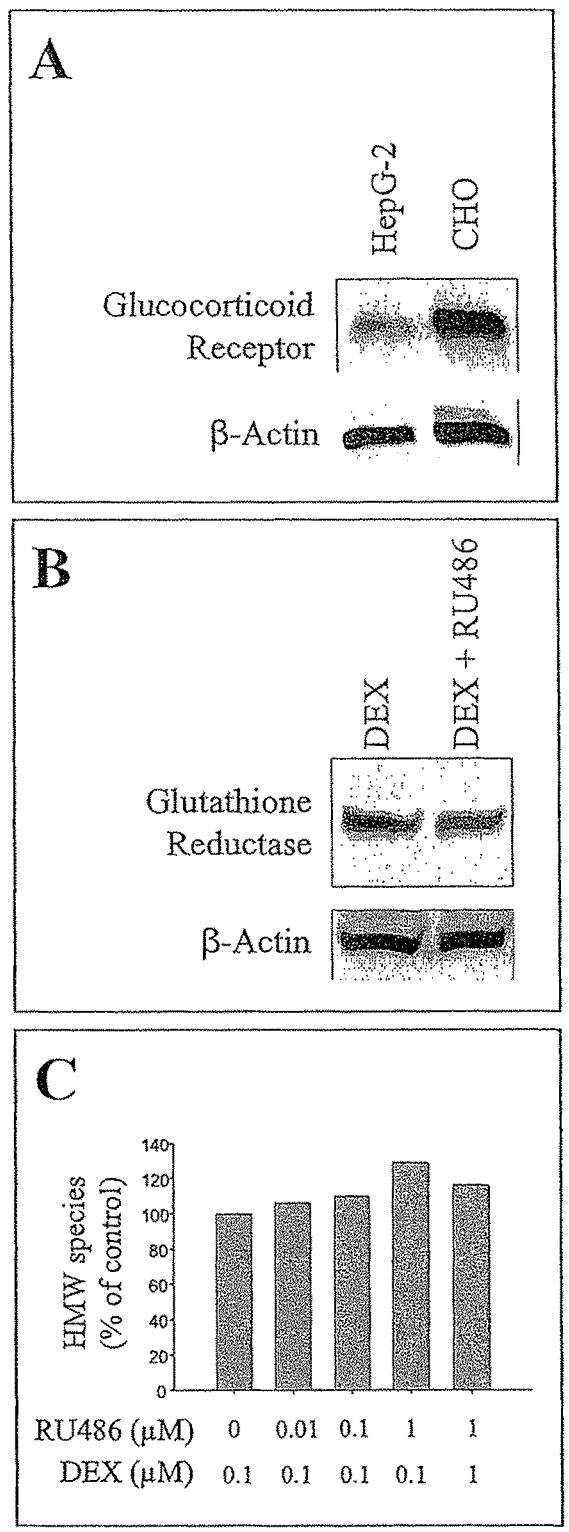

Since DEX was found to up-regulate glutathione reductase expression in CHO cells (see FIG. 8), a further assessment to determine if this effect was induced by the activation of GR receptors. RU-486 is a GR antagonist and often used as a tool drug in many GR related studies. Our preliminary experiment showed that RU-486 did not affect the CHO cell viability and metabolic parameters if the concentrations were not higher than 1 µM; at 10 µM, a significant decrease in cell viability and cell growth rate was observed. In the subsequent experiments, RU-486 was therefore used at 1 µM or lower concentrations and it was introduced into the culture to pre-treat CHO cells one day before DEX addition. FIG. 10B shows that in the presence of 1 µM RU-486, the up-regulatory effect of DEX on glutathione reducatase expression was attenuated, confirming the involvement of GR.

Finally, the percentages of HMW species in IgG-fusion proteins produced by CHO cells treated with 0.1 μM DEX and its combination with different concentrations of RU-486 was evaluated. Consistent with the result in FIG. 7B, the percentage of HMW species was decreased by approximately 17% when the culture was treated with 0.1 μM DEX alone, and this effect was gradually diminished with increasing concentrations of RU-486 (FIG. 10C). Under the condition that equal concentration of DEX and RU-486 was used, the inhibition rate of HMW species was about half of the rate obtained from DEX alone, indicating that DEX as an agonist and RU-486 as an antagonist had similar affinities to compete with each other for GR in CHO cells. Thus, taken all three pieces of data in FIG. 9 together, the results clearly demonstrated that the inhibition of IgG-fusion protein aggregation was mediated through GR.

Conclusion

As an inexpensive but potent glucocorticoid and with its beneficial triad, improving cell viability as described in Example 3 and glycosylation as described in Example 1 and inhibiting protein aggregation as described herein, dexamethasone may provide a simple, cost effective and efficient way to overall enhance cell culture process Example 3

This study, for the first time, demonstrated that dexamethasone is capable of preventing CHO cell apoptosis in serum-free condition in a concentration- and time-dependent manner. DEX induces CHO cell GILZ (glucocorticoid-induced leucine zipper) gene expression. DEX was successfully used in 10-L bioreactor CHO culture to improve cell viability and Fc-fusion protein productivity and sialic acid content. This study demonstrated the application of DEX in industrial cell culture to improve recombinant protein productivity and glycosylation.

Cell Line and Medium

The CHO cell line used in this study was subcloned from DG44 parental cells and cultured in a proprietary chemically-defined growth medium.

Shake Flask Experiments

The experiments were carried out in 250-mL shake flasks (VWR international) with starting volumes of 100 mL and initial cell densities of $6 \times 10^5$ cells/mL. The cultures were placed on a shaker platform (VWR international) at 150 rpm and maintained at 37° C. and 6% $CO_2$ for ten days. The cultures were sampled daily and the pH adjustment using 1M sodium carbonate, and fed with glucose and glutamine every two days in order to maintain them at certain levels. Cell density and viability were measured off-line a Bioprofile Analyzer 400 (Nova Biomedical Corporation, Waltham, Mass.).

Bioreactor Operation

Bioreactor experiments were performed in 10-L bioreactors (Sartorius Stedim Biotech, France) with starting working volumes of 5 L. Agitation, pH and dissolved oxygen were controlled at 150 rpm, 7.05, and 50% air saturation, respectively. Temperature was initially controlled at 37° C. and was shifted to lower temperature during the culture to extend the culture viability. The bioreactors were operated in a batch fed mode and were fed daily starting on day 3 with the proprietary feed medium to maintain adequate concentrations for glucose and other nutrients. Samples were taken during the cell culture process and analyzed for cell density, cell viability, substrates and metabolites.

qRT-PCR Analysis

TaqMan® 5'-nuclease real-time quantitative RT-PCR assay was performed to verify the upregulation of GILZ by DEX. Total RNA, purified from each triplicate culture with and without 1 μM DEX using the RNeasy® midi kit as described above. Purified RNA was treated with RNasefree DNaseI (Qiagen) and then used as a template to synthesize the first-strand cDNA using $RT^2$ First Strand Kit (SA Biosciences, Frederick, Md.). Expression of GILZ was quantitatively determined using GILZ specific TaqMan MGB probe (6-FAM-AGAGGACTTCACGTGT) (SEQ ID NO: 7)and primers (Forward: 5-CCTCCCTCATCTGTC-CACTGA-3 (SEQ ID NO: 8)and Reverse: 5-TG-GTGGGTTTGGCATTCAA-3) (SEQ ID NO: 9)). 20 ng of cDNA was amplified using 900 nM primers and 250 nM probe in 1× TaqMan Fast Universal PCR Master Mix (Applied Biosystems, Carlsbad, Calif.). Reactions were run in triplicate on the Applied Biosystems 7500 Fast Real-Time PCR System using the universal cycling parameters (20 s 95° C., 40 cycles of 3 s 95° C., 30 s 60° C.). Parallel reactions were set up on the same plate analyzing β-Actin in each sample as an endogenous control. The threshold cycle of each gene was normalized against the threshold cycle of "housekeeping gene" β-Actin. Normalized changes in gene expression with respect to the control were calculated using delta-delta threshold cycle method (Livak and Schmittgen, 2001).

Western Blot Analysis of GILZ

Approximately $10^7$ CHO cells were washed with 1× phosphate buffered saline (PBS) solution, lysed with 1 mL of Laemmli sample buffer (Bio-Rad Laboratories, Hercules, Calif.), and then denatured at 90° C. for 5 minutes. The whole cell lysates were separated on a 4-15% SDS-polyacrylamide gel, blotted to 0.45 μm nitrocellulose membranes (Bio-Rad Laboratories), and probed with a primary mouse monocolonal antibody directed to GILZ (Santa Cruz Biotechnology, Santa Cruz, Calif.), followed by a horseradish peroxidase (HRP)-conjugated anti-mouse secondary antibody (Santa Cruz Biotechnology). Membranes were stripped and re-probed with β-actin antibody (Santa Cruz Biotechnology) and an HRP-conjugated anti-mouse secondary antibody. Immunodetection was performed with the enhanced chemiluminescence Western blotting detection system (GE Healthcare UK Limited Little Chalfont, Buckinghamshire, UK) and visualized with a VersaDoc Imaging System (Bio-Rad Laboratories, Hercules, Calif.).

Titer Assay

Titer was determined by affinity chromatography using an HPLC pump and UV detection (Agilent Technologies, Santa Clara, Calif.) and Applied Biosystems Poros A/20 Protein A column (100×4.6 mm). The eluted protein was quantified using a 10-level standard curve.

Results

Effect of Dexamethasone on CHO Cell Growth

The glucocorticoid dexamethasone (DEX) was added to shake flask cultures at final concentrations between 0.01 to 10 μM two days after inoculation to assess the effects of glucocorticoids on CH cell viability and the potential to extend the cell culture period. The viable cell density (VCD) profile in the dose-response study (FIG. 11A) shows increasing inhibition of cell growth occurring one day after DEX treatment in a dose-dependent manner. The peak VCD reached $8.5 \times 10^6$ cells/ml in the untreated control culture, whereas the peak VCD was $6.5 \times 10^6$ cell/mL in the cultures treated with 10 μM DEX. Cell viability decreased rapidly after Day 6 (FIG. 11B) and percent viability on day 10 was only 42.1%. In contrast, the final cell viabilities with 0.01 µM, and 10 µM DEX were 53.1% and 64.0%, respectively. The loss of viability beginning on day 6 improved in a concentration-dependent manner in the DEX-treated cultures, with a maximal effect at 10 µM (FIGS. 11A and 11B).

A time-course study for the addition of DEX was then performed in shake flask cultures in which DEX was added to a final DEX concentration of 1 µM and added between the day of inoculation through the sixth day after inoculation. As shown in FIGS. 11C and 11D, the final VCD and cell viability increased in all DEX-treated cultures, and both VCD and cell viability improved in a time-dependent manner with earlier DEX addition timing. The viability of untreated CHO cell cultures decreased to 50% on day 10, while cultures in which DEX was added on days 0, 2, 4 and 6 were 63, 68, 72 and 74%, respectively.

DEX Reduces Cell Specific Growth Rate but Increases Cell Specific Productivity

Figure 12:
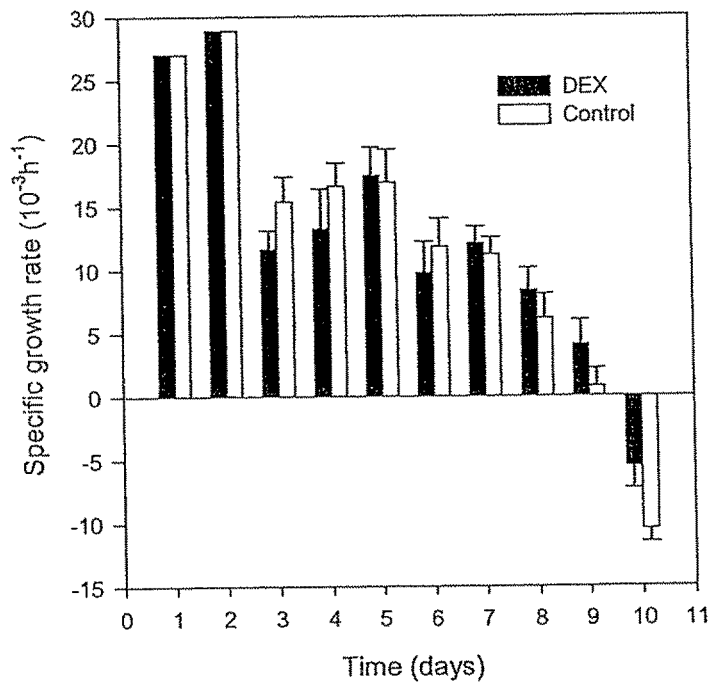
Figure 12:
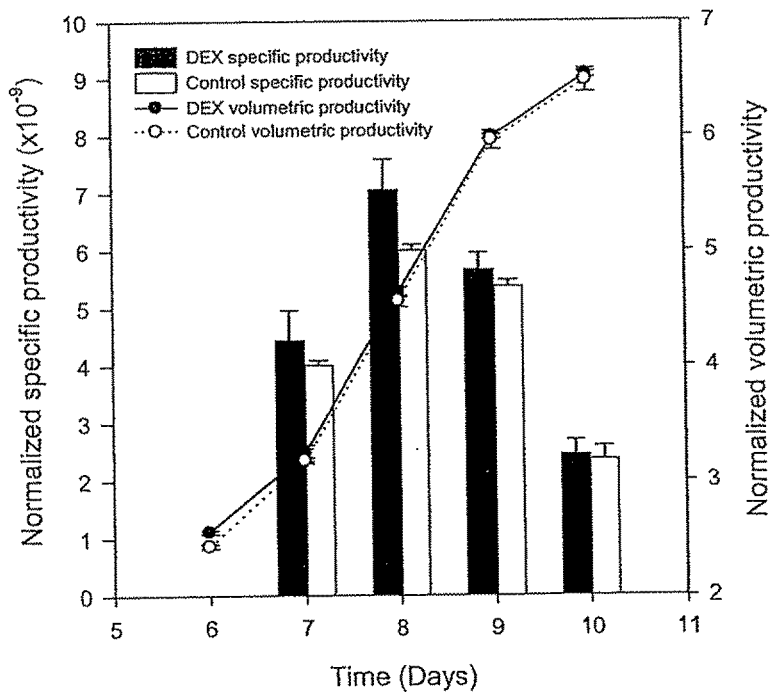

The specific growth rate, normalized volumetric productivity, and normalized cell specific productivity were quantified and compared between DEX-treated and untreated cells. The data comparing the specific cell growth rates and normalized productivity profiles with and without 1 µM DEX are shown in FIGS. 12A and 12B (n=5). DEX was added on day 2, resulting in approximately a 30% reduction in cell growth rates with DEX compared to control the day after DEX addition. However, this growth inhibition effect decreased with the culture time. At the end of the culture period, cell death rates were slower in cultures with DEX treated cells. Moreover, the early cell growth inhibition induced by DEX did not affect volumetric productivity (6.5 for all cultures); however, cultures with DEX treatment had significantly higher specific productivity than untreated cells, with a maximum specific productivity of $(7.0\pm0.6)_{x10}{}^{-9}$.

Upregulation of GILZ by DEX was Confirmed by qRT-PCR and Western Blot Analysis

Figure 13:
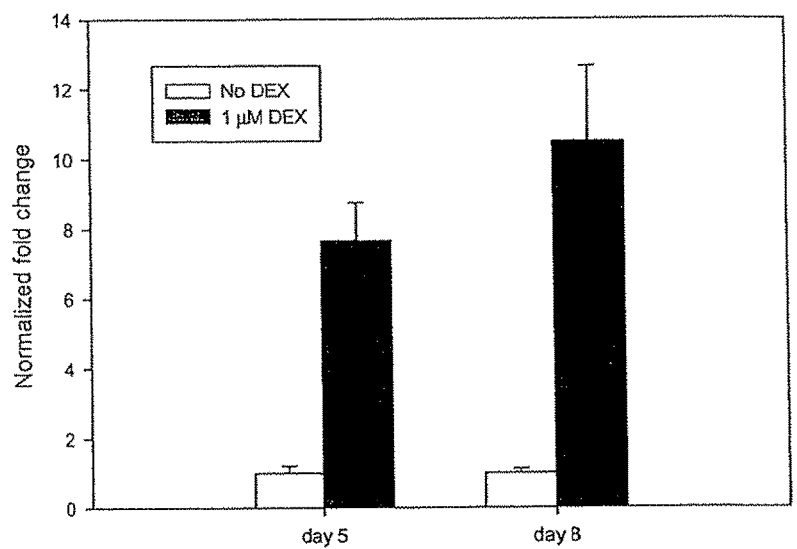
Figure 13:
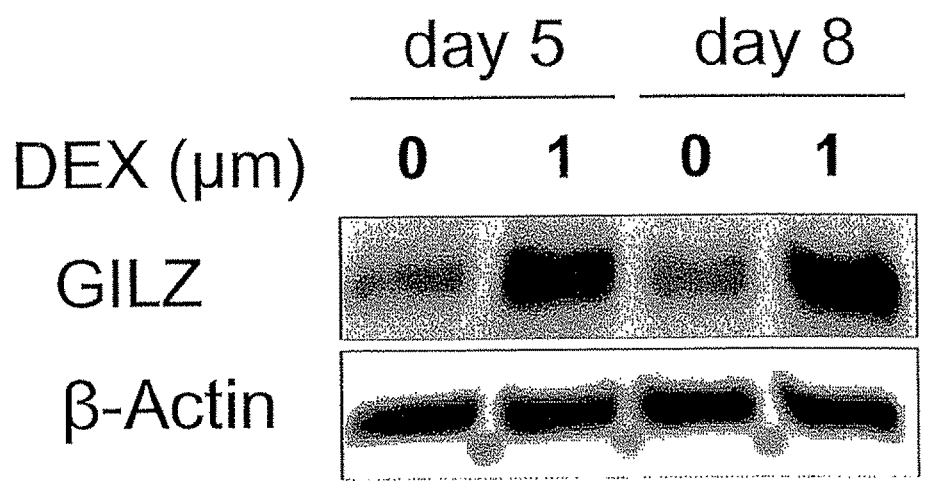

GILZ was analyzed using qRT-PCR to validate the gene expression profiles obtained by microarray analysis. RNA samples from day 5 and 8 for triplicate DEX treated and untreated cultures were applied in TaqMan® qPCR quantification. Parallel reactions were set up on the same plate analyzing 13-Actin in each sample as an endogenous control. As shown in FIG. 13A, the normalized expression profile changes of GILZ obtained by qRT-PCR on day 5 and day 8 samples are 7.66±1.08 and 10.48±2.16, respectively.

Cell lysates from day 5 cultures with and without 1 µM DEX treatment were analyzed by Western blotting to test the whether GILZ is overexpressed in DEX treated cultures. The blot was also reprobed with the beta-actin antibody as a control to assess equivalent gel loading. As shown in FIG. 13B, the expression of GILZ protein significantly increased in the DEX treated samples compared with untreated samples. In addition, GILZ fold change caused by DEX is slightly higher in day 8 samples than day 5 samples, which is in agreement with the qRT-PCR results.

Comparison of Dexamethasone with Other Two Glucocorticoids, Hydrocortisone and Prednisolone Experiments in shake flasks then tested whether the protective effect of DEX on CHO cell viability was limited to DEX or could be extended to other glucocorticoid compounds, such as hydrocortisone (HYC) and prednisolone (PRD). DEX, HYC and PRD (Sigma-Aldrich, St. Louis, Mo.) were added two days after inoculation at final concentrations of 0, 0.1, 1 and 10 µM for each of these three compounds. Peak VCD, final VCD and final viability of cultured cells are presented in Table 2.

TABLE 2

| | Treatment Concentration (µM) | Peak VCD (×10$^6$ cells/mL) | Final VCD (×10$^6$ cells/mL) | Viability (%) |
|---|---|---|---|---|
| Dexamethasone (DEX) | 0.1 | 7.99 | 7.64 | 72.3 |
| | 1 | 9.02 | 8.40 | 75.8 |
| | 10 | 7.49 | 7.38 | 82.3 |
| Hydrocortisone (HYC) | 0.1 | 10.06 | 7.86 | 60.1 |
| | 1 | 9.51 | 8.15 | 65.1 |
| | 10 | 8.44 | 7.80 | 75.5 |
| Prednisolone (PRD) | 0.1 | 8.99 | 8.26 | 69.4 |
| | 1 | 9.25 | 8.79 | 76.8 |
| | 10 | 8.05 | 8.27 | 77.5 |
| Control | N/A | 8.69 | 7.56 | 56.6 |

Similar to DEX, HYC (60.1-75.5% final viability) and PRD (69.4-75.5% final viability) also showed dose-dependent cell protective effects. Viability on day 10 was 56.6% for the control compared to day 10 viabilities with 0.1 and 10 µM concentrations for DEX of 72.3% and 82.3%; for HYC of 60.1% and 75.5%; and PRD of 69.4% and 77.5%, respectively. Thus all three glucocorticoid compounds improved culture viability with maximum effects at 10 µM for all three glucocorticoid compounds.

Figure 14:
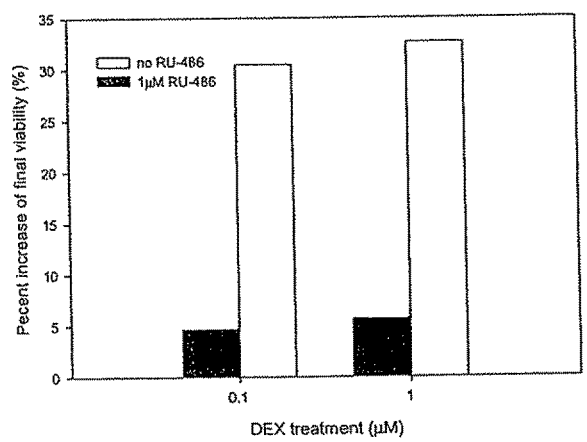
Figure 14:
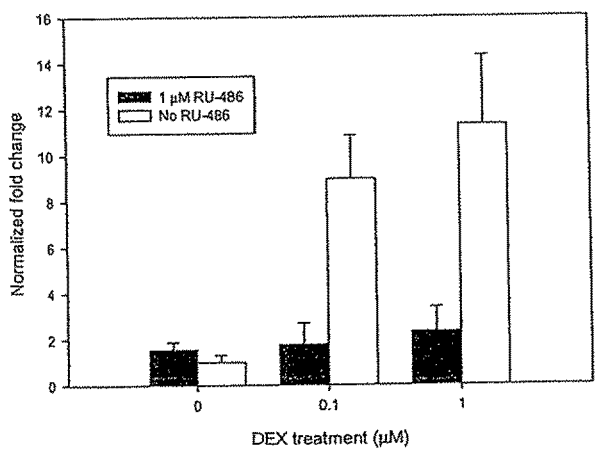
Figure 14:
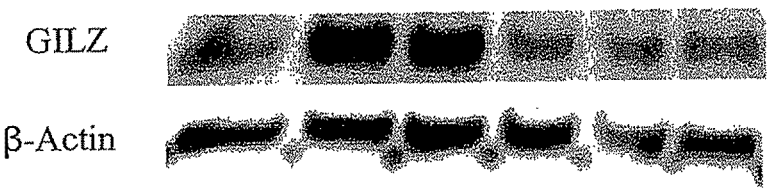

The Death-Suppression Action of Dexamethasone Involves GILZ and Glucocorticoid Receptor In order to determine whether the viability improvement from DEX addition was mediated through GILZ and the glucocorticoid receptor (GR), the GR antagonist mifepristone (RU-486) was added to cell culture medium before DEX treatment. For conditions with and without RU-486, the percent increase of final cell viability induced by DEX is shown in FIG. 14A. The ability of DEX to improve cell viability was substantially reduced in the presence of 1 µM of RU-486. The percent increase of cell viability induced by 0.1 and 1 µM DEX decreased from 30.5% and 32.6% (without RU-486) to 4.7% and 5.7% (with 1 µM RU-486), respectively. In the mean time, qRT-PCR analysis (FIG. 14B) shows that in the presence of 1 µM RU-486, the upregulation effect of DEX on GILZ expression was significantly attenuated. The fold change induced by 0.1 and 1 µM DEX decreased from 9.0±1.9 and 11.3±3.0 (without RU-486) to 1.8±0.9 and 2.3±1.0 (with 1 µM RU-486), respectively. Western Blotting analysis (FIG. 14C) further confirmed the overexpression of GILZ protein was significantly decreased in the presence of 1 µM RU-486. These results indicate that the mechanism through which DEX increased viability involved GILZ and was GR-dependent, since RU-486 competes with DEX for the ligand-binding domain of the GR Application of Dexamethasone in 10-L Fed Batch Bioreactor Culture Fed-batch cultures in 10-L bioreactors were carried out to determine whether the effect of DEX seen in shake flasks would scale to bioreactors. The overall goal of DEX was to suppress cell death, extend culture longevity and consequently increase glycoprotein production for a process in bioreactors. In this study, three bioreactors were operated using the same conditions described above; with 1 µM of DEX added to two bioreactors on day 2 or day 7 respectively. Different from shake flask runs, bioreactor runs were extended to 14 days, the culture temperature was shifted to a lower temperature during the late exponential phase of the culture, and a proprietary feeding medium was used instead of feeding only glucose and glutamine.

Figure 15:
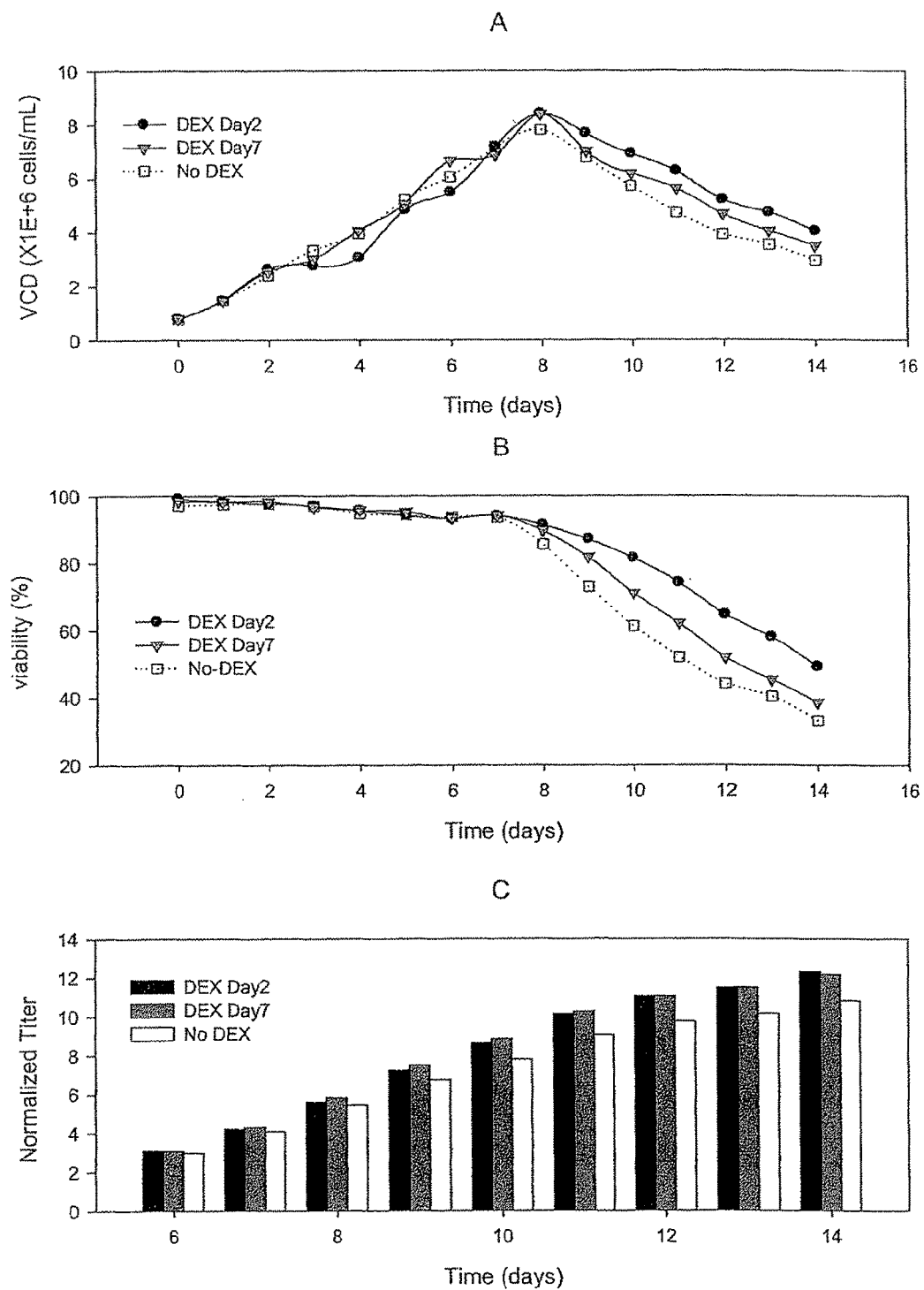

Bioreactors with DEX added on either day 2 or day 7 reached maximum cell densities of approximately $8.3 \times 10^6$ cell/mL on day 8, compared to $7.8 \times 10^6$ cell/mL without DEX (FIG. 15A). DEX addition decreased the cell death rate in the bioreactors. Cell viability was 94% viability for all conditions on day 6 (FIG. 15B). By day 14, the percent viability decreased to 29% without DEX, compared to 55% and 39% with DEX added on days 2 or 7, respectively. The final VCD on day 14 with DEX added on days 2 or 7 were 4.1 and $3.5 \times 10^6$ cell/mL respectively, compared to $2.8 \times 10^6$ cell/mL without DEX addition. Normalized protein titers were approximately 5.5 on day 7 prior to the maximum VCD (FIG. 15C). Thereafter, protein production during the stationary and death phases of the cultures was higher in the bioreactors with DEX addition. The day 14 harvest normalized titers were 12.5 in both bioreactors with DEX, compared to 10.5 without DEX addition, a 20% increase.

Conclusion

Our effort on medium optimization has led us to unexpectedly discover that glucocorticoids can significantly attenuate the cell viability decline in the fed-batch culture of CHO cells. In the mechanism study of this phenomenon, the involvement of upregulation of anti-apoptotic gene GILZ was identified through qRT-PCR and Western blot analysis. By studying effects of DEX's analogs and antagonist on CHO cell growth, the role of GILZ and glucocorticoid receptor in mediating the action of DEX was determined. Fed-batch bioreactor experiments demonstrates this glucocorticoid analog to be an effective, feasible, and cost-efficient chemical for attenuating the viability decline in cell cultures.

Example 4

In this study, the effects of dexamethasone (DEX) on CHO cell growth, protein sialylation and aggregation were studied on another CHO cell line with different glycoprotein (CTLA4Ig) secretion.
Cell Line and Medium
The CHO cell line used in this study was originally subcloned from DG44 parental cells and cultured in a proprietary chemical-defined growth medium.
Shake Flask Experiments
The experiments were carried out in 250-mL shake flasks (VWR international) with starting volumes of 100 mL and initial cell densities of $6 \times 10^5$ cells/mL. The cultures were placed on a shaker platform (VWR international) at 150 rpm and maintained at 37° C. and 6% $CO_2$ for ten days. The cultures were sampled daily and the pH was adjusted as needed using 1M sodium carbonate and fed with glucose and glutamine every two days in order to maintain them at adequate levels. The glucocorticoids dexamethasone (DEX) was added at final concentrations between 0.001-10 M on day 2. Cell density and viability were measured offline using a Cedex automated cell counter (Innovatis AG, Bielefeld, Germany). Culture pH and concentrations for glucose and glutamine were measured off-line using a Bioprofile Analyzer 400 (Nova Biomedical Corporation, Waltham, Mass.). Supernatants from culture harvests were collected for analysis of sialic acid content and HMW level.
Sialic Acid and HMW Content Assay
The sialic acid and HMW content assay were performed as described in the previous examples.

Results

Figure 16:
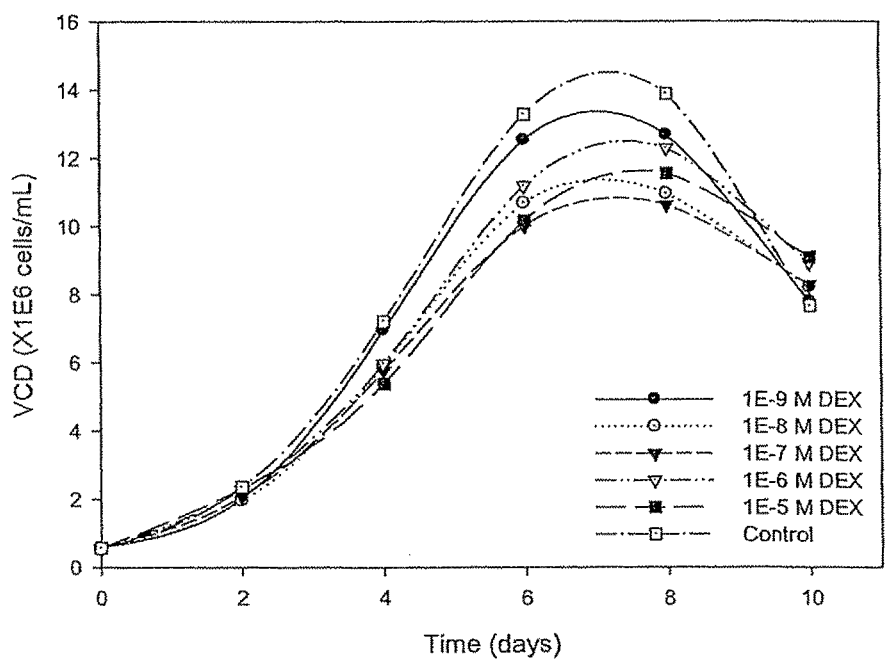
Figure 16:
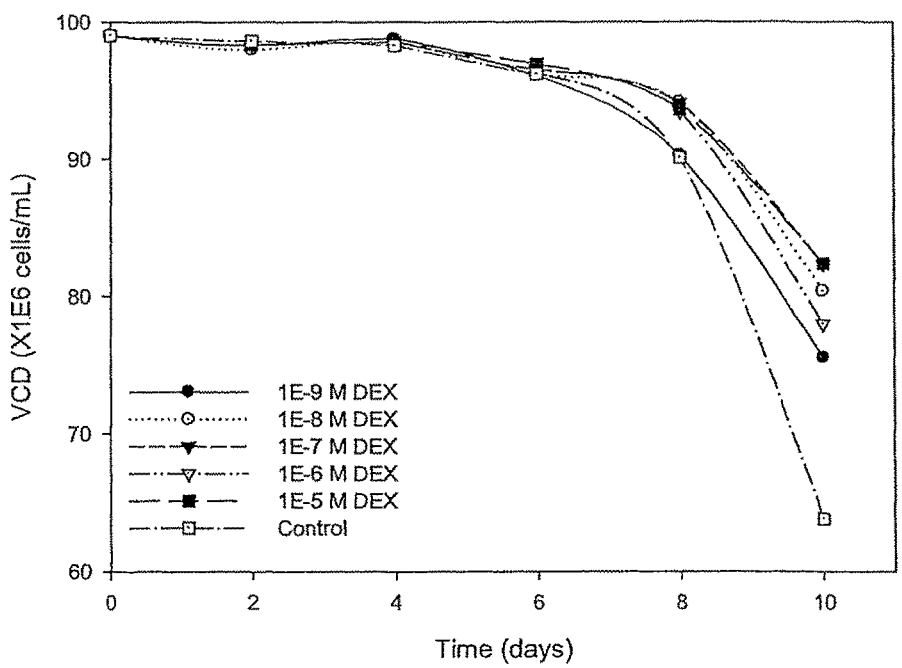

Effect of Dexamethasone on CHO Cell Growth
The glucocorticoid dexamethasone (DEX) was added to shake flask cultures at final concentrations between 0.001 to 10 µM two days after inoculation to assess the effects of DEX on CHO cell viability and the potential to extend the cell culture period. The viable cell density (VCD) profile in the dose-response study (FIG. 16A) shows increasing inhibition of cell growth occurring after DEX treatment, though the concentration dependency is not obvious in the studied range. The peak VCD reached $13.9 \times 10^6$ cells/mL in the untreated control culture, whereas the peak VCD ranged from $10.6 \times 10^6$ to $12.7 \times 10^6$ cells/mL in the cultures treated with 0.001 to 10 µM DEX. Cell viability for the untreated cultures decreased rapidly after Day 6 (FIG. 16B) and percent viability on day 10 was only 64.5%. In contrast, the final cell viabilities with 0.001 µM, and 10 µM DEX were 75.5% and 82.3%, respectively.

Figure 17:
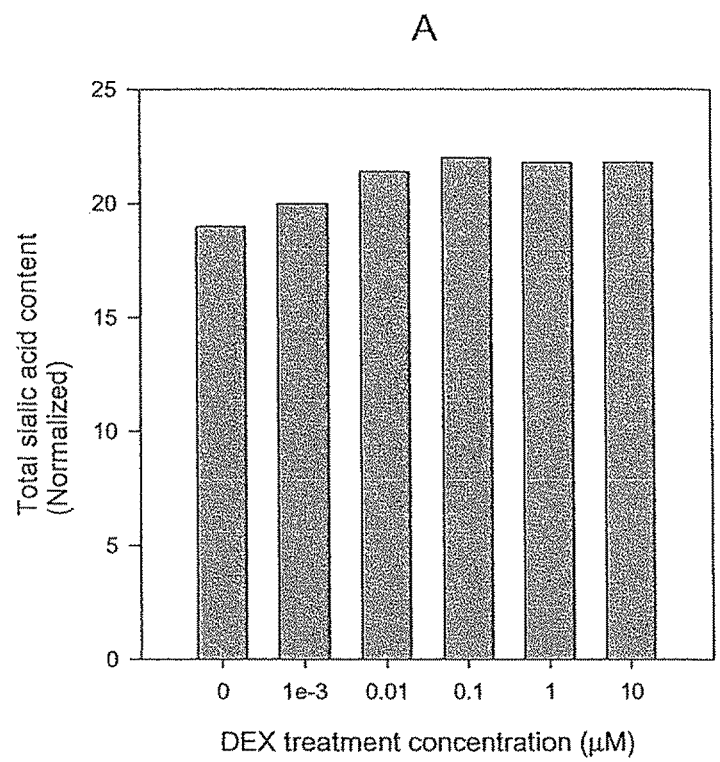
Figure 17:
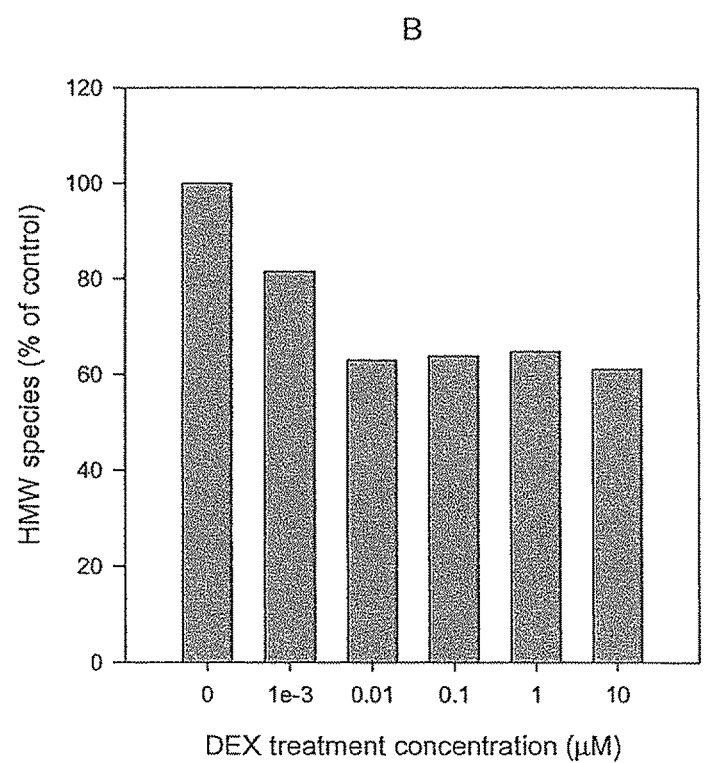

Dexamethasone (DEX) Increases Sialylation and Reduces HMW Level of Glycoprotein CTLA4Ig
Besides the cell growth, the effects of DEX on sialic acid content and HMW level were also assessed. Through comparing with untreated cultures, the percent increase of sialic acid content (FIG. 17A) and the percent reduction of HMW species (FIG. 17B) induced by various concentration of DEX are shown in FIG. 17. It is obviously that DEX is capable of increasing the sialylation and reducing the HMW species of glycoprotein, indicating improved protein quality, even at 0.001 µM concentration. The concentration-dependencies of DEX on sialic acid content and HMW species are not obvious as the concentration of DEX is above 0.01 µM.

These results demonstrated that the actions of DEX on cell viability improvement, glycoprotein sialylation improvement and aggregation reduction are not limited to either single cell cline or medium formulation.

Example 5

In this study, the feasibility of utilizing DEX in the cell culture medium for large scale recombinant glycoprotein production is demonstrated in 500-L and 5000-L scale bioreactors.
Cell Line and Medium
The CHO cell line used in this study was subcloned from DG44 parental cells and cultured in a proprietary growth medium.
Bioreactor Operation
Bioreactor experiments were performed in 7-L, 500-L and 5000-L bioreactors with starting working volumes around 3 L, 300 L and 3000 L, respectively. All the bioreactor runs started at 37° C. and shifted to lower temperature when cells entered production phase in order to extend the cell culture period. pH, and dissolved oxygen were maintained at 7.05, and 50% air saturation. Agitation rates for 7-L, 500-L and 5000-L scales are 180, 75 and 60 rpm respectively. All the bioreactor experiments were conducted in a fed batch mode with daily feeding of a protein-free medium in order to maintain the glucose and other nutrients at certain levels. Dexamethasone was included in the feed medium at all the production scales for the purpose of increasing cell viability and protein sialylation. Samples were taken during the cell culture process and analyzed for cell density, cell viability, substrates and metabolites.

The Titer, Sialic Acid and HMW Content Assay were Performed as Described in the Previous Examples.

Results

FIGS. 18A and 18B present the bioreactor performance with respect to cell growth and viability. The cell growth through scale up from 7-L to 5000-L was observed to have similar peak viable cell densities between 12 to 13×10$^6$ cells/mL with error bars representing the standard deviation of the runs at a particular scale overlapping at every time point. Cell densities peaked on Day 7 at 5000-L scale and at Day 8 for 7-L and 500-L scales. The Day 14 average viabilities of the cultures were 88%, 84%, and 91% at 7-L, 500-L, and 5000-L bioreactor scale, respectively. FIGS. 18C and 18D present the productivity and sialic acid profiles from 7-L, 500-L and 5000-L bioreactor scales. The Day 14 titers (reported as normalized value) were 13.2, 11.6, and 13.6 at 7, 500, and 5000-L scales, respectively. Peak sialic acid levels (reported as normalized value) were 16.0, 18.0 and 19.0 at increasing scales. The sialic acid dropped by approximately 2.6 units by the end of the runs for all scales.

CONCLUSION

Overall, with dexamethasone included in the feed medium performed well at all scales, indicating the feasibility of utilizing dexamethasone as medium additives for industrial scale production.

---

What is claimed is:

1. A cell culture process for the production of a recombinant CTLA4 molecule, comprising: a) culturing CHO cells which produce a recombinant CTLA4 molecule in cell culture under conditions that allow for protein production; and b) feeding the CHO cells with feeding medium containing dexamethasone, wherein the recombinant CTLA4 molecule comprises the extracellular domain of CTLA4 with the amino acid sequence beginning with methionine at position 27 or alanine at position 26 and ending at aspartic acid at position 150 as shown in SEQ ID NO: 2 joined to an immunoglobulin moiety comprising hinge, CH2 and CH3 domains and wherein the dexamethasone is sustained or maintained in the CHO cell culture at a concentration of 1 nM to 0.1 μM, and wherein the CHO cell culture volume is at least 500 liters.

* * * * *

UNITED STATES PATENT AND TRADEMARK OFFICE
CERTIFICATE OF CORRECTION

PATENT NO. : 9,540,426 B2
APPLICATION NO. : 12/897857
DATED : January 10, 2017
INVENTOR(S) : Jing et al.

Page 1 of 1

It is certified that error appears in the above-identified patent and that said Letters Patent is hereby corrected as shown below:

On the Title Page

Column 2
Line 3, after "BMC" insert -- Cell --.

Signed and Sealed this
Twentieth Day of February, 2018

Andrei Iancu
*Director of the United States Patent and Trademark Office*

SEQUENCE LISTING

<160> NUMBER OF SEQ ID NOS: 9

<210> SEQ ID NO 1
<211> LENGTH: 1152
<212> TYPE: DNA
<213> ORGANISM: Homo sapiens
<220> FEATURE:
<221> NAME/KEY: CDS
<222> LOCATION: (1)..(1149)

<400> SEQUENCE: 1

```
atg ggt gta ctg ctc aca cag agg acg ctg ctc agt ctg gtc ctt gca        48
Met Gly Val Leu Leu Thr Gln Arg Thr Leu Leu Ser Leu Val Leu Ala
1               5                  10                  15 ctc ctg ttt cca agc atg gcg agc atg gca atg cac gtg gcc cag cct        96
Leu Leu Phe Pro Ser Met Ala Ser Met Ala Met His Val Ala Gln Pro
                20                  25                  30 gct gtg gta ctg gcc agc agc cga ggc atc gct agc ttt gtg tgt gag       144
Ala Val Val Leu Ala Ser Ser Arg Gly Ile Ala Ser Phe Val Cys Glu
            35                  40                  45 tat gca tct cca ggc aaa gcc act gag gtc cgg gtg aca gtg ctt cgg       192
Tyr Ala Ser Pro Gly Lys Ala Thr Glu Val Arg Val Thr Val Leu Arg
        50                  55                  60 cag gct gac agc cag gtg act gaa gtc tgt gcg gca acc tac atg atg       240
Gln Ala Asp Ser Gln Val Thr Glu Val Cys Ala Ala Thr Tyr Met Met
65                  70                  75                  80 ggg aat gag ttg acc ttc cta gat gat tcc atc tgc acg ggc acc tcc       288
Gly Asn Glu Leu Thr Phe Leu Asp Asp Ser Ile Cys Thr Gly Thr Ser
                85                  90                  95 agt gga aat caa gtg aac ctc act atc caa gga ctg agg gcc atg gac       336
Ser Gly Asn Gln Val Asn Leu Thr Ile Gln Gly Leu Arg Ala Met Asp
                100                 105                 110 acg gga ctc tac atc tgc aag gtg gag ctc atg tac cca ccg cca tac       384
Thr Gly Leu Tyr Ile Cys Lys Val Glu Leu Met Tyr Pro Pro Pro Tyr
            115                 120                 125 tac ctg ggc ata ggc aac gga acc cag att tat gta att gat cca gaa       432
Tyr Leu Gly Ile Gly Asn Gly Thr Gln Ile Tyr Val Ile Asp Pro Glu
        130                 135                 140 ccg tgc cca gat tct gat cag gag ccc aaa tct tct gac aaa act cac       480
Pro Cys Pro Asp Ser Asp Gln Glu Pro Lys Ser Ser Asp Lys Thr His
145                 150                 155                 160 aca tcc cca ccg tcc cca gca cct gaa ctc ctg ggt gga tcg tca gtc       528
Thr Ser Pro Pro Ser Pro Ala Pro Glu Leu Leu Gly Gly Ser Ser Val
                165                 170                 175 ttc ctc ttc ccc cca aaa ccc aag gac acc ctc atg atc tcc cgg acc       576
Phe Leu Phe Pro Pro Lys Pro Lys Asp Thr Leu Met Ile Ser Arg Thr
                180                 185                 190
```

```
cct gag gtc aca tgc gtg gtg gtg gac gtg agc cac gaa gac cct gag      624
Pro Glu Val Thr Cys Val Val Val Asp Val Ser His Glu Asp Pro Glu
        195                 200                 205 gtc aag ttc aac tgg tac gtg gac ggc gtg gag gtg cat aat gcc aag      672
Val Lys Phe Asn Trp Tyr Val Asp Gly Val Glu Val His Asn Ala Lys
    210                 215                 220 aca aag ccg cgg gag gag cag tac aac agc acg tac cgg gtg gtc agc      720
Thr Lys Pro Arg Glu Glu Gln Tyr Asn Ser Thr Tyr Arg Val Val Ser
225                 230                 235                 240 gtc ctc acc gtc ctg cac cag gac tgg ctg aat ggc aag gag tac aag      768
Val Leu Thr Val Leu His Gln Asp Trp Leu Asn Gly Lys Glu Tyr Lys
            245                 250                 255 tgc aag gtc tcc aac aaa gcc ctc cca gcc ccc atc gag aaa acc atc      816
Cys Lys Val Ser Asn Lys Ala Leu Pro Ala Pro Ile Glu Lys Thr Ile
        260                 265                 270 tcc aaa gcc aaa ggg cag ccc cga gaa cca cag gtg tac acc ctg ccc      864
Ser Lys Ala Lys Gly Gln Pro Arg Glu Pro Gln Val Tyr Thr Leu Pro
    275                 280                 285 cca tcc cgg gat gag ctg acc aag aac cag gtc agc ctg acc tgc ctg      912
Pro Ser Arg Asp Glu Leu Thr Lys Asn Gln Val Ser Leu Thr Cys Leu
290                 295                 300 gtc aaa ggc ttc tat ccc agc gac atc gcc gtg gag tgg gag agc aat      960
Val Lys Gly Phe Tyr Pro Ser Asp Ile Ala Val Glu Trp Glu Ser Asn
305                 310                 315                 320 ggg cag ccg gag aac aac tac aag acc acg cct ccc gtg ctg gac tcc     1008
Gly Gln Pro Glu Asn Asn Tyr Lys Thr Thr Pro Pro Val Leu Asp Ser
                325                 330                 335 gac ggc tcc ttc ttc ctc tac agc aag ctc acc gtg gac aag agc agg     1056
Asp Gly Ser Phe Phe Leu Tyr Ser Lys Leu Thr Val Asp Lys Ser Arg
            340                 345                 350 tgg cag cag ggg aac gtc ttc tca tgc tcc gtg atg cat gag gct ctg     1104
Trp Gln Gln Gly Asn Val Phe Ser Cys Ser Val Met His Glu Ala Leu
        355                 360                 365 cac aac cac tac acg cag aag agc ctc tcc ctg tct ccg ggt aaa tga    1152
His Asn His Tyr Thr Gln Lys Ser Leu Ser Leu Ser Pro Gly Lys
    370                 375                 380

<210> SEQ ID NO 2
<211> LENGTH: 383
<212> TYPE: PRT
<213> ORGANISM: Homo sapiens

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125
```

```
Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 3
<211> LENGTH: 1152
<212> TYPE: DNA
<213> ORGANISM: Homo sapiens
<220> FEATURE:
<221> NAME/KEY: CDS
<222> LOCATION: (1)..(1149)

<400> SEQUENCE: 3 atg ggt gta ctg ctc aca cag agg acg ctg ctc agt ctg gtc ctt gca    48
Met Gly Val Leu Leu Thr Gln Arg Thr Leu Leu Ser Leu Val Leu Ala
1               5                   10                  15 ctc ctg ttt cca agc atg gcg agc atg gca atg cac gtg gcc cag cct    96
Leu Leu Phe Pro Ser Met Ala Ser Met Ala Met His Val Ala Gln Pro
            20                  25                  30 gct gtg gta ctg gcc agc agc cga ggc atc gct agc ttt gtg tgt gag   144
Ala Val Val Leu Ala Ser Ser Arg Gly Ile Ala Ser Phe Val Cys Glu
        35                  40                  45 tat gca tct cca ggc aaa tat act gag gtc cgg gtg aca gtg ctt cgg   192
Tyr Ala Ser Pro Gly Lys Tyr Thr Glu Val Arg Val Thr Val Leu Arg
    50                  55                  60 cag gct gac agc cag gtg act gaa gtc tgt gcg gca acc tac atg atg   240
Gln Ala Asp Ser Gln Val Thr Glu Val Cys Ala Ala Thr Tyr Met Met
65                  70                  75                  80
```

```
ggg aat gag ttg acc ttc cta gat gat tcc atc tgc acg ggc acc tcc      288
Gly Asn Glu Leu Thr Phe Leu Asp Asp Ser Ile Cys Thr Gly Thr Ser
                85                  90                  95 agt gga aat caa gtg aac ctc act atc caa gga ctg agg gcc atg gac      336
Ser Gly Asn Gln Val Asn Leu Thr Ile Gln Gly Leu Arg Ala Met Asp
            100                 105                 110 acg gga ctc tac atc tgc aag gtg gag ctc atg tac cca ccg cca tac      384
Thr Gly Leu Tyr Ile Cys Lys Val Glu Leu Met Tyr Pro Pro Pro Tyr
        115                 120                 125 tac gag ggc ata ggc aac gga acc cag att tat gta att gat cca gaa      432
Tyr Glu Gly Ile Gly Asn Gly Thr Gln Ile Tyr Val Ile Asp Pro Glu
    130                 135                 140 ccg tgc cca gat tct gat cag gag ccc aaa tct tct gac aaa act cac      480
Pro Cys Pro Asp Ser Asp Gln Glu Pro Lys Ser Ser Asp Lys Thr His
145                 150                 155                 160 aca tcc cca ccg tcc cca gca cct gaa ctc ctg ggg gga tcg tca gtc      528
Thr Ser Pro Pro Ser Pro Ala Pro Glu Leu Leu Gly Gly Ser Ser Val
                165                 170                 175 ttc ctc ttc ccc cca aaa ccc aag gac acc ctc atg atc tcc cgg acc      576
Phe Leu Phe Pro Pro Lys Pro Lys Asp Thr Leu Met Ile Ser Arg Thr
            180                 185                 190 cct gag gtc aca tgc gtg gtg gtg gac gtg agc cac gaa gac cct gag      624
Pro Glu Val Thr Cys Val Val Val Asp Val Ser His Glu Asp Pro Glu
        195                 200                 205 gtc aag ttc aac tgg tac gtg gac ggc gtg gag gtg cat aat gcc aag      672
Val Lys Phe Asn Trp Tyr Val Asp Gly Val Glu Val His Asn Ala Lys
    210                 215                 220 aca aag ccg cgg gag gag cag tac aac agc acg tac cgt gtg gtc agc      720
Thr Lys Pro Arg Glu Glu Gln Tyr Asn Ser Thr Tyr Arg Val Val Ser
225                 230                 235                 240 gtc ctc acc gtc ctg cac cag gac tgg ctg aat ggc aag gag tac aag      768
Val Leu Thr Val Leu His Gln Asp Trp Leu Asn Gly Lys Glu Tyr Lys
                245                 250                 255 tgc aag gtc tcc aac aaa gcc ctc cca gcc ccc atc gag aaa acc atc      816
Cys Lys Val Ser Asn Lys Ala Leu Pro Ala Pro Ile Glu Lys Thr Ile
            260                 265                 270 tcc aaa gcc aaa ggg cag ccc cga gaa cca cag gtg tac acc ctg ccc      864
Ser Lys Ala Lys Gly Gln Pro Arg Glu Pro Gln Val Tyr Thr Leu Pro
        275                 280                 285 cca tcc cgg gat gag ctg acc aag aac cag gtc agc ctg acc tgc ctg      912
Pro Ser Arg Asp Glu Leu Thr Lys Asn Gln Val Ser Leu Thr Cys Leu
    290                 295                 300 gtc aaa ggc ttc tat ccc agc gac atc gcc gtg gag tgg gag agc aat      960
Val Lys Gly Phe Tyr Pro Ser Asp Ile Ala Val Glu Trp Glu Ser Asn
305                 310                 315                 320 ggg cag ccg gag aac aac tac aag acc acg cct ccc gtg ctg gac tcc     1008
Gly Gln Pro Glu Asn Asn Tyr Lys Thr Thr Pro Pro Val Leu Asp Ser
                325                 330                 335 gac ggc tcc ttc ttc ctc tac agc aag ctc acc gtg gac aag agc agg     1056
Asp Gly Ser Phe Phe Leu Tyr Ser Lys Leu Thr Val Asp Lys Ser Arg
            340                 345                 350 tgg cag cag ggg aac gtc ttc tca tgc tcc gtg atg cat gag gct ctg     1104
Trp Gln Gln Gly Asn Val Phe Ser Cys Ser Val Met His Glu Ala Leu
        355                 360                 365 cac aac cac tac acg cag aag agc ctc tcc ctg tct ccg ggt aaa tga     1152
His Asn His Tyr Thr Gln Lys Ser Leu Ser Leu Ser Pro Gly Lys
    370                 375                 380

<210> SEQ ID NO 4
```

<211> LENGTH: 383
<212> TYPE: PRT
<213> ORGANISM: Homo sapiens

<400> SEQUENCE: 4

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

```
<210> SEQ ID NO 5
<211> LENGTH: 636
<212> TYPE: DNA
<213> ORGANISM: Homo sapiens
<220> FEATURE:
<221> NAME/KEY: CDS
<222> LOCATION: (1)..(636)

<400> SEQUENCE: 5 atg ggt gta ctg ctc aca cag agg acg ctg ctc agt ctg gtc ctt gca      48
Met Gly Val Leu Leu Thr Gln Arg Thr Leu Leu Ser Leu Val Leu Ala
1               5                   10                  15 ctc ctg ttt cca agc atg gcg agc atg gca atg cac gtg gcc cag cct      96
Leu Leu Phe Pro Ser Met Ala Ser Met Ala Met His Val Ala Gln Pro
            20                  25                  30 gct gtg gta ctg gcc agc agc cga ggc atc gcc agc ttt gtg tgt gag     144
Ala Val Val Leu Ala Ser Ser Arg Gly Ile Ala Ser Phe Val Cys Glu
        35                  40                  45 tat gca tct cca ggc aaa gcc act gag gtc cgg gtg aca gtg ctt cgg     192
Tyr Ala Ser Pro Gly Lys Ala Thr Glu Val Arg Val Thr Val Leu Arg
    50                  55                  60 cag gct gac agc cag gtg act gaa gtc tgt gcg gca acc tac atg atg     240
Gln Ala Asp Ser Gln Val Thr Glu Val Cys Ala Ala Thr Tyr Met Met
65                  70                  75                  80 ggg aat gag ttg acc ttc cta gat gat tcc atc tgc acg ggc acc tcc     288
Gly Asn Glu Leu Thr Phe Leu Asp Asp Ser Ile Cys Thr Gly Thr Ser
                85                  90                  95 agt gga aat caa gtg aac ctc act atc caa gga ctg agg gcc atg gac     336
Ser Gly Asn Gln Val Asn Leu Thr Ile Gln Gly Leu Arg Ala Met Asp
            100                 105                 110 acg gga ctc tac atc tgc aag gtg gag ctc atg tac cca ccg cca tac     384
Thr Gly Leu Tyr Ile Cys Lys Val Glu Leu Met Tyr Pro Pro Pro Tyr
        115                 120                 125 tac ctg ggc ata ggc aac gga acc cag att tat gta att gat cca gaa     432
Tyr Leu Gly Ile Gly Asn Gly Thr Gln Ile Tyr Val Ile Asp Pro Glu
    130                 135                 140 ccg tgc cca gat tct gac ttc ctc ctc tgg atc ctt gca gca gtt agt     480
Pro Cys Pro Asp Ser Asp Phe Leu Leu Trp Ile Leu Ala Ala Val Ser
145                 150                 155                 160 tcg ggg ttg ttt ttt tat agc ttt ctc ctc aca gct gtt tct ttg agc     528
Ser Gly Leu Phe Phe Tyr Ser Phe Leu Leu Thr Ala Val Ser Leu Ser
                165                 170                 175 aaa atg cta aag aaa aga agc cct ctt aca aca ggg gtc tat gtg aaa     576
Lys Met Leu Lys Lys Arg Ser Pro Leu Thr Thr Gly Val Tyr Val Lys
            180                 185                 190 atg ccc cca aca gag cca gaa tgt gaa aag caa ttt cag cct tat ttt     624
Met Pro Pro Thr Glu Pro Glu Cys Glu Lys Gln Phe Gln Pro Tyr Phe
        195                 200                 205 att ccc atc aat                                                      636
Ile Pro Ile Asn
    210

<210> SEQ ID NO 6
<211> LENGTH: 212
<212> TYPE: PRT
<213> ORGANISM: Homo sapiens

<400> SEQUENCE: 6

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30
```

```
Ala Val Val Leu Ala Ser Ser Arg Gly Ile Ala Ser Phe Val Cys Glu
         35                  40                  45
Tyr Ala Ser Pro Gly Lys Ala Thr Glu Val Arg Val Thr Val Leu Arg
     50                  55                  60
Gln Ala Asp Ser Gln Val Thr Glu Val Cys Ala Ala Thr Tyr Met Met
 65                  70                  75                  80
Gly Asn Glu Leu Thr Phe Leu Asp Asp Ser Ile Cys Thr Gly Thr Ser
                 85                  90                  95
Ser Gly Asn Gln Val Asn Leu Thr Ile Gln Gly Leu Arg Ala Met Asp
             100                 105                 110
Thr Gly Leu Tyr Ile Cys Lys Val Glu Leu Met Tyr Pro Pro Pro Tyr
         115                 120                 125
Tyr Leu Gly Ile Gly Asn Gly Thr Gln Ile Tyr Val Ile Asp Pro Glu
     130                 135                 140
Pro Cys Pro Asp Ser Asp Phe Leu Leu Trp Ile Leu Ala Ala Val Ser
145                 150                 155                 160
Ser Gly Leu Phe Phe Tyr Ser Phe Leu Leu Thr Ala Val Ser Leu Ser
                 165                 170                 175
Lys Met Leu Lys Lys Arg Ser Pro Leu Thr Thr Gly Val Tyr Val Lys
             180                 185                 190
Met Pro Pro Thr Glu Pro Glu Cys Glu Lys Gln Phe Gln Pro Tyr Phe
         195                 200                 205
Ile Pro Ile Asn
    210

<210> SEQ ID NO 7
<211> LENGTH: 16
<212> TYPE: DNA
<213> ORGANISM: Artificial Sequence
<220> FEATURE:
<223> OTHER INFORMATION: GILZ specific TaqMan MGB probe

<400> SEQUENCE: 7
agaggacttc acgtgt                                                16

<210> SEQ ID NO 8
<211> LENGTH: 16
<212> TYPE: DNA
<213> ORGANISM: Artificial Sequence
<220> FEATURE:
<223> OTHER INFORMATION: Forward Primer

<400> SEQUENCE: 8
agaggacttc acgtgt                                                16

<210> SEQ ID NO 9
<211> LENGTH: 19
<212> TYPE: DNA
<213> ORGANISM: Artificial Sequence
<220> FEATURE:
<223> OTHER INFORMATION: Reverse Primer

<400> SEQUENCE: 9
tggtgggttt ggcattcaa                                             19
```